(12) United States Patent
Tsuji et al.

(10) Patent No.: US 8,883,745 B2
(45) Date of Patent: Nov. 11, 2014

(54) C—GLYCOLIPIDS WITH ENHANCED TH-1 PROFILE

(75) Inventors: Moriya Tsuji, New York, NY (US); Guangwu Chen, Flushing, NY (US); Richard W. Franck, Riverside, CT (US); Guangli Yang, Forest Hills, NY (US)

(73) Assignees: New York University, New York, NY (US); The Aaron Diamond Aids Research Center For The City Of New York, New York, NY (US); Research Foundation Of The City University Of New York, New York, NY (US)

( * ) Notice: Subject to any disclaimer, the term of this patent is extended or adjusted under 35 U.S.C. 154(b) by 1209 days.

(21) Appl. No.: 12/302,011

(22) PCT Filed: May 22, 2007

(86) PCT No.: PCT/US2007/069461
§ 371 (c)(1),
(2), (4) Date: Nov. 21, 2008

(87) PCT Pub. No.: WO2007/137258
PCT Pub. Date: Nov. 29, 2007

(65) Prior Publication Data
US 2010/0233207 A1  Sep. 16, 2010

Related U.S. Application Data

(60) Provisional application No. 60/802,739, filed on May 22, 2006.

(51) Int. Cl.
*A01N 43/04* (2006.01)
*A61K 31/70* (2006.01)
*A61K 39/21* (2006.01)
*A61K 39/12* (2006.01)
*A61K 39/00* (2006.01)
*A61K 39/38* (2006.01)
*A61K 39/29* (2006.01)
*C07H 13/06* (2006.01)
*A61K 31/7004* (2006.01)
*A61K 31/7042* (2006.01)
*A61K 31/7028* (2006.01)
*C07H 7/00* (2006.01)
*C07H 15/06* (2006.01)

(52) U.S. Cl.
CPC ............ *C07H 13/06* (2013.01); *A61K 31/7004* (2013.01); *A61K 31/7042* (2013.01); *A61K 31/7028* (2013.01); *C07H 7/00* (2013.01); *C07H 15/06* (2013.01)
USPC .... 514/25; 424/208.1; 424/184.1; 424/204.1; 424/227.1; 424/277.1

(58) Field of Classification Search
CPC . C07H 7/00; A61K 31/7004; A61K 31/7028; A61K 31/7042
USPC ........ 514/25; 424/208.1, 184.1, 204.1, 227.1, 424/272.1, 277.1
See application file for complete search history.

(56) References Cited

U.S. PATENT DOCUMENTS

| | | | |
|---|---|---|---|
| 6,635,622 B2 | 10/2003 | Tomiyama et al. | |
| 2005/0222048 A1* | 10/2005 | Tsuji et al. | 514/23 |
| 2006/0211856 A1* | 9/2006 | Tsuji et al. | 536/53 |

FOREIGN PATENT DOCUMENTS

WO    WO-03105769    12/2003

OTHER PUBLICATIONS

Schmieg, et al., 2003. "Superior Protection against Malaria and Melanoma Metastases by a C—glycoside Analogue of the Natural Killer T Cell Ligand α-Galactoslyceramide". J. Exp. Med. 198(11): 1631-1641.
Chen, et al., 2004. "Efficient Synthesis of α—C—Galactosyl Ceramide Immunostimulants: Use of Ethylene-Promoted Olefin Cross-Metathesis". Org. Lett. 6(22): 4077-4080.
Tetsuya Toba et al., "A concise synthesis of (3S,4S,5R)-1-(α-D-galactopyranosyl)-3-tetracosanoylamino-4,5-decanediol, a C—glycoside analogue of immunomodulating α-galactosylceramide OCH", Tetrahedron Letters 46 (2005) 5043-5047.

* cited by examiner

*Primary Examiner* — Scarlett Goon
(74) *Attorney, Agent, or Firm* — Fish & Richardson P.C.

(57) ABSTRACT

The invention is directed to novel synthetic C-glycolipids that selectively induce a ThI-type immune response characterized by enhanced IL-12 secretion and increased activation of dendritic cells. The compounds of the invention are thereby useful in treating infections, cancers, cell proliferative disorders, and autoimmune diseases, both directly and as adjuvants.

22 Claims, 9 Drawing Sheets

C57BL/6 mice

SEQUENCE LISTING

```
<160> NUMBER OF SEQ ID NOS: 8

<210> SEQ ID NO 1
<211> LENGTH: 21
<212> TYPE: PRT
<213> ORGANISM: Plasmodium yoelii
```

```
<400> SEQUENCE: 1

Tyr Asn Arg Asn Ile Val Asn Arg Leu Leu Gly Asp Ala Leu Asn Gly
1               5                   10                  15

Lys Pro Glu Glu Lys
            20

<210> SEQ ID NO 2
<211> LENGTH: 9
<212> TYPE: PRT
<213> ORGANISM: Plasmodium yoelii

<400> SEQUENCE: 2

Ser Tyr Val Pro Ser Ala Glu Gln Ile
1               5

<210> SEQ ID NO 3
<211> LENGTH: 8
<212> TYPE: PRT
<213> ORGANISM: Plasmodium falciparum

<400> SEQUENCE: 3

Asn Val Asp Pro Asn Ala Asn Pro
1               5

<210> SEQ ID NO 4
<211> LENGTH: 20
<212> TYPE: PRT
<213> ORGANISM: Plasmodium falciparum

<400> SEQUENCE: 4

Glu Tyr Leu Asn Lys Ile Gln Asn Ser Leu Ser Thr Glu Trp Ser Pro
1               5                   10                  15

Cys Ser Val Thr
            20

<210> SEQ ID NO 5
<211> LENGTH: 12
<212> TYPE: PRT
<213> ORGANISM: Plasmodium falciparum

<400> SEQUENCE: 5

Asn Ala Asn Pro Asn Ala Asn Pro Asn Ala Asn Pro
1               5                   10

<210> SEQ ID NO 6
<211> LENGTH: 10
<212> TYPE: PRT
<213> ORGANISM: Human immunodeficiency virus

<400> SEQUENCE: 6

Arg Gly Pro Gly Arg Ala Phe Val Thr Ile
1               5                   10

<210> SEQ ID NO 7
<211> LENGTH: 25
<212> TYPE: DNA
<213> ORGANISM: Artificial Sequence
<220> FEATURE:
<223> OTHER INFORMATION: primer

<400> SEQUENCE: 7 gggattggt tttgacgttt ttgcg                                      25
```

```
<210> SEQ ID NO 8
<211> LENGTH: 30
<212> TYPE: DNA
<213> ORGANISM: Artificial Sequence
<220> FEATURE:
<223> OTHER INFORMATION: primer

<400> SEQUENCE: 8
aagcattaaa taaagcgaat acatccttat                                   30
```

C—GLYCOLIPIDS WITH ENHANCED TH-1 PROFILE

FIELD OF THE INVENTION

The present invention is directed to novel synthetic C-glycolipids that selectively induce a Th1-type immune response characterized by enhanced IL-12 secretion and increased activation of antigen-presenting cells (APCs) such as dendritic cells, and are useful in treating infections, cancers, cell proliferative disorders, and autoimmune diseases, both directly and as adjuvants.

BACKGROUND OF THE INVENTION

Th1-type and Th2-type immune responses were originally defined as immune responses mediated by two distinct CD4+ T cell (helper T cell—Th) subsets that secrete two different groups of cytokines. For a recent review, see Berkers and Ovaa, *Trends Pharmacol. Sci.*, 2005, 26(5):252-257, and references cited therein.

Th1 cells secrete Th1-type cytokines including interferon-gamma (IFN-γ) and interleukin 12 (IL-12). The principal function of Th1-type cytokines is to support cell-mediated immunity that results in the elimination of tumor cells, viruses and other intracellular pathogens by stimulating phagocyte-mediated defense and increasing the activity of CD8+ T cells (cytotoxic T cells) and natural killer (NK) cells. In addition, Th1 cytokines inhibit the switching of immunoglobulin synthesis by B cells, and suppress the production of certain immunoglobulin isotypes such as IgG1 and IgE, the latter being particularly important for causing allergies. IL-12 is secreted mainly by antigen-presenting cells (APCs) including dendritic cells (DCs) and macrophages, and activates CD8+ T cells and NK cells. Th2 cells secrete Th2-type cytokines including IL-4, IL-5, IL-10, and IL-13. The principal function of Th2-type cytokines is to support humoral immunity (e.g., stimulate IgE and eosinophil/mast cell-mediated immune reactions) and to down-regulate Th1-type immune responses.

Dysregulation of the balance between Th1- and Th2-type immune responses causes disease. Many types of cancer are characterized by a predominant Th2-type response, and many pathogens evade the immune system by producing cytokines that shift the Th1-Th2 balance to the Th2 mode (Wilson and Delovitch, 2003, *Nat. Rev. Immunol.*, 3: 211-222; Dredge, *Cancer Immunol. Immunother.*, 2002, 51:521-531; Servet and Zitvogel, *Curr Mol. Med.*, 2002, 2:739-756; Pinto, *Pediatrics*, 2006, Apr. 17 [Epub ahead of print]). Many autoimmune diseases such as asthma are also characterized by the shift of the Th1-Th2 balance to the Th2 mode. On the contrary, autoimmune diseases such as type 1 diabetes and multiple sclerosis are mediated by autopathogenic Th1 cells and are characterized by hyporesponsive Th2 cells, which leads to a Th1-like cytokine profile (Hayakawa et al., 2004, *Curr. Med. Chem.*, 11: 241-252; Wilson and Delovitch, 2003, *Nat. Rev. Immunol.*, 3: 211-222; Van Kaer, 2004, *Immunol. Cell Biol.*, 82: 315-322).

Natural killer T (NKT) cells have a crucial role in regulating Th1- and Th2-type immune responses. NKT cells are a unique population of lymphocytes that co-express markers of NK cells along with a semi-invariant T cell receptor (TCR). In mice, the TCR of most NKT cells consists of an invariant Vα chain encoded by the Vα14 and Jα18 gene segments paired with a variable set of Vβ chains encoded mainly by the Vβ8.2, Vβ7 or Vβ2 gene segments. This TCR enables NKT cells to recognize the major histocompatibility complex (MHC) class I-like molecule CD1d, which is capable of presenting hydrophobic molecules such as lipids and hydrophobic peptides to NKT cells.

Thus far, only a few molecules have been shown to activate NKT cells. Of these, alpha-galactosylceramide (α-GalCer), a glycolipid originally extracted from Okinawan marine sponges (Natori et al., *Tetrahedron*, 50: 2771-2784, 1994) is the best characterized. A synthetic analog of α-GalCer, KRN 7000 (2S,3S,4R)-1-O-(α-D-galactopyranosyl)-2-(N-hexacosanoylamino)-1,3,4-,-octadecanetriol, can be obtained from Pharmaceutical Research Laboratories, Kirin Brewery (Gumna, Japan) or synthesized as described in Morita et al., *J. Med. Chem.*, 1995, 38: 2176-2187. Other α-GalCer derivatives are described in U.S. Pat. No. 5,780,441 (Kirin). Following the initial disclosures by Kirin, α-GalCer has shown potential in the treatment of several diseases, including primary tumors and their metastases, infectious diseases such as malaria and hepatitis B, and several autoimmune diseases such as diabetes and asthma (see Hayakawa et al, 2004, *Curr. Med. Chem.*, 11:241-252; Wilson and Delovitch, 2003, *Nat. Rev. Immunol.*, 3:211-222; Taniguchi et al, 2003, *Annu. Rev. Immunol.*, 21:483-513; Van Kaer 2004, *Immunol. Cell Biol.* 82:315-322). It has also been demonstrated that α-GalCer can be used as an adjuvant capable of enhancing and/or extending the duration of the protective immune responses induced by other antigens (see US 2003-0157135 and Gonzalez-Aseguinolaza et al., *J Exp Med.*, 2002, 195:617-24).

α-GalCer can activate NKT cells both in vitro and in vivo (Kawano et al., 1997, *Science*, 278:1626-1629; Burdin et al., 1998, *J. Immunol.*, 161:3271-3281; Spada et al., 1998, *J. Exp. Med.*, 188:1529-1534; Brossay et al., 1998, *J. Exp. Med.* 188:1521-1528). As shown in FIG. 1, α-GalCer, when present with CD1d by APCs such as monocytes, monocyte-derived immature dendritic cells and macrophages, interacts with the TCR of NKT cells, which subsequently activate both the NKT cells and the APCs, and lead to the production of both the Th1-type cytokine IFN-γ and Th2-type cytokine IL-4 by NKT cells. The IL-12 receptor is then activated on the cell surface of the NKT cells and, simultaneously, IL-12 is produced by the activated APCs. IL-12 produced by the APCs induces a second wave of IFN-γ from the NKT cells and activates NK cells to also produce IFN-γ (Hayakawa et al, 2004, *Curr. Med. Chem.*, 11:241-252; Kawano et al., 1997, *Science*, 278, 1626-1629; Godfrey et al., 2000, *Immunol. Today*, 21:573-583; Wilson et al., 2002, *Trends Mol. Med.*, 8:225-231; Matsuda et al., 2000, *J. Exp. Med.*, 192:741-753). Activation of NKT cells by α-GalCer thus may result in the secondary activation of several other cell types, including NK cells, B cells, CD8+ T cells, dendritic cells and myeloid cells and in the differentiation of CD4+ T cells into either Th1 or Th2 cells.

It has been demonstrated that the administration of α-GalCer to mice resulted rapidly in strong anti-malaria activity, inhibiting the development of intra-hepatocytic stages of the rodent malaria parasites, *P. yoeli* and *P. berghei* (Gonzalez-Aseguinolaza et al., 2000, *Proc. Natl. Acad. Sci. USA*, 97: 8461-8466). α-GalCer was unable to inhibit parasite development in the liver of mice lacking either IFN-γ or the IFN-γ receptor, indicating that the anti-malaria activity of the glycolipid is primarily mediated by IFN-γ. IL-4 stimulated by α-Gal-Cer allows the glycolipid to ameliorate a number of different autoimmune diseases, including autoimmune type 1 diabetes and autoimmune encephalomyelitis (Wilson et al., 2002, *Trends Mol. Med.*, 8:225-231).

Importantly, in addition to its ability to stimulate immune responses, it has been demonstrated that α-GalCer, independently of its dosage, does not induce toxicity in rodents and monkeys (Nakagawa et al., 1998, *Cancer Res.*, 58: 1202-1207).

The effectiveness of α-GalCer therapy, however, is severely limited by the concomitant stimulation of both Th1- and Th2-type cytokines (i.e., IFN-γ, IL-12 and IL-4) (Pal et al., 2001, *J. Immunol.*, 166:662-668; Berkers and Ovaa, *Trends Pharmacol. Sci.*, 2005, 26:252-257). Indeed, little effect was observed in patients with solid tumors in a Phase I study with α-GalCer (Giaccone et al., 2002, *Clin. Cancer Res.*, 8: 3702-3709). Treatment with α-GalCer has been shown to be more effective if the cytokine profile of NKT cells is shifted, e.g., towards Th1-type by administration of CD1d-pulsed dendritic cells (Fujii et al., 2002, *Nat. Immunol.*, 3: 867-874).

An α-GalCer analog that could selectively induce Th1- or Th2-type immune response would thus have a more promising therapeutic potential.

Several α-C-GalCer analogs have been recently developed, where a carbon atom replaces the oxygen atom of the glycosidic bond. See, e.g., U.S. Pat. No. 6,635,622; Schmieg et al, 2003, *J. Exp. Med*, 198(11):1631-1641; Chen et al., *Org. Lett.*, 2004, 6:4077-80; Yang et al., *Angew Chem Int Ed Engl.*, 2004, 43:3818-22, and commonly owned U.S. patent applications Ser. No. 10/462,211 (US 2004-0127429); Ser. No. 11/193,852 (US 2006-0019246); Ser. No. 11/096,340 (US 2005-0222048). Such analogs are resistant to deglycosylation and therefore have a longer shelf-life (Bertozzi et al., Synthesis of C-glycosides: stable mimics of O-glycosidic linkages. In *Modern Methods in Carbohydrate Synthesis*. Khan and O'Neill, editors. Harwood Academic Publishers, London, UK, 1996, p. 316-351; Bertozzi et al., 1992. *J. Am. Chem. Soc.*, 114:10639-10641; Levy and Tang, *The Chemistry of C-Glycosides*, Elsevier Science Ltd., 1995; Postema, *C-Glycoside Synthesis*, CRC Press, Inc., 1995).

α-C-GalCer CRONY 101 was the first example of a C-glycoside that has a significantly improved therapeutic potential compared with its O-glycosidic counterpart. As demonstrated in Schmieg et al. (2003, *J. Exp. Med.*, 198: 1631-1641) and Yang et al. (2004, *Angew. Chem. Int. Ed. Engl.*, 43: 3818-3822), in vivo administration of CRONY 101 results in diminished production of the Th2-type cytokine IL-4 (as compared to α-GalCer) and enhanced, prolonged production of the Th1-type cytokines IFN-γ and IL-12 leading to a 100 and 1000-fold improved activity against melanoma metastases and malaria, respectively.

The Th1-type cytokine IL-12 has recently attracted a lot of attention because of its essential role in the interaction between the innate and adaptive arms of immunity by regulating inflammatory responses and innate resistance to infection and cancer (reviewed in Colombo and Trinchieri, *Cytokine Growth Factor Rev.*, 2002, 13:155-68; Watford, *Cytokine Growth Factor Rev.*, 2003, 14:361-368). Endogenous IL-12 is required for resistance to many pathogens and tumors. Indeed, in experimental tumor models, recombinant IL-12 treatment has a dramatic anti-tumor effect on transplantable tumors, chemically induced tumors, and tumors arising spontaneously in genetically modified mice.

As specified above, IL-12 is mostly secreted by various APCs such as dendritic cells and macrophages and contributes to Th1-type immune response (Roitt, Brostoff, Male, Immunology, Mosby ed., 6th ed.; Ma and Trinchieri, *Adv Immunol.*, 2001, 79:55-92; Hilkens, *Blood*, 1997, 90:1920-1926; Szabo, *Annu. Rev. Immunol.*, 2003, 21:713-58). IFN-γ and a cascade of other secondary and tertiary pro-inflammatory cytokines induced by IL-12 have a direct toxic effect on the infected and tumor cells or may activate potent anti-angiogenic mechanisms. The stimulating activity of IL-12 on antigen-specific immunity relies mostly on its ability to determine or augment Th1 and cytotoxic T lymphocyte responses. Because of this ability, IL-12 has a potent adjuvant activity in cancer and other vaccines. The promising data obtained in the pre-clinical models of anti-tumor immunotherapy have raised much hope that IL-12 could be a powerful therapeutic agent against cancer. However, excessive toxicity observed in the IL-12 clinical trials point to the necessity to achieve IL-12 activation in a local rather than systemic fashion.

SUMMARY OF THE INVENTION

As follows from the Background Section, above, there is a great need in the art for new immuno-stimulatory compounds that have low in vivo toxicity, high in vivo stability, and the ability to selectively induce Th1-type immune responses, in particular, Th1-type immune responses associated with increased local IL-12 production. The present invention addresses these and other needs in the art by providing novel synthetic C-glycolipids. The compounds of the present invention can treat diseases which require a Th-1-type response for control including, but not limited to, various infections, cancers, proliferative disorders, and autoimmune diseases. These compounds can also augment an immunogenicity of an antigen in a mammal.

The C-glycolipids of the present invention include compounds of formula (I)

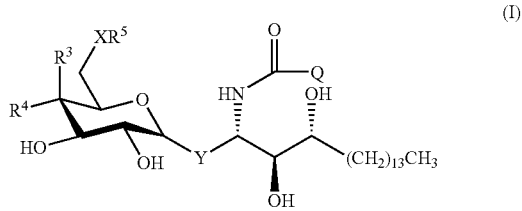

where

X is O or NH;

Y is —$CH_2$—$CH_2$— or —CH═CH—;

when Y is —$CH_2$—$CH_2$—, Q is $C_{23}$-$C_{33}$ alkenyl or —$R^1$—O—$R^2$;

when Y is —CH═CH—, Q is $C_{27}$-$C_{32}$ alkyl, $C_{23}$-$C_{32}$ alkenyl, —$R^1$—O—$R^2$, or $C_6$-$C_8$ alkyl substituted with phenyl;

$R^1$ and $R^2$ are substituted or unsubstituted alkyl or alkenyl groups such that $R^1$ and $R^2$ combined have from 23 to 32 carbon atoms;

$R^3$ is —OH or a monosaccharide and $R^4$ is H, or $R^3$ is H and $R^4$ is —OH or a monosaccharide; and $R^5$ is hydrogen or a monosaccharide, and pharmaceutically acceptable salts or esters thereof.

In a preferred embodiment; Y is —CH═CH— in a trans or cis conformation. More preferably, Y is —CH═CH— in a trans conformation.

Preferred are those compounds which stimulate increased secretion of IL-12. Such compounds include:

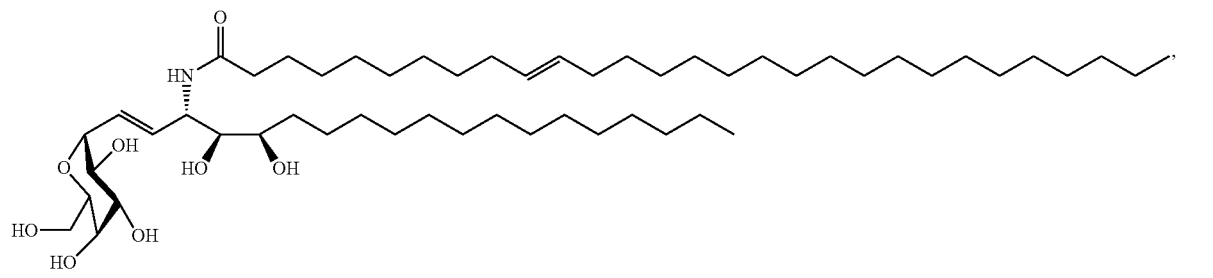

trans-(A-1)

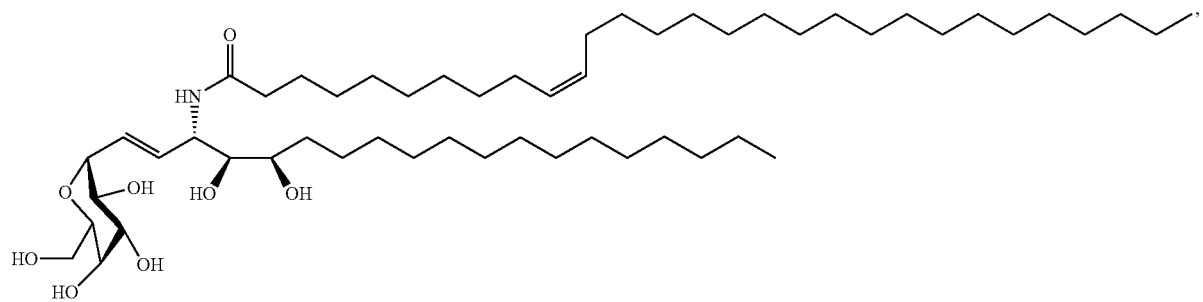

cis-(A-1)

(depicted above are the trans- and cis-conformers of the fatty acid Q chain [also called GCK109 and GCK151, respectively]). In each case the group Y is a trans-ethylene.

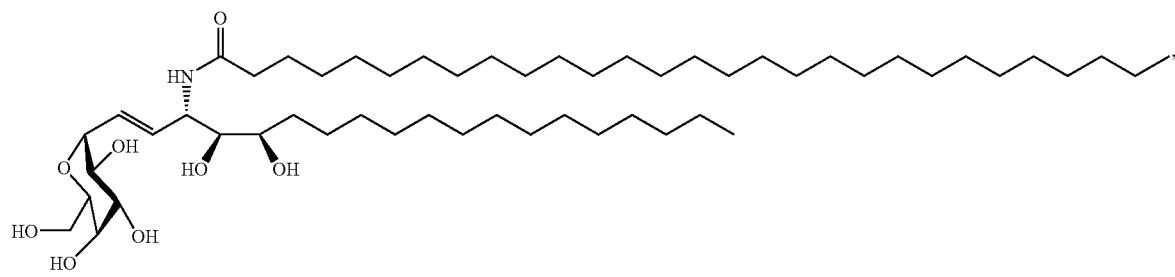

(A-2)

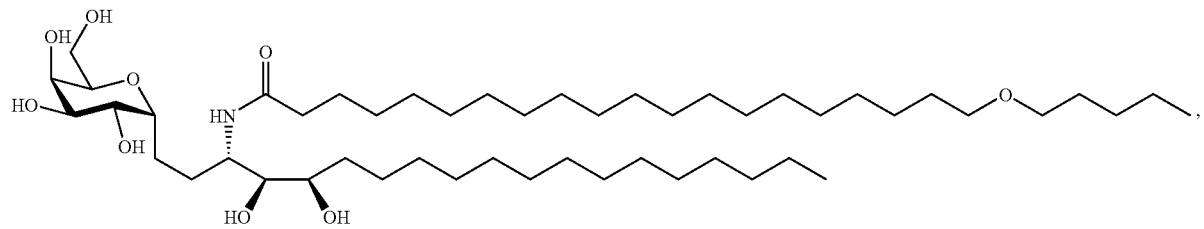

(A-5)

and pharmaceutically acceptable salts and esters thereof. These compounds provide a Th1-type response of superior specificity and having a superior pharmacokinetic profile than CRONY. Without being bound by any particular theory, these compounds are believed to provide an improved balanced secretion of IL-12 by dendritic cells and IFN-γ by NKT or NK cells, which further reflects the specificity of the response and improves safety of the compounds. These compounds also do not substantially stimulate secretion of IL-4 by NKT or NK cells.

Additional C-glycolipids of the present invention include compounds of the formula

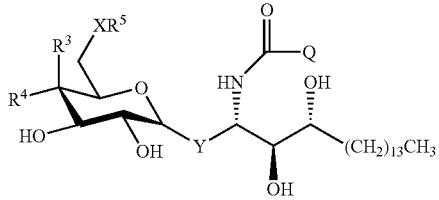

(I)

wherein

Y is —CH$_2$—CH$_2$—;

X is O, R$^5$ is H, R$^3$ is OH, R$^4$ is H; and

Q is —(CH$_2$)$_{27}$—CH$_3$, and pharmaceutically acceptable salts and esters thereof.

Another embodiment of the invention is a pharmaceutical composition comprising a compound as defined above in association with a pharmaceutically acceptable carrier. The pharmaceutical composition may further comprise an antigen.

Yet another embodiment is a method of stimulating a specific Th1-type response by NKT cells and activating dendritic cells in a mammal, which method comprises administering to the mammal an effective amount of a compound of the present invention.

The compounds of the invention induce Th1-type immune responses so selectively and efficiently that they are effective in treatment both when used directly and when used as adjuvants conjointly with disease-specific antigens. Therefore, yet another embodiment of the invention is a method for treating a disease which requires a Th-1-type response for control in a mammal in need thereof, which method comprises administering to the mammal an effective amount of the compound of formula (I). Non-limiting examples of diseases which requires a Th-1-type response for control include infections, cancers, cell proliferative disorders, and Th2-type autoimmune diseases. In a preferred embodiment, the disease which requires a Th-1-type response for control is an infectious viral disease, e.g., a human immunodeficiency virus (HIV) infection, hepatitis C virus (HCV) infection, hepatitis B virus (HBV) infection, herpes virus infection, or respiratory syncytial virus (RSV) infection. In another preferred embodiment, the disease is a cancer, e.g., a solid tumor such as a carcinoma of the prostate or breast. In still another preferred embodiment, the disease is asthma.

Yet another embodiment is a method for augmenting the immunogenicity of an antigen in a mammal by immunizing the mammal with the antigen and conjointly with an adjuvant comprising the compound of formula (I). In a preferred embodiment, the antigen is HIV-specific, malaria-specific, or prostate cancer-specific.

Yet another embodiment is a method of preparing the compounds of formula (I) as described herein. A distinct embodiment is a method of preparing a compound of formula (I)

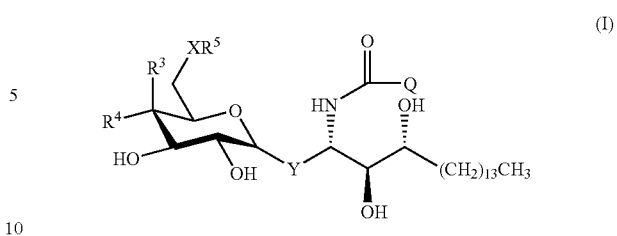

wherein

X is O or NH;

Y is —CH$_2$—CH$_2$— or —CH=CH—;

when Y is —CH$_2$—CH$_2$—, Q is C$_{23}$-C$_{32}$ alkenyl or —R$^1$—O—R$^2$;

when Y is —CH=CH—, Q is C$_{27}$-C$_{32}$ alkyl, C$_{23}$-C$_{32}$ alkenyl, —R$^1$—O—R$^2$, or C$_6$-C$_8$ alkyl substituted with phenyl;

R$^1$ and R$^2$ are substituted or unsubstituted alkyl or alkenyl groups such that R$^1$ and R$^2$ combined have from 23 to 32 carbon atoms;

R$^3$ is —OH or a monosaccharide and R$^4$ is H, or R$^3$ is H and R$^4$ is —OH or a monosaccharide; and R$^5$ is hydrogen or a monosaccharide;

and pharmaceutically acceptable salts or esters thereof.

The method comprises the steps of:

(a) reacting a compound of formula (II)

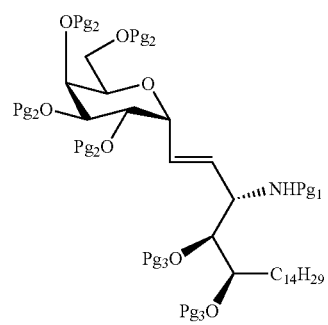

(II)

to first remove Pg1, followed by treatment with a p-nitrophenyl ester having the formula III:

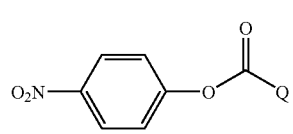

(III)

wherein Q is as defined above; and (b) subsequently deprotecting Pg2 and Pg3, and optionally hydrogenating the carbon-carbon double bond adjacent the cyclic group to form a compound of formula (I). According to one preferred embodiment, the compound of formula (II) is

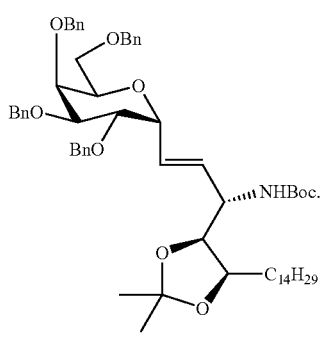

DETAILED DESCRIPTION OF THE INVENTION

Definitions

Figure 1:
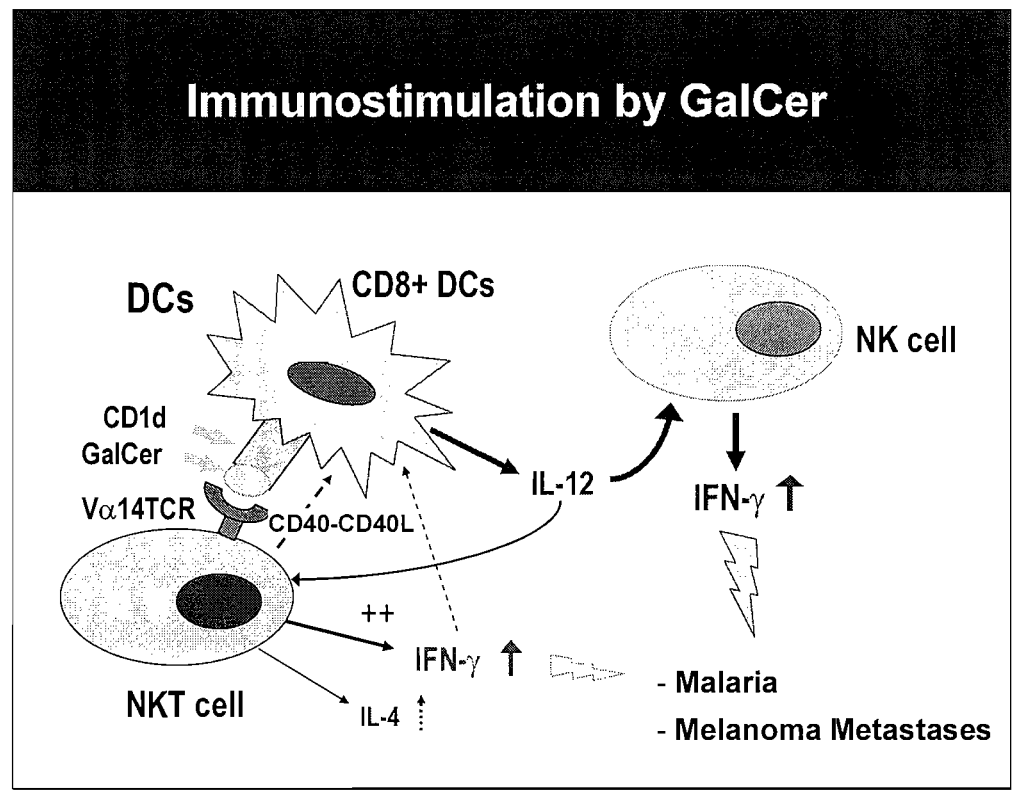
FIG. 1 is a schematic representation of cytokine and immune cell activation by O- and C-glycolipids.
Figure 2A:
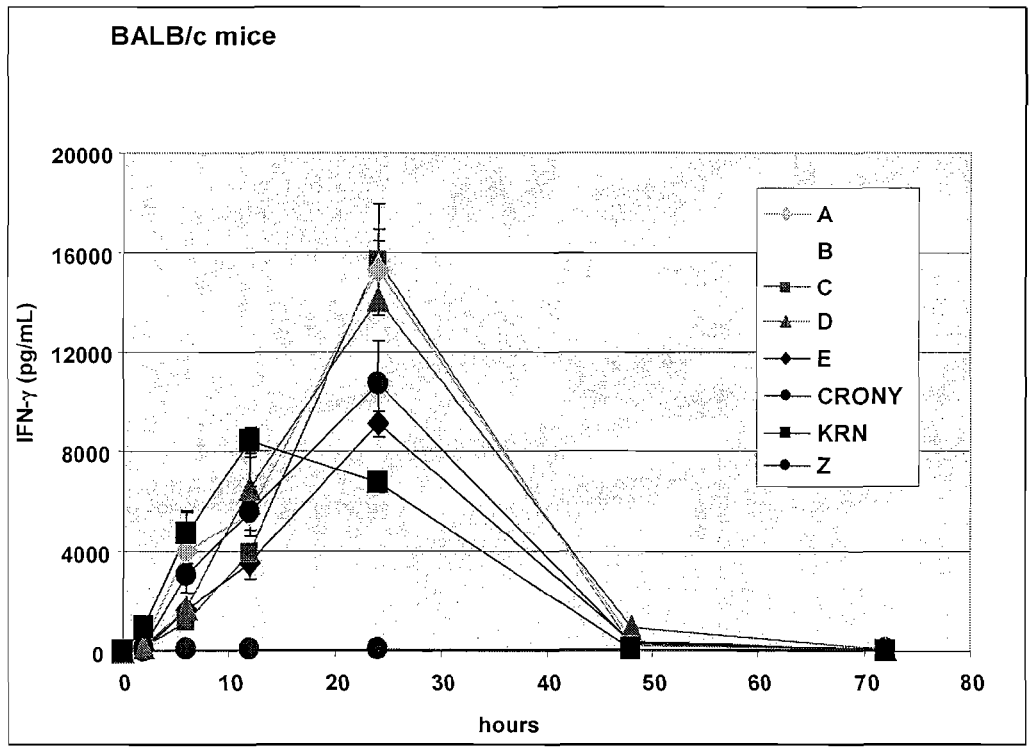
FIGS. 2A-C depict kinetic profiles of Th1-type cytokine IFN-γ that is released upon administration of the compounds of the invention or control compounds to BALB/c (FIG. 2A) and C57BL/6 (FIGS. 2B-C) mice. The compounds represented in the figures are A=compound (trans-A-1), B=compound (A-2), C=compound (A-3), D=compound (A-4), E=compound (A-5), Z=control (PBS alone), CRONY=α-C-GalCer, KRN=α-GalCer, GCK109 (A-1 trans-conformer), GCK151 (A-1 cis-conformer), and GCK152 [A-7]. The levels of IFN-γ in the sera were measured at 0, 2, 6, 12, 24, 48, and 72 hours after the compound administration by enzyme-linked immunosorbent assay (ELISA). The data are expressed as the average+/−standard deviation (SD) of two different dilutions of pooled sera.
Figure 2B:
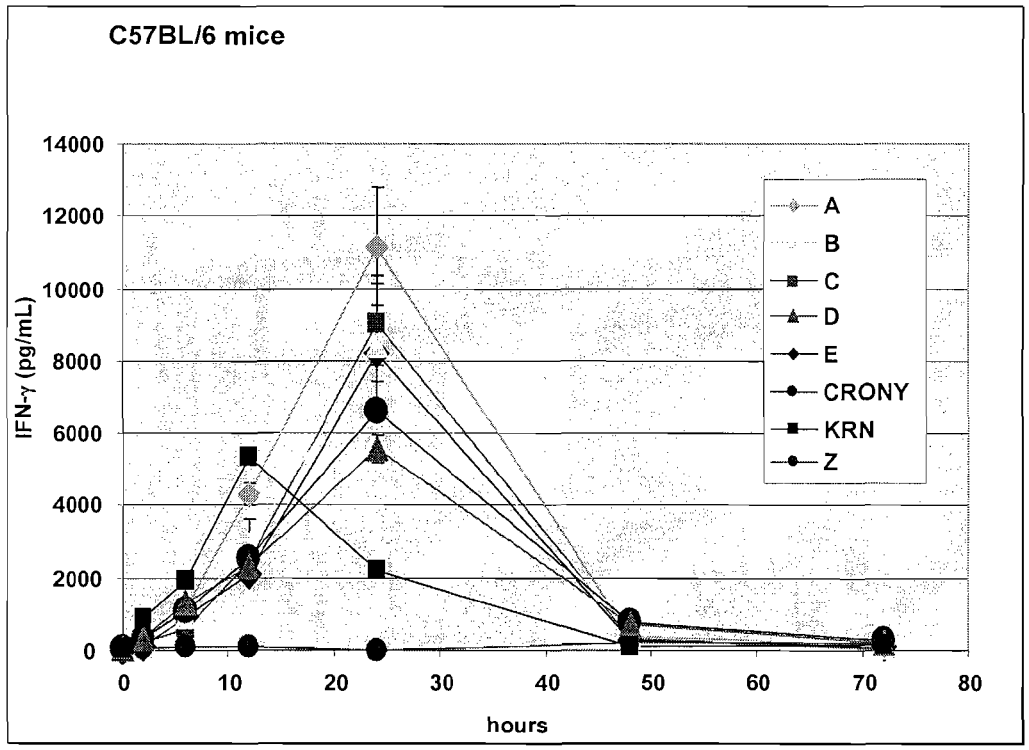
Figure 2C:
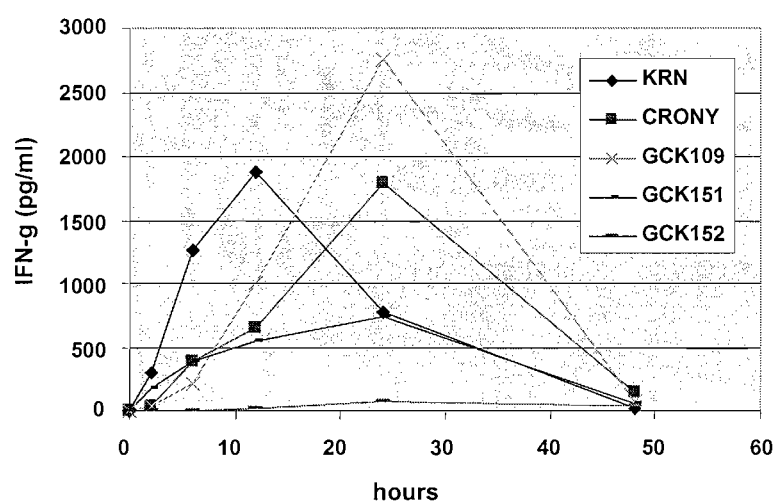
Figure 3A:
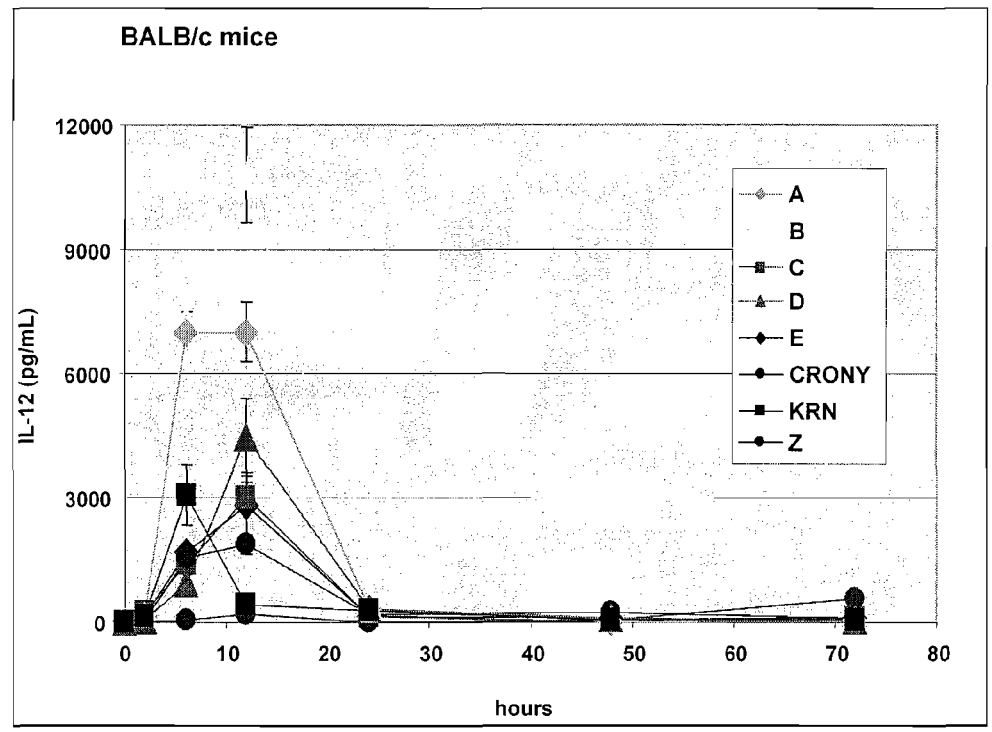
FIGS. 3A-C depict kinetic profiles of Th1-type cytokine IL-12 that is released upon administration of the compounds of the invention or control compounds to BALB/c (FIG. 3A) and C57BL/6 (FIGS. 3B-C) mice. The compounds represented in the figures are A=compound (trans-A-1), B=compound (A-2), C=compound (A-3), D=compound (A-4), E=compound (A-5), Z=control (PBS alone), CRONY=α-C-GalCer, KRN=α-GalCer, GCK109 (trans-A-1), GCK151 (cis-A-1), and GCK152 [A-7]. The levels of IL-12 in the sera were measured at 0, 2, 6, 12, 24, 48, and 72 hours after the compound administration by enzyme-linked immunosorbent assay (ELISA). The data are expressed as the average+/−SD of two different dilutions of pooled sera.
Figure 3B:
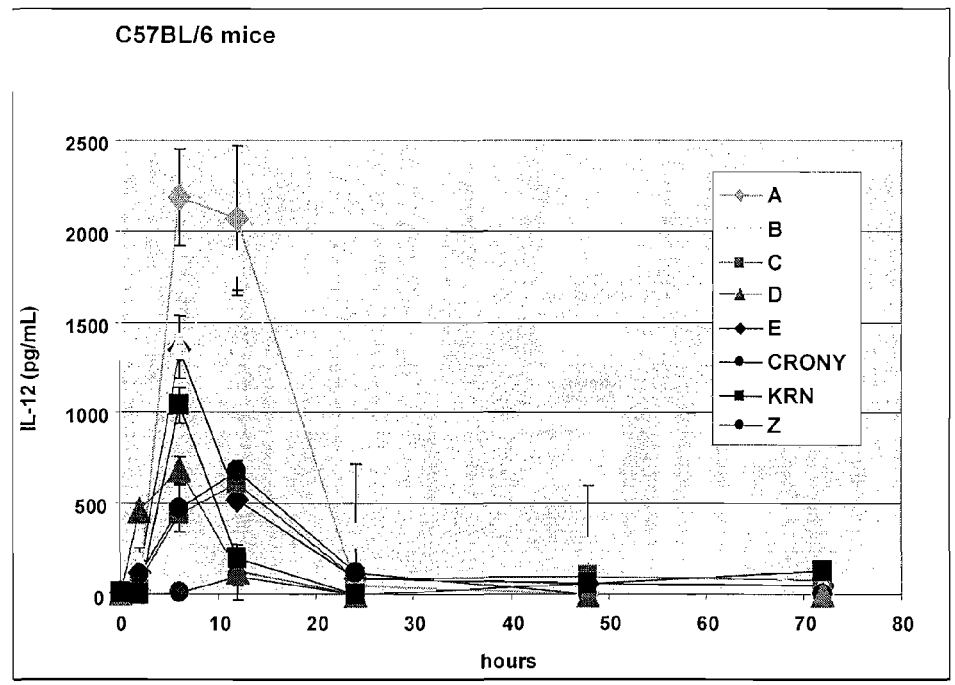
Figure 3C:
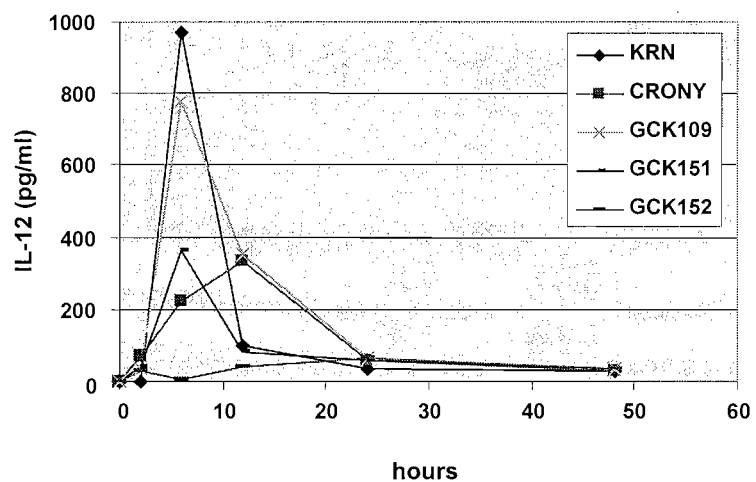

The terms "Th1-type immune response" and "Th2-type immune response" as used herein refer to immune responses mediated by Th1 and Th2 CD4+ helper T cells, respectively.

The terms "Th1-type cytokines" and "Th2-type cytokines" refer to cytokines produced by Th1 and Th2 cells, respectively. Th1-type cytokines include, but are not limited to, IFN-γ and IL-12. A non-limiting example of a Th2-type cytokine is IL-4.

The term "disease which requires a Th-1-type response for control" refers to a disease characterized by a predominantly Th2-type immune response and a Th2-type cytokine profile. Examples of such diseases include without limitation infectious viral diseases such as HIV infection, HCV infection, HBV infection, herpes virus infection, and RSV infection; cancer such as a carcinoma of the prostate or breast carcinoma; and Th2-type autoimmune diseases such as asthma and allergy.

The term "selective induction of Th1-type immune response" as used herein refers to induction and/or enhancement and/or increased duration of a Th1-type immune response which does not cause a concurrent induction and/or enhancement and/or increased duration of a Th2-type immune response. For the compounds of the present invention, selective induction of Th1-type immune response is reflected in the enhanced IL-12 secretion and increased activation of dendritic cells (as compared to compounds in the prior art), which occurs without a concurrent enhancement of IL-4 secretion.

The term "monosaccharide" refers to a sugar molecule having a chain of 3-10 carbon atoms in the form of an aldehyde (aldose) or ketone (ketose). Suitable monosaccharides contemplated for use in the invention include both naturally occurring and synthetic monosaccharides. Non-limiting examples of suitable monosaccharides include trioses, such as glycerose and dihydroxyacetone; tetroses such as erythrose and erythrulose; pentoses such as xylose, arabinose, ribose, xylulose ribulose; methyl pentoses (6-deoxyhexoses), such as rhamnose and fucose; hexoses, such as glucose, mannose, galactose, fructose and sorbose; and heptoses, such as glucoheptose, galamannoheptose, sedoheptulose and mannoheptulose. Preferred monosaccharides include, but are not limited to, hexoses.

An "effective amount" of the compound for treating a disease, e.g., a cancer, an infectious disease or an autoimmune disease, is an amount that results in measurable amelioration of at least one symptom or parameter of the disease in mammals, including humans.

As used herein, the term "pharmaceutically acceptable salts or esters thereof" refers to those salts (e.g., carboxylate salts, amino acid addition salts) and esters of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention.

The term "treat" is used herein to mean to prevent a disease or to relieve or alleviate at least one symptom of a disease in a subject. Within the meaning of the present invention, the term "treat" may also mean to prolong the prepatency, i.e., the period between infection and clinical manifestation of a disease.

The term "therapeutically effective" applied to dose or amount refers to that quantity of a compound or pharmaceutical composition that is sufficient to result in a desired activity upon administration to a mammal in need thereof.

The terms "pharmaceutically acceptable" and "physiologically acceptable" are used interchangeably, and as used in connection with compositions of the invention refer to molecular entities and other ingredients of such compositions that are physiologically tolerable and do not typically produce untoward reactions when administered to a human. Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

The term "carrier" refers to a diluent, excipient, or vehicle with which a compound of the invention is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution, saline solutions, and aqueous dextrose and glycerol solutions are preferably used as carriers, particularly for injectable solutions. Suitable pharmaceutical carriers are described in "Remington's Pharmaceutical Sciences" by E. W. Martin, 18th Edition.

The terms "adjuvant" and "immunoadjuvant" are used interchangeably herein and refer to a compound or mixture that may be non-immunogenic when administered to a host alone, but that augments the host's immune response to another antigen when administered conjointly with that antigen.

As used herein, the terms "conjoint administration", "conjointly administered", and "conjointly administering" refer to administration of two agents, such as an immune adjuvant and an antigen, simultaneously in one composition, or simultaneously in different compositions, or sequentially. For the sequential administration to be considered "conjoint," however, the antigen and adjuvant must be administered separated by a time interval that still permits the adjuvant to augment the immune response to the antigen. For example, when the antigen is a polypeptide, the antigen and adjuvant are administered on the same day, preferably within an hour of each other, and most preferably simultaneously. However, when nucleic acid is delivered to the subject and the polypeptide antigen is expressed in the subject's cells, the adjuvant is preferably administered within 24 hours of nucleic acid administration and more preferably within 6 hours.

The term "subject" as used herein refers to an animal having an immune system, preferably a mammal. The subjects to which the present invention is applicable include, but are not limited to, cows, horses, sheep, pigs, fowl (e.g., chickens), goats, cats, dogs, rodents (e.g., hamsters, mice, rats, rabbits), monkeys, primates, and humans. In a preferred embodiment, the subject is a human.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

In accordance with the present invention there may be employed conventional molecular biology, microbiology, and recombinant DNA techniques within the skill of the art. Such techniques are well-known and are explained fully in the literature. See, e.g., Sambrook, Fritsch and Maniatis, *Molecular Cloning: A Laboratory Manual*, Second Edition (1989) Cold Spring Harbor Laboratory Press, Cold Spring Harbor, N.Y. (herein "Sambrook et al., 1989"); DNA *Cloning*: A Practical Approach, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

Compounds of the Present Invention

Preferred are compounds of formula (I) where X is O, $R_5$ is H, $R_3$ is OH and $R_4$ is H.

Preferably, the compounds of the present invention have at least one nucleophilic bond in the lipid side chain (i.e., the group Q). Each nucleophilic bond is preferably an ether link (i.e., Q is —$R^1$—O—$R^2$) or a double bond (i.e., Q is alkenyl). The nucleophilic bond is preferably positioned a minimum of six carbon atoms from the terminal carbon atom of the side chain Q. For example, the double bond can be located at any position from 6 to 22 carbon atoms from the terminal carbon of the side chain Q.

According to one embodiment, Q is a $C_{23}$-$C_{32}$ alkenyl containing from 23 to 32 carbon atoms, preferably 25 to 32, more preferably 28 to 32 carbon atoms, and having one, two, or three double bonds. Preferably, Q only has one double bond. Preferably, the double bond is located between $C_7$ and $C_{12}$ (from the end of the Q group bound to the carbonyl group) and more preferably between $C_7$ and $C_{10}$ (e.g., between $C_9$ and $C_{10}$). Preferably, Q is —$C_8H_{16}$—CH=CH—$C_{18}H_{37}$. A particular family of compounds is when Q is a $C_{23}$-$C_{32}$ alkenyl and Y is —CH=CH—, preferably in the trans conformation.

In another embodiment, Q is —$R^1$—O—$R^2$. The oxygen atom can be located anywhere within the Q group, but is preferably located between $C_1$ and $C_{25}$ (from the end of the Q group bound to the carbonyl group) (e.g., between $C_1$ and $C_2$ or between $C_9$ and $C_{10}$) and more preferably between $C_{18}$ and $C_{25}$ (e.g., between $C_{19}$ and $C_{20}$). For instance, Q can be —$C_{19}H_{38}$—O—$C_6H_{13}$. A particular family of compounds is when Q is —$R^1$—O—$R^2$ and Y is —$CH_2$—$CH_2$—. In a preferred embodiment, Q is —$R^1$—O—$R^2$ and both $R^1$ and $R^2$ are alkyl groups.

In yet another embodiment, Q is —$R^1$—O—$R^2$ and at least one of $R^1$ and $R^2$ is alkenyl. The Q group preferably contains 1 to 3 double bonds and more preferably only one double bond. The double bond and the oxygen atom can be located anywhere within the Q group. Preferably, $R^1$ is alkenyl and more preferably $R^1$ is alkenyl and $R^2$ is alkyl. When the Q group contains one double bond, it preferably is located between $C_7$ and $C_{12}$ (from the end of the Q group bound to the carbonyl group), more preferably between $C_7$ and $C_{10}$, and still more preferably between $C_9$ and $C_{10}$. The oxygen atom is preferably located between $C_1$ and $C_{25}$ (from the end of the Q group bound to the carbonyl group) (e.g., between $C_1$ and $C_2$ or between $C_9$ and $C_{10}$) and more preferably between $C_{18}$ and $C_{25}$ (e.g., between $C_{19}$ and $C_{20}$). For instance, Q can be —$C_8H_{16}$—CH=CH—$C_9H_{18}$—O—$C_6H_{13}$.

According to another preferred embodiment Y is —CH=CH— and Q is $C_{27}$-$C_{32}$ alkyl, preferably $C_{27}$ or $C_{28}$ alkyl.

According to another preferred embodiment Y is —CH=CH— and Q is —$R^1$—O—$R^2$, where $R^1$ and $R^2$ are as defined above. Preferably, Q contains from 23 to 32 carbon atoms, more preferably from 25 to 32 carbon atoms, and even more preferably from 28 to 32 carbon atoms. For example, Q can be —$C_{19}H_{38}$—O—$C_6H_{13}$.

Preferred compounds of the invention include, but are not limited to:

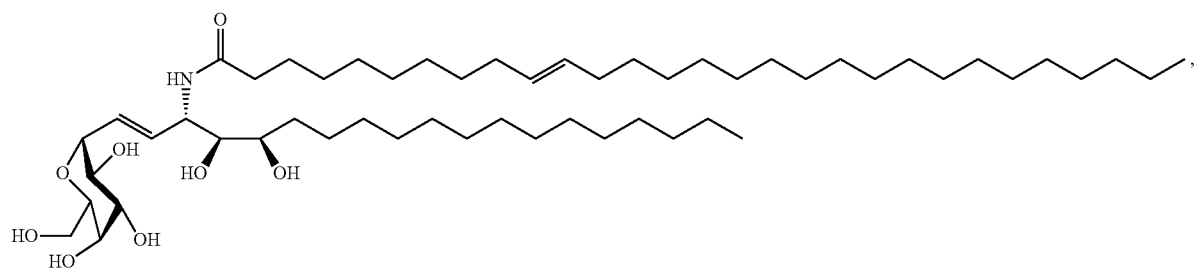

trans-(A-1)

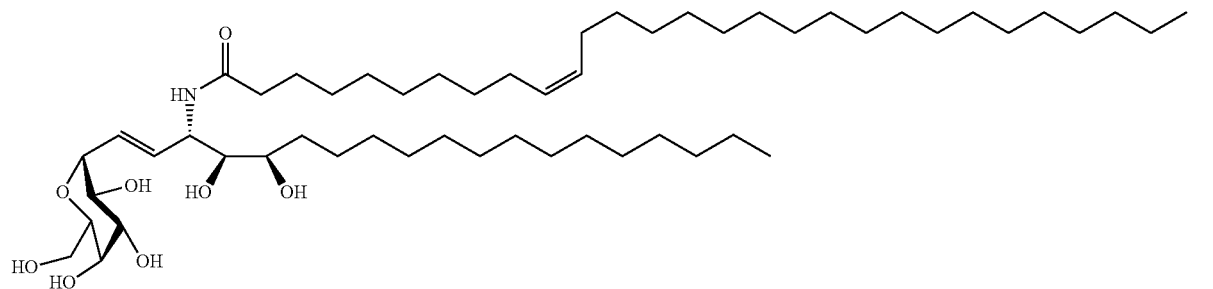

cis-(A-1)

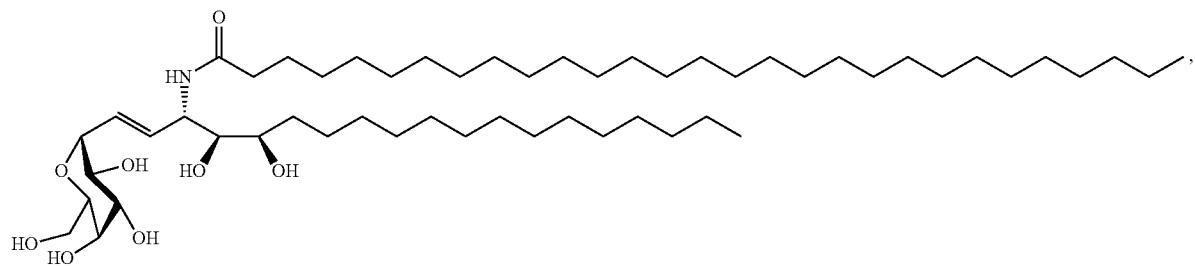

trans (A-2)

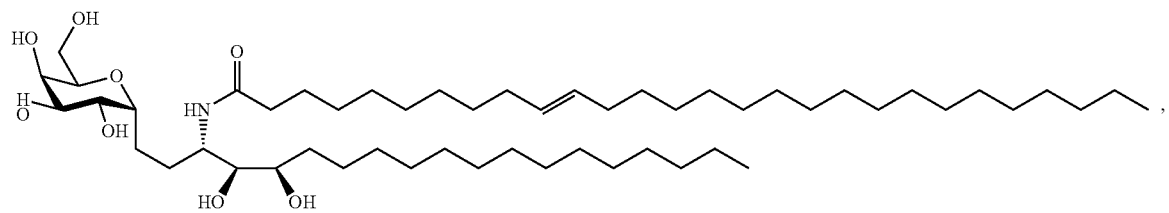

(A-3)

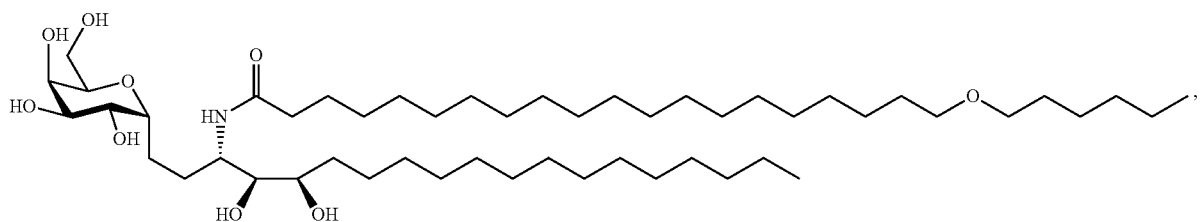

(A-4)

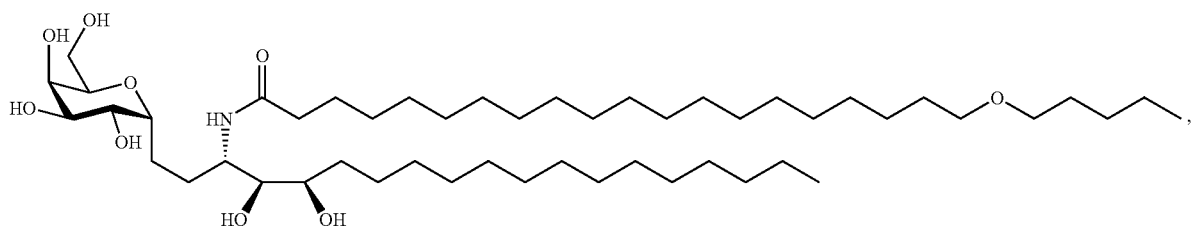

(A-5)

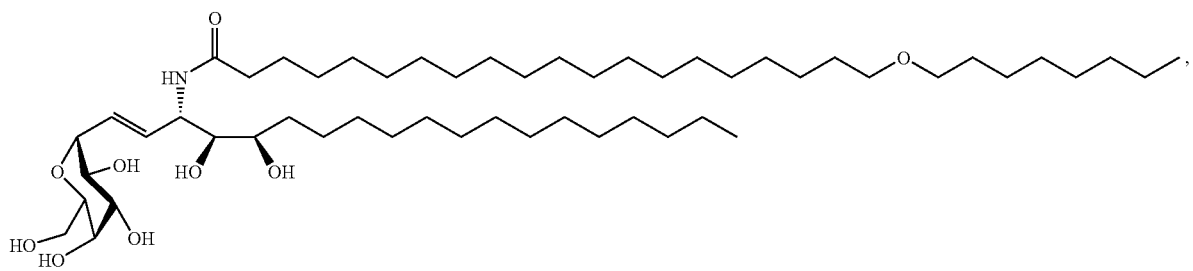

(A-6)

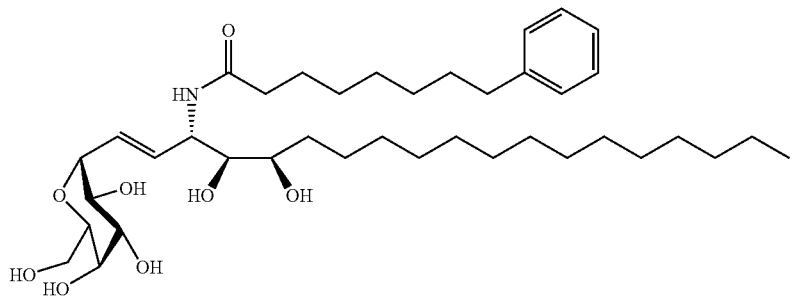

(A-7)

and pharmaceutically acceptable salts and esters thereof.

Other preferred compounds of the invention include, but are not limited to, those shown in Table B below and pharmaceutically acceptable salts and esters thereof.

TABLE B

| Structure | Q |
|---|---|
| (structure shown) | $Q = -(CH_2)_8-\overset{}{\underset{}{=}}-(CH_2)_9O(CH_2)_5CH_3$ (3S,4S,5R)-1-C-(α-D-galactopyranosyl)-3-(N-20-oxanonacos-(10,11-E)-enoylamino)-4,5-nonadecanediol |
| | $-(CH_2)_{27}CH_3$ (3S,4S,5R)-1-C-(α-D-galactopyranosyl)-3-(N-nonacosanoylamino)-4,5-nonadecanediol |
| | $-CH_2O(CH_2)_{21}(CH_3)$ (3S,4S,5R)-1-C-(α-D-galactopyranosyl)-3-(N-3-oxapentacosanoyl-amino)-4,5-nonadecanediol |
| | $-(CH_2)_9O(CH_2)_{14}CH_3$ (3S,4S,5R)-1-C-(α-D-galactopyranosyl)-3-(N-11-oxahexacosanoyl-amino)-4,5-nonadecanediol |

TABLE B-continued

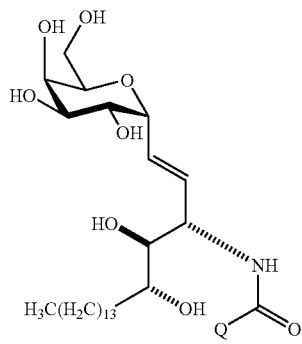

Q = —(CH$_2$)$_9$O(CH$_2$)$_{14}$CH$_3$
(3S,4S,5R)-1-C-(α-D-galactopyranosyl)-3-(N-11-oxahexacosanoyl-amino)-4,5-nonadec-(1,2-E)-enediol
—CH$_2$O(CH$_2$)$_{21}$(CH$_3$)
(3S,4S,5R)-1-C-(α-D-galactopyranosyl)-3-(N-3-oxapentacosanoyl-amino)-4,5-nonadec-(1,2-E)-enediol
—(CH$_2$)$_{19}$O(CH$_2$)$_4$CH$_3$
(3S,4S,5R)-1-C-(α-D-galactopyranosyl)-3-(N-20-oxahexacosanoyl-amino)-4,5-nonadec-(1,2-E)-enediol
—(CH$_2$)$_{19}$O(CH$_2$)$_5$CH$_3$
(3S,4S,5R)-1-C-(α-D-galactopyranosyl)-3-(N-20-oxaheptacosanoyl-amino)-4,5-nonadec-(1,2-E)-enediol

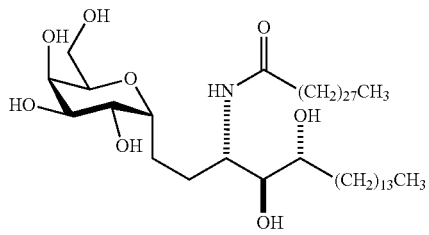

(3S,4S,5R)-1-C-(α-D-galactopyranosyl)-3-(N-20-oxanonacos-(10,11-E)-enoylamino)-4,5-nonadec-(1,2-E)-enediol
—(CH$_2$)$_{27}$CH$_3$
(3S,4S,5R)-1-C-(α-D-galactopyranosyl)-3-(N-nonacosanoylamino)-4,5-nonadec-(1,2-E)-enediol A distinct compound of the invention is a compound having the formula or a pharmaceutically acceptable salt or ester thereof.

Therapeutic Uses

The compounds of the invention are useful for treating any disease that would benefit from a selective induction of a Th1-type immune response, especially from a Th1-type immune response associated with enhanced IL-12 secretion and increased activation of antigen-presenting cells (APCs) such as dendritic cells, which occurs without a substantial concurrent enhancement of IL-4 secretion.

Without being bound by any particular theory, the inventors of the present invention believe that the compounds of the invention mediate selective induction of Th-1 immune responses by binding to the TCR of APCs, which activates NKT cells and results in the secretion of IFN-γ by the NKT cells. However, NKT cells so activated do not substantially secrete significant amounts of IL-4. The activated NKT cells further bind to antigen presenting cells (APCs) such as dendritic cells through CD40 ligand causing an enhanced local secretion of IL-12. Such local release of IL-12 allows to avoid negative effects associated with IL-12 toxicity and permits generation of a very efficient and specific Th1-type immune response, e.g. against tumors or pathogens. The inventors also believe that the compounds of the present invention act indirectly on dendritic cells and show less activity on secondary NK cell activation when compared to α-GalCer or α-C-Gal-Cer (CRONY). Non-specific activation of NK cells is thus substantially limited, which improves the safety and tolerance of the compounds of the invention over the prior art compounds.

These properties make the compound of the invention particularly useful in treating disease which requires a Th-1-type response for control.

In one embodiment, the compounds of the invention are useful for the treatment of cancer, e.g., as anti-tumor agents for inhibiting the growth of tumors, and for the treatment of cell proliferative disorders. The compounds of the invention may be used alone, or in combination with chemotherapy, radiotherapy or immunotherapy.

More specifically, the compounds of the invention are useful in the treatment of a variety of cancers including, but not limited to, carcinoma such as bladder, breast, colon, kidney, liver, lung, including small cell lung cancer, non-small cell lung cancer, esophagus, gall bladder, ovary, pancreas, testicular, stomach, renal, liver, cervix, thyroid, prostate, and skin, including squamous cell carcinoma; hematopoietic tumors of lymphoid lineage, including leukemia, acute lymphocitic leukemia, acute lymphoblastic leukemia, B cell lymphoma, T cell lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; other tumors, including melanoma, seminoma, teratocarcinoma, osteosarcoma, xenoderoma pigmentosum, keratoctanthoma, thyroid follicular cancer and Kaposi's sarcoma. In a preferred embodiment, the cancer is a solid tumor such as prostate carcinoma or breast carcinoma.

Cell proliferative disorders for which the compounds are useful include, but are not limited to, benign prostate hyperplasia, familial adenomatosis polyposis, neuro fibromatosis, psoriasis, vascular smooth cell proliferation associated with atherosclerosis, pulmonary fibrosis, arthritis glomerulonephritis, and post-surgical stenosis and restenosis.

In another embodiment, the compounds of the invention are also useful for treating infectious diseases, including both viral and non-viral infections.

For example, the compounds are useful in treating viral infections caused by retroviridae (e.g., human immunodeficiency viruses, such as HIV-1 (also referred to as HTLV-III, LAV or HTLV-III/LAV, or HIV-III)); and other isolates, such as HIV-LP; Picornaviridae (e.g., polio viruses, hepatitis A virus; enteroviruses, human coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g. influenza viruses); Bungaviridae (e.g., Hantaan viruses, bunga viruses, phleboviruses and Nairo viruses); Arena viridae (hemorrhagic fever viruses); Reoviridae (erg., reoviruses, orbiviurses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes viruses'); Poxyiridae (variola viruses, vaccinia viruses, pox viruses); and Iridoviridae (e.g. African swine fever virus); and unclassified viruses (e.g., the etiological agents of Spongiform encephalopathies, the agent of delta hepatities (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses)).

The compounds of the invention are also useful in treating bacterial infections caused by *Helicobacter pylori, Borellia burgdorferi, Legionella pneumophilia, Mycobacteria* sps (e.g. *M. tuberculosis, M. avium, M. intracellulare, M. kansaii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (*viridans* group), *Streptococcus faecalis, Streptococcus bovis, Streptococcus* (*anaerobic* sps.), *Streptococcus pneumoniae*, pathogenic *Campylobacter* sp., *Enterococcus* sp., *Pseudomonas* sp., *Pneumococcus* sp., *Chlamidia* sp., *Haemophilus influenzae, Bacillus antracis, corynebacterium diphtheriae, corynebacterium* sp., *Erysipelothrix rhusiopathiae, Clostridium perfringers, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira, Actinomyces israelii* and *Francisella tularensis*. Fungal and protozoa infections caused by *Cryptococcus neoformans, Histoplasma capsulatum, Coccidioides immitis, Blastomyces dermatitidis, Chlamydia trachomatis, Candida albicans.*

The compounds of the invention are also useful in treating infections caused by other infectious organisms such as protists including *Plasmodium* sp., *Leishmania* sp., *Schistosoma* sp. and *Toxoplasma* sp. as well as yeast and other fungi.

In a preferred embodiment, the compounds of the invention are useful for treating infections caused by a human immunodeficiency virus (HIV), hepatitis C virus (HCV), hepatitis B virus (HBV), herpes virus, respiratory syncytial virus (RSV), or malaria.

In other embodiments, the compounds of the invention are useful for treating autoimmune diseases which require a Th-1-type response for control such as asthma and allergy.

The therapeutic and prophylactic methods of the invention can be used in conjunction with other treatments. For example, an anti-cancer treatment using the compounds of the present invention can be used in combination with chemotherapy and/or radiotherapy. Anti-viral treatments using the compounds of the present invention can be used in combination with IFN-α treatment.

In conjunction with the methods of the present invention, the invention also provides pharmaceutical and vaccine compositions comprising an immunogenically effective amount of a compound of Formula (I) and, optionally, an additional immunostimulant, carrier or excipient (preferably all pharmaceutically acceptable).

Modes of Administration

Modes of administration of compounds and compositions of the invention include, but are not limited to, oral, enteral, intravenous, intramuscular, intra-tumoral, subcutaneous, transdermal, intranasal, transmucosal (including rectal and buccal), and inhalation. Preferably, an oral, transdermal, subcutaneous, or inhalation or intranasal route is used (e.g., via solid or liquid oral formulations, skin patches, or nasal sprays, respectively). In some cases, the compounds can be pulsed with syngeneic dendritic cells, followed by transferring intravenously into patients. That is, dendritic cells can be incubated with the compounds to allow the dendritic cell to bind the compound through their CD1d molecules. These compound-loaded dendritic cells can then be intravenously transferred into patients. Intravenous transfer can be either local or systemic.

Pharmaceutical Compositions

Solid dosage forms for oral administration of compounds and compositions of the invention include capsules, tablets, pills, powders, granules, and suppositories. In such solid dosage forms, the active compound of the invention can be admixed with at least one inert customary excipient (or carrier) such as sodium citrate or dicalcium phosphate; or (a) fillers or extenders, as for example, starches, lactose, sucrose, glucose, mannitol, and silicic acid; (b) binders, as for example, carboxymethylcellulose, alignates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (e) solution retarders, as for example paraffin; (f) absorption accelerators, as for example, quaternary ammonium compounds; (g) wetting agents, as for example, cetyl alcohol, and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents. Such solid compositions or solid compositions that are similar to those described can be employed as fillers in soft- and hard-filled gelatin capsules using excipients such as lactose or milk, sugar as well as high molecular weight polyethyleneglycols, and the like.

Solid dosage forms such as tablets, dragees, capsules, pills, and granules can be prepared with coatings and shells, such as enteric coatings or other suitable coatings or shells. Several such coatings and/or shells are well known in the art, and can contain opacifying agents, and can also be of such composition that they release the active compound or compounds in a certain part of the intestinal tract in a delayed manner. Examples of embedding compositions which can be used are polymeric substances and waxes. The active compounds can also be used in microencapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms can contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like. If desired, the composition can also include adjuvants, such as wetting agents, emulsifying and suspending agents, sweetening, flavoring and/or perfuming agents.

The composition may include a carrier, as defined herein. Suitable carriers include macromolecules which are soluble in the circulatory system and which are physiologically acceptable, as defined herein. The carrier preferably is relatively stable in the circulatory system with an acceptable plasma half life for clearance. Such macromolecules include but are not limited to Soya lecithin, oleic acid and sorbitan trioleate, with sorbitan trioleate preferred.

Suspensions, in addition to the active compounds, can contain suspending agents, such as, ethoxylated isostearyl alcohols, polyoxyethylene sorbitol and sorbitan esters, microcrystalline cellulose, aluminum metahydroxide, bentonite, agar-agar, tragacanth, and the like. Mixtures of suspending agents can be used if desired.

Compositions for rectal administrations are preferably suppositories which can be prepared by mixing the compounds of the present invention with suitable nonirritating excipients or carriers such as cocoa butter, polyethyleneglycol, or a suppository wax which are solid at ordinary temperatures but liquid at body temperature and therefore, melt in the rectum or vaginal cavity and release the active component.

Compositions suitable for parenteral injection can comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

Dosage forms for topical administration of a compound of the invention include ointments, powders, sprays and inhalants. The active component can be admixed under suitable conditions (e.g., sterile conditions) with a physiologically acceptable carrier and any preservatives, buffers, or propellants as may be required. Ophthalmic formulations, eye ointments, powders, and solutions are also contemplated as being within the scope of this invention.

The compounds of the invention may be advantageously formulated in a form suitable for administration by inhalation or intranasally, which is particularly useful when treating asthma or allergic respiratory diseases. The selection of the particular excipients in such formulations depends on the desired dosage form, i.e. on whether a solution is to be used in drops or as a spray (aerosol) or as a suspension, ointment or gel to be applied in the nasal cavity.

An aerosol or pressurized package can be employed for this purpose. Such aerosol formulation comprises very fine liquid or solid particles carried by a propellant gas under pressure to a site of therapeutic application. When a pharmaceutical aerosol is employed in this invention, the aerosol contains the therapeutically active compound, which can be dissolved, suspended, or emulsified in a mixture of a fluid carrier and a propellant. The aerosol can be in the form of a solution, suspension, emulsion, powder, or semi-solid preparation. Aerosols employed in the present invention are intended for administration as fine, solid particles or as liquid mists via the respiratory tract of a patient. Various types of propellants known to one of skill in the art can be utilized. Examples of suitable propellants include, but is not limited to, hydrocarbons or other suitable gas. In the case of the pressurized aerosol, the dosage unit may be determined by providing a value to deliver a metered amount. The present invention can also be carried out with a nebulizer, which is an instrument that generates very fine liquid particles of substantially uniform size in a gas. Preferably, a liquid containing the compounds of the invention is dispersed as droplets. The small droplets can be carried by a current of air through an outlet tube of the nebulizer. The resulting mist penetrates into the respiratory tract of the patient.

Alternatively a powder composition containing the compounds of the invention, with or without a lubricant, carrier, or propellant, can be administered to a mammal in need of therapy. This embodiment of the invention can be carried out with a conventional device for administering a powder pharmaceutical composition by inhalation. For example, a powder mixture of the compound and a suitable powder base such as lactose or starch may be presented in unit dosage form in for example capsular or cartridges, e.g. gelatin, or blister packs, from which the powder may be administered with the aid of an inhaler.

For aerosol administration, the compounds of the invention may be in the form of micronized particles from about 1 to about 20 µm, preferably from about 3 to about 10 µm.

In a specific embodiment, the compounds of the invention are delivered by liposomes or micellar particles.

When administered parenterally, either by the intravenous, subcutaneous or intramuscular route, liposomes can provide controlled "depot" release of encapsulated drug over an extended time period, and reduce the side effects of the drug, by limiting the concentration of free drug in the bloodstream. Liposomes can alter the tissue distribution of and uptake of drugs, in a therapeutically favorable way, and can increase the convenience of therapy, by allowing less frequent drug administration.

When administered by inhalation, the liposomes can be tailored, according to lipid composition, to release an entrapped drug at a selected release rate which may vary, in half life, from a few hours to several days. Further, to the extent the drug is sequestered in the liposomes, side effects related to rapid uptake into the respiratory tract and bloodstream are reduced.

An added advantage of liposome for drug delivery to mucosal tissue is that the liposome surfaces can be modified for increased tissue stickiness, to enhance the residence time of the liposomes at the target tissue site.

Several methods for preparing liposomes with entrapped drug are known. In one method, vesicle forming lipids are deposited as a thin film on the sides of a flask, and slowly rehydrated by addition of an aqueous buffer. The drug to be entrapped may be included either in the lipid film (in the case of a lipophilic drug), or in the aqueous hydration medium (in the case of a hydrophilic drug). The liposomes that form are multilamellar vesicles (MLVs) having heterogeneous sizes between about 0.05 and 10 microns. The MLVs may be subsequently processed, typically by homogenization, sonication, or membrane extrusion, to produce smaller, more uniformly sized suspension. Liposome sizing down to about 0.2-0.4 microns is generally preferred. Liposomes in this size range can be sterilized by passage through a 0.45 micron depth filter, have less tendency to aggregate, and also may show more favorable organ distribution when administered intravenously (Gabizon). Once the liposomal formulation is prepared, it can be lyophilized, preferably using cryoprotectants, present both in the internal as well as external medium of the liposomes.

These cryoprotectants may be selected from sugars such as sucrose, trehalose, lactose, maltose, mannitol, cyclodextrin and its derivatives.

These cryoprotectants may also be polymeric such as polyethylene glycol, dextran, polyvinyl pyrrolidone, or hydroxyethyl starch.

These cryoprotectants may be used alone or as a combination.

Amino acids may further be used when freeze-drying the liposomal formulations.

The cryoprotectants are introduced into the intraliposomal aqueous layer during the preparation of empty liposomes by using these cryoprotectants dissolved in the hydration media. Externally, the cryoprotectants are introduced during the diafiltration performed after the completion of the drug loading process. The desired cryoproectant may also be introduced by the exchange of the external buffer of any liposomal suspenion formulation by diafiltration. The liposomal suspension is filled into vials and lyophilized.

Other non-liposomal formulations comprising the compound of the invention may be freeze-dried too.

Adjuvant Use

The invention further provides a method for augmenting the immunogenicity of an antigen in a mammal, which method comprises immunizing the mammal conjointly with the antigen and with an adjuvant comprising a compound of Formula I.

According to the present invention, the use of compounds of Formula I as an adjuvant results in an enhancement and/or extension of the duration of the protective immunity induced by an antigen. For example, as disclosed herein, conjoint administration of compounds of Formula I with peptides corresponding to T cell or B cell epitopes of tumor or viral antigens, or DNA constructs expressing these antigens enhances antigen-specific immune responses.

The adjuvants of Formula I can be conjointly administered with any antigen, in particular, with antigens derived from infectious agents or tumors.

As specified above, the adjuvant activity of the compounds of the invention is attributed at least in part to their ability to enhance and/or extend NKT-mediated and dendritic cell-mediated antigen-specific Th1-type T cell responses and CD8+ T cell responses.

As compared to the compounds of the prior art (including KRN7000 and CRONY 101), the ability of the compounds of the present invention to achieve a selective induction of Th1-type immune response (i.e., achieve an efficient, specific and localized activation of the NKT cell system and, in particular, enhanced IL-12 secretion and efficient and localized secondary activation of dendritic cells in the absence of enhanced IL-4 secretion), results in increased localized cytotoxicity of activated NKT cells in the absence of non-specific cytotoxicity, making the compounds of the invention very effective in enhancing immunogenicity of various tumor and infectious antigens characterized by low immunogenicity. Furthermore, the activation of NKT cells by the compounds of the present invention is dependent on a CD1d molecule, which is monomorphic among individuals (Porcelli, *Adv. Immunol.*, 59: 1-98, 1995), indicating that adjuvants of the invention can be utilized by all patients, regardless of the MHC haplotype.

According to the present invention, an antigen and an adjuvant comprising a compound of Formula (I) are conjointly administered. Modes of administration of an antigen and an adjuvant include, but are not limited to, oral, enteral, intravenous, intramuscular, intra-tumoral, subcutaneous, transdermal, intranasal, transmucosal (including rectal and buccal), and inhalation. Preferably, an oral, transdermal, subcutaneous, or inhalation or intranasal route is used (e.g., via solid or liquid oral formulations, skin patches, or nasal sprays, respectively). Intravenous transfer can be either local or systemic. Simultaneous administration of an adjuvant comprising a compound of the present invention with the antigen is preferred and generally permits the most efficient immunostimulation. If contained in two different compositions, the adjuvants and antigens of the invention are preferably administered to the same site, and preferably not more than within 1 centimeter of each other.

As the adjuvant of the invention exerts its immunostimulatory activity in combination with a plurality of different antigens, it is therefore useful for both preventive and therapeutic applications. Accordingly, in a further aspect, the invention provides a prophylactic and/or therapeutic method for treating a diseases which require a Th-1-type response for control in a mammal comprising conjointly administering to said mammal an antigen and an adjuvant comprising a compound of Formula (I). This method can be useful, e.g., for protecting against and/or treating various infections as well as for treating various neoplastic diseases.

One embodiment is a method for enhancing the immune response to a human immunodeficiency virus (HIV) infection, hepatitis C virus (HCV) infection, hepatitis B virus (HBV) infection, herpes virus infection, or respiratory syncytial virus (RSV) infection in a mammal by conjointly administering to the mammal a virus-specific antigen and an adjuvant compound of Formula (I). Another embodiment is a method for enhancing the immune response to a prostate or breast cancer in a mammal by conjointly administering to the mammal a cancer-specific antigen and an adjuvant compound of Formula (I).

The therapeutic and prophylactic methods of the invention can be used in conjunction with other treatments. For example, an anti-cancer treatment using a tumor-specific antigen and an adjuvant of the present invention can be used in combination with chemotherapy and/or radiotherapy. Antiviral vaccines comprising adjuvants of the invention can be used in combination with IFN-α treatment.

In conjunction with the methods of the present invention, the invention provides pharmaceutical and vaccine compositions comprising an immunogenically effective amount of an antigen and immunogenically effective amount of an adjuvant comprising a compound of Formula (I) and, optionally, an additional immunostimulant, carrier or excipient (preferably all pharmaceutically acceptable). Said antigen and adjuvant can be either formulated as a single composition or as two separate compositions.

The antigens used in immunogenic (e.g., vaccine) compositions of the instant invention can be derived from a eukaryotic cell (e.g., tumor or parasite as well as yeast and other fungi), bacterial cell, viral particle, or any portion thereof. In the event the material to which the immunogenic response is to be directed is poorly antigenic (e.g., a synthetic or subunit antigen), it may be additionally conjugated to a carrier molecule such as albumin or hapten, using standard covalent binding techniques, for example, with one of the several commercially available reagent kits. It may further include a specific molecular entity to induce specific targeting to APCs, such as beta subunit of shiga toxin, peptides with specific dendritic cell affinity (Haicheur N, Bismuth E, Bosset S, Adotevi O, Warnier G, Lacabanne V, Regnault A, Desaymard C, Amigorena S, Ricciardi-Castagnoli P, Goud B, Fridman W H, Johannes L, Tartour E. The B subunit of Shiga toxin fused to a tumor antigen elicits CTL and targets dendritic cells to allow MHC class I-restricted presentation of peptides derived from exogenous antigens. J. Immunol. 2000 Sep. 15; 165(6): 3301-8.), peptide with affinity to DEC-205 receptor (Sevilla et al., *J. Exp. Med.*, 2000, 192:1249-1260), an antibody against DC-SIGN (Tacken P J, de Vries I J, Gijzen K, Joosten B, Wu D, Rother R P, Faas S J, Punt C J, Torensma R, Adema G J, Figdor C G. Effective induction of naive and recall T-cell responses by targeting antigen to human dendritic cells via a humanized anti-DC-SIGN antibody. Blood. 2005 Aug. 15; 106(4):1278-85.)

Examples of preferred antigens of the present invention include (i) malaria-specific antigens such as irradiated plasmodial sporozoites or synthetic peptide antigens comprising at least one T cell and/or B cell epitope of the malarial circumsporozoite (CS) protein (see below); (ii) viral protein or peptide antigens such as those derived from influenza virus (e.g., surface glycoproteins hemagluttinin (HA) and neuraminidase (NA) [such as turkey influenza HA or an avian influenza HA); immunodeficiency virus (e.g., a feline immunodeficiency virus (FIV) antigen, a simian immunodeficiency virus (SIV) antigen, or a human immunodeficiency virus antigen (HIV) such as gp120, gp 160, p18 antigen, Gag p17/p24, Tat, Pol, Nef, and Env; herpesvirus (e.g., a glycoprotein, for instance, from feline herpesvirus, equine herpesvirus, bovine herpesvirus, pseudorabies virus, canine herpesvirus, herpes simplex virus (HSV, e.g., HSV tk, gB, gD), Marek's Disease Virus, herpesvirus of turkeys (HVT), or cytomegalovirus (CMV), or Epstein-Barr virus); hepatitis virus (e.g., Hepatitis B surface antigen (HBsAg)); (iii) bacterial antigens such as lipopolysaccharides isolated from gram-negative bacterial cell walls and *staphylococcus*-specific, *streptococcus*-specific, *pneumococcus*-specific (e.g., PspA [see PCT Publication No. WO 92/14488]), *Neisseria gonorrhea*-specific, *Borrelia*-specific (e.g., OspA, OspB, OspC antigens of *Borrelia* associated with Lyme disease such as *Borrelia burgdorferi*, *Borrelia afzelli*, and *Borrelia garinii* [see, e.g., U.S. Pat. No. 5,523,089; PCT Publication Nos. WO 90/04411, WO 91/09870, WO 93/04175, WO 96/06165, WO93/08306; PCT/US92/08697; Bergstrom et al., *Mol. Microbiol.*, 3: 479-486, 1989; Johnson et al., Infect. and Immun. 60: 1845-1853, 1992; Johnson et al., Vaccine 13: 1086-1094, 1995; The Sixth International Conference on Lyme Borreliosis: Progress on the Development of Lyme Disease Vaccine, Vaccine 13: 133-135, 1995]) (iv), and tumor-specific proteins such as ErbB receptors, Melan A [MARTI], gp100, tyrosinase, TRP-1/gp 75, and TRP-2 (in melanoma); MAGE-1 and MAGE-3 (in bladder, head and neck, and non-small cell carcinoma); HPV EG and E7 proteins (in cervical cancer); Mucin [MUC-1] (in breast, pancreas, colon, and prostate cancers); prostate-specific antigen [PSA] (in prostate cancer); carcinoembryonic antigen [CEA] (in colon, breast, and gastrointestinal cancers) and such shared tumor-specific antigens as MAGE-2, MAGE-4, MAGE-6, MAGE-10, MAGE-12, BAGE-1, CAGE-1,2,8, CAGE-3 to 7, LAGE-1, NY-ESO-1/LAGE-2, NA-88, GnTV, TRP2-INT2, and WT-1 (Willms' tumor gene).

The foregoing list of antigens are intended as exemplary, as the antigen of interest can be derived from any animal or human pathogen or tumor. With respect to DNA encoding pathogen-derived antigens of interest, attention is directed to, e.g., U.S. Pat. Nos. 4,722,848; 5,174,993; 5,338,683; 5,494, 807; 5,503,834; 5,505,941; 5,514,375; 5,529,780; U.K. Patent No. GB 2 269 820 B; and PCT Publication Nos. WO 92/22641; WO 93/03145; WO 94/16716; WO 96/3941; PCT/US94/06652. With respect to antigens derived from tumor viruses, reference is also made to Molecular Biology of Tumor Viruses, RNA Tumor Viruses, Second Edition, Edited by Weiss et al., Cold Spring Harbor Laboratory Press, 1982. For a list of additional antigens useful in the compositions of the invention see also Stedman's Medical Dictionary (24th edition, 1982).

In one embodiment, the compositions of the present invention provide protective immunity against malaria, in particular against *P. yoelii* and major human plasmodial species *P. falciparum* and *P. vivax*. These compositions comprise one or more of the following components: (i) at least one malaria-specific peptide comprising a T cell epitope capable of eliciting an anti-malarial T-cell response preferably in mammals of diverse genetic backgrounds (e.g., YNRNIVNRLLGDAL-NGKPEEK [SEQ ID NO: 1] or SYVPSAEQI [SEQ ID NO: 2] T cell epitope of *P. yoelii* CS protein [Renia et al., *J. Immunol.*, 22: 157-160, 1993; Rodrigues et al., *Int. Immunol.*, 3: 579-585, 1991] or (NVDPNANP)$_n$ [SEQ ID NO: 3] or EYLNKIQNSLSTE WSPCSVT [SEQ ID NO: 4] T cell epitope of *P. falciparum* CS protein [Nardin et al., *Science*, 246:1603, 1989; Moreno et al., *Int. Immunol.*, 3:997:1991; Moreno et al., *J. Immunol.*, 151: 489, 1993]); and/or (ii) at least one malaria-specific peptide comprising a B cell epitope (e.g., (NANP)$_3$ [SEQ ID NO: 5] B cell epitope located within the repeat region of the CS protein of *P. falciparum* [Nardin et al., *J. Exp. Med.*, 156: 20, 1982; Nardin et al., *Ann. Rev. Immunol.*, 11: 687, 1993]) capable of stimulating the production of anti-malarial (i.e., neutralizing) antibodies (e.g., directed against the sporozoite stage of the malarial organism). Preferably, the immunogenic compositions of the present invention comprise at least one B cell epitope and at least one T cell epitope. B cell epitopes preferably elicit the production of antibodies that specifically recognize and bind to the malarial circumsporozoite (CS) protein. Alternatively or in addition, the compositions of the invention may comprise B cell and/or T cell epitopes derived from, and reactive with, other malarial components, such as, for example, the *P. vivax* Erythrocyte Secreted Protein-1 or -2 (PvESP-1 or PvESP-2) (see, e.g., U.S. Pat. No. 5,874,527), *P. falciparum* sporozoite surface protein designated Thrombospondin Related Adhesion (Anonymous) protein (TRAP), also called Sporozoite Surface Protein 2 (SSP2), LSA-1, hsp70, SALSA, STARP, Hep17, MSA, RAP-1, and RAP-2. In one embodiment, the B cell epitope and T cell epitope components are incorporated into multiple antigen peptides (MAPs), forming a synthetic macromolecular polypeptide containing a high density of the epitopes. Methods for MAP synthesis are well known in the art (see, e.g., Tam, *Proc. Natl. Acad. Sci. USA*, 85: 5409, 1988; Tam, *Meth. Enzymol.*, 168: 7, 1989).

The present invention also encompasses B cell and T cell epitopes derived from other plasmodial species, including without limitation *P. malariae, P. ovale, P. reichenowi, P. knowlesi, P. cynomolgi, P. brasilianum, P. berghei*, and *P. chabaudi*. These epitopes typically comprise between 8 and 18 amino acid residues, derived from a plasmodial protein.

In another specific embodiment, a preferred antigen of the invention is HIV-specific (such as T cell epitope RGPGRAFVTI [SEQ ID NO: 6] of p18 protein.

In a specific embodiment, the antigen of the invention may be presented by a recombinant virus expressing the antigen. Preferably, the virus is selected from the group consisting of a recombinant adenovirus, recombinant pox virus, and recombinant Sindbis virus.

When used as adjuvant, the compounds of the invention can be administered as part of a pharmaceutical or vaccine composition comprising an antigen or as a separate formulation, which is administered conjointly with a second composition containing an antigen. In any of these compositions the compounds of the invention can be combined with other adjuvants and/or excipients/carriers. These other adjuvants include, but are not limited to, oil-emulsion and emulsifier-based adjuvants such as complete Freund's adjuvant, incomplete Freund's adjuvant, MF59, or SAF; mineral gels such as aluminum hydroxide (alum), aluminum phosphate or calcium phosphate; microbially-derived adjuvants such as cholera toxin (CT), pertussis toxin, *Escherichia coli* heat-labile toxin (LT), mutant toxins (e.g., LTK63 or LTR72), Bacille Calmette-Guerin (BCG), *Corynebacterium parvum*, DNA CpG motifs, muramyl dipeptide, or monophosphoryl lipid A; particulate adjuvants such as immunostimulatory complexes (ISCOMs), liposomes, biodegradable microspheres, or saponins (e.g., QS-21); cytokines such as IFN-γ, IL-2, IL-12 or GM-CSF; synthetic adjuvants such as nonionic block copolymers, muramyl peptide analogues (e.g., N-acetyl-muramyl-L-threonyl-D-isoglutamine [thr-MDP], N-acetyl-nor-muramyl-L-alanyl-D-isoglutamine, N-acetylmuramyl-L-alanyl-D-isoglutaminyl-L-alanine-2-[1'-2'-dipalmitoyl-sn-glycero-3-hydroxyphosphory-loxy]-ethylamine), polyphosphazenes, or synthetic polynucleotides, and surface active substances such as lysolecithin, pluronic polyols, polyanions, peptides, hydrocarbon emulsions, or keyhole limpet hemocyanins (KLH). Preferably, these additional adjuvants are also pharmaceutically acceptable for use in humans.

Purity of the Compositions

The compounds of the present invention are preferably purified to a level of purity of at least 75%, more preferably, at least 85%, even more preferably at least 90%, and most preferably, 90%, 91%, 92%, 93%, 94%, 95%, 96%, 97%, 98% or 99%.

Effective Dosages

An effective amount for treating the diseases can easily be determined by empirical methods known to those skilled in the art, such as by establishing a matrix of dosages and frequencies of administration and comparing a group of experimental units or subjects to each point in the matrix. The exact amount to be administered to a patient will vary depending on the particular disease, the state and severity of the disease, and the physical condition of the patient. A measurable amelioration of any symptom or parameter can be determined by a physician skilled in the art or reported by the patient to the physician. Clinically significant attenuation or amelioration means perceptible to the patient and/or to the physician.

It will also be understood that the specific dosage form and dose level for any particular patient will depend on a variety of factors including the activity of the specific compound employed; the age, body weight, general health, and sex of the individual being treated; the time and route of administration; the rate of excretion; other drugs which have previously been administered; and the severity of the particular disease undergoing therapy.

The amount of the agent to be administered can range from between about 0.1 to about 500 μg/kg/administration, preferably from between about 0.5 to about 100 μg/kg/administration and most preferably from between about 1 to about 50 μg/kg/day. It will be understood that the pharmaceutical compositions of the present invention need not in themselves contain the entire amount of the agent that is effective in treating the disorder, as such effective amounts can be reached by administration of a plurality of doses of such pharmaceutical compositions.

For example, the compounds of the invention can be formulated in capsules or tablets, each preferably containing 0.06-3.00 mg of the compounds of the invention.

Toxicity and therapeutic efficacy compositions containing compounds of the invention can be determined by standard pharmaceutical procedures in experimental animals, e.g., by determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions that exhibit large therapeutic indices are preferred. While therapeutics that exhibit toxic side effects can be used (e.g., when treating severe forms of cancer or life-threatening infections), care should be taken to design a delivery system that targets such immunogenic compositions to the specific site (e.g., lymphoid tissue mediating an immune response, tumor or an organ supporting replication of the infectious agent) in order to minimize potential damage to other tissues and organs and, thereby, reduce side effects.

As specified above, data obtained from the animal studies can be used in formulating a range of dosage for use in humans. The therapeutically effective dosage of compounds of the present invention in humans lies preferably within a range of circulating concentrations that include the ED50 with little or no toxicity. The dosage can vary within this range depending upon the dosage form employed and the route of administration utilized. Ideally, a single dose should be used.

EXAMPLES

The following Examples illustrate the invention without limiting its scope.

I. Synthetic Examples

A. Preparation of Intermediates

The intermediates for forming the lipid chain —C(O)-Q can be prepared as shown in synthetic schemes 1A and 1B below.

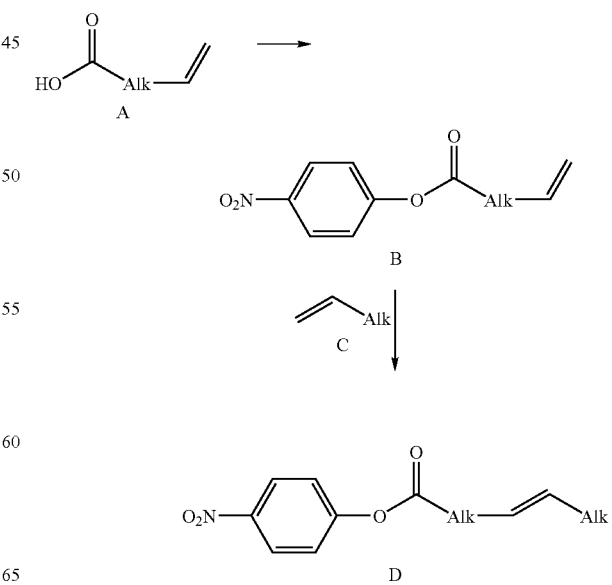

Scheme 1B

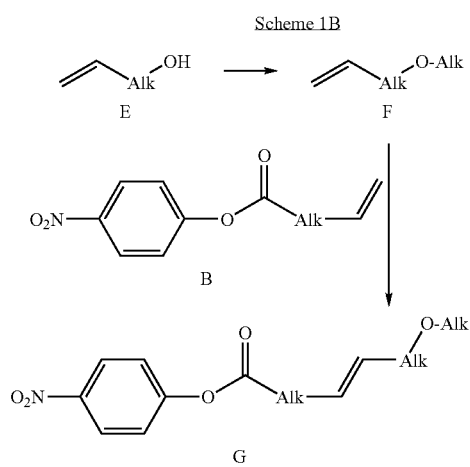

In Schemes 1A and 1B, each occurrence of Alk independently represents an alkyl chain such that the total number of carbon atoms in the fatty acid chain is from 23 to 32 carbon atoms. In Scheme 1A, the carboxylic acid (A) is converted to the paranitrophenolic ester (B) using paranitrophenol in the presence of DIC. Similarly, the alkenol (E) is converted to the alkene-ether (F) by treatment with sodium hydride and an appropriate halogenated alkane. Finally, the paranitrophenolic ester (B) is converted to the final fatty acid (D) or (G) by reacting (B) with an appropriate alkene compound in the presence of the Second Generation Grubbs Catalyst. The intermediate (D) or (G) can be purified by methods known in the art, such as by column chromatography over silica gel.

The synthesis of specific intermediates are shown in Schemes 2A-2E below.

Scheme 2A

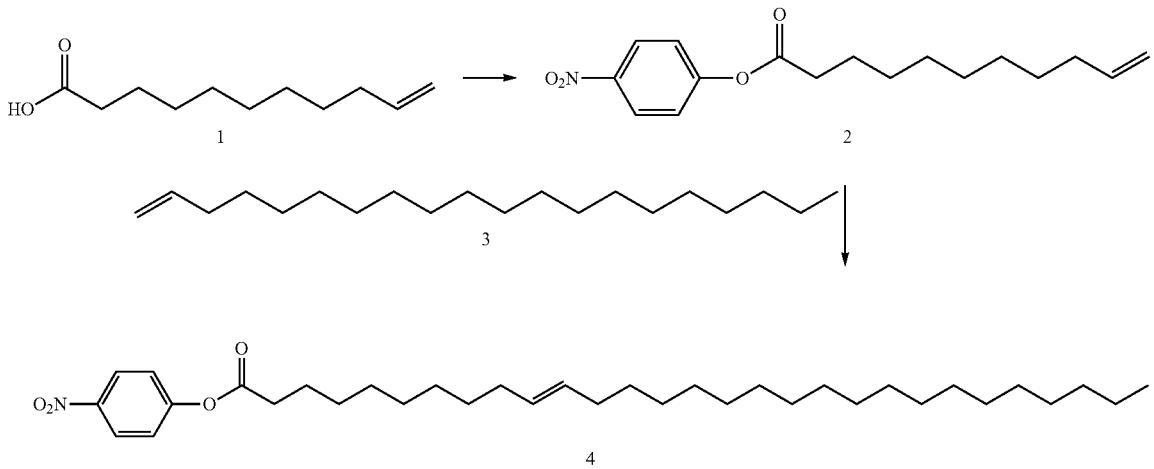

Scheme 2B

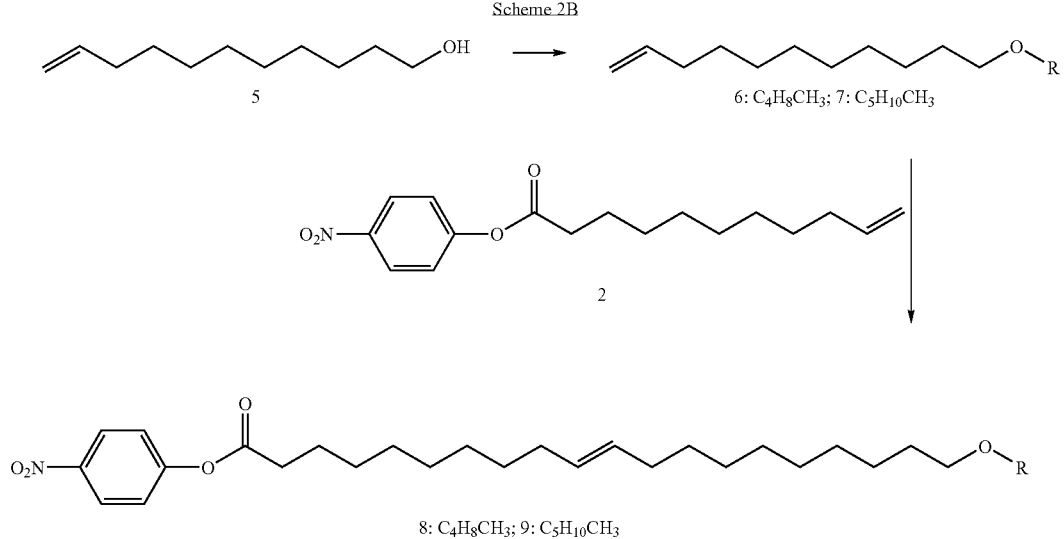

8: $C_4H_8CH_3$; 9: $C_5H_{10}CH_3$

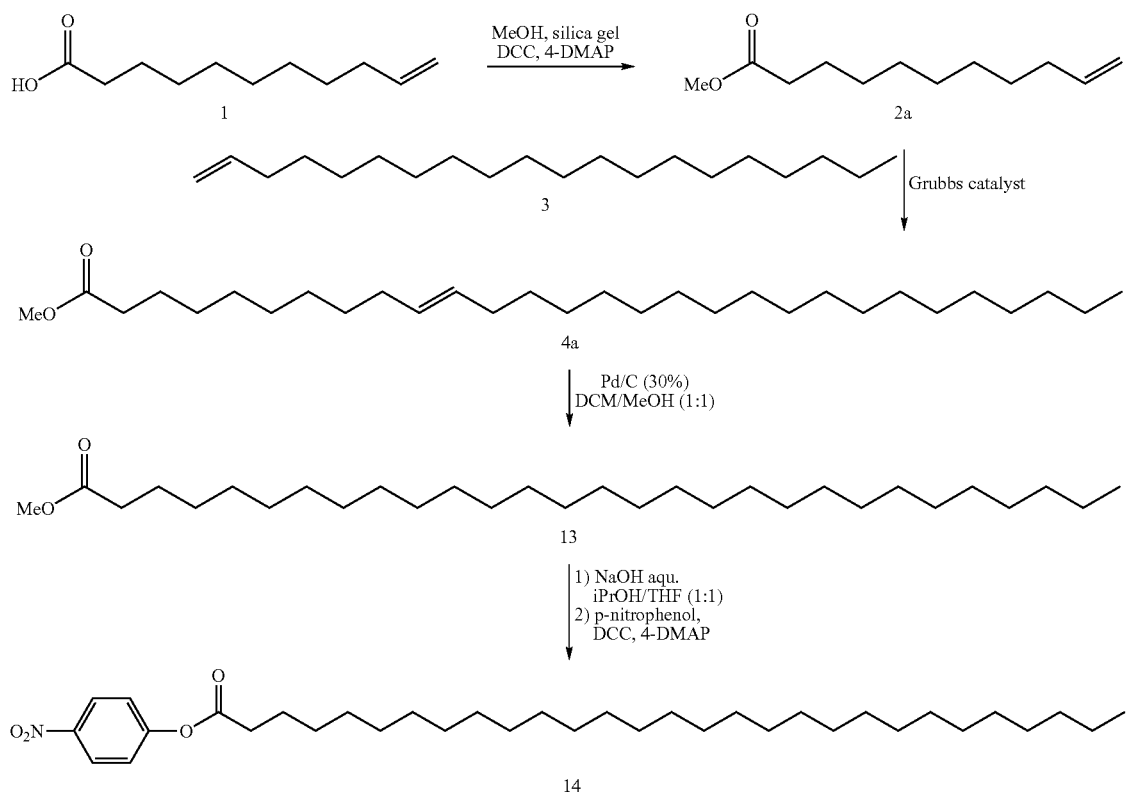
Scheme 2C
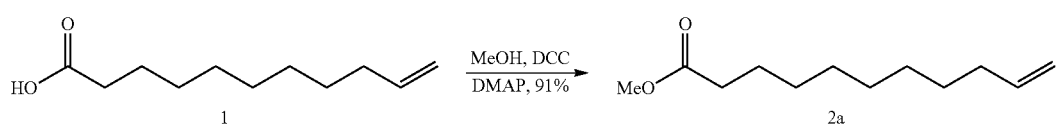
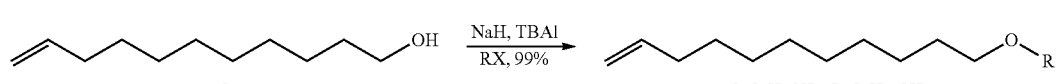
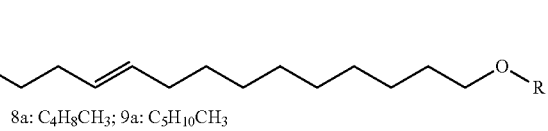
Scheme 2D
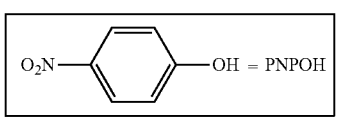

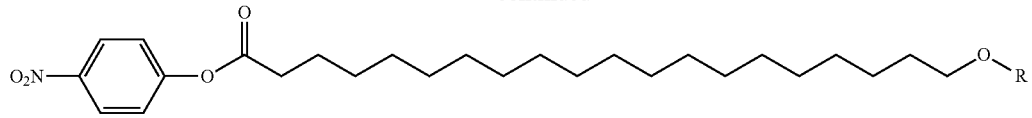

16: C$_4$H$_8$CH$_3$; 17: C$_5$H$_{10}$CH$_3$

Compound 2: To a solution of starting undecylenic acid (4.1 g, 22.2 mmol, 1.1 equiv.) in anhydrous DCM (120 ml) was added paranitrophenol (2.9 g, 20.9 mmol). In the presence of DIC (3.6 ml, 1.2 equiv.) and 4-DMAP (60 mg), the reaction mixture was stirred at rt overnight, whereupon t.l.c (PE-EA 6:1, R$_f$: 0.52) indicated the reaction was finished. The suspension was diluted with DCM and filtered through celite. The filtrate was concentrated to afford a residue. The residue was purified by flash column chromatography (Petroether-CHCl$_3$ 2:1) to provide ester 2 (6.23 g, 98%).

$^1$H NMR (300 MHz, CDCl$_3$) 8.31 (d, J=9.2 Hz, 2H), 7.32 (d, J=9.2 Hz, 2H), 5.84 (m, 1H, H-10), 5.03 (m, 2H, H-11), 2.64 (t, J=7.5 Hz, 2H, H-2), 2.09 (m, 2H, H-9), 1.80 (m, 2H, H-3), 1.48-1.35 (m, 10H, H-4-8), 3.96 (br s, 1H), 3.87 (dd, J=9.8, 2.4 Hz, 1H), 3.51 (m, 2H), 2.50 (d, J=2.1 Hz, 1H). $^{13}$C NMR (75 MHz, CDCl$_3$): 171.1, 155.5, 145.2, 139.0, 125.1, 122.3, 114.2, 34.4, 33.8, 29.3, 29.2, 29.1, 29.0, 24.9.

Compound 2a: To a solution of starting undecylenic acid in methanol is added DCC and 4-DMAP. The reaction mixture is stirred overnight at room temperature.

Compound 4: To a stirring solution of compound 2 (197 mg, 0.646 mmol) and 1-eicosene (850 mg, 4.2 equiv.) in dry CH$_2$Cl$_2$ (15 ml) was added Grubbs 2$^{nd}$ generation catalyst (65 mg, 12 mol %) and the mixture was refluxed for 1 day, whereupon t.l.c (PE-DCM 1:1, R$_f$: 0.40) indicated the consumption of the ester 2. The reaction was concentrated in vacuo and then subjected to column chromatography using silica gel (PE-DCM 2:1) to give the title compound 4 (190 mg, 53%, trans/cis: 4:1).

$^1$H NMR (500 MHz, CDCl$_3$) 8.27 (d, J=9.1 Hz, 2H), 7.28 (d, J=9.1 Hz, 2H), 5.35 (m, 2H, H-10, H-11), 2.59 (t, J=7.5 Hz, 2H, H-2), 2.02 (m, 4H, H-9, H-12), 1.76 (pent., J=7.5 Hz, 2H, H-3), 1.42-1.25 (m, 42H, H-4-8, H-13-H-28), 0.88 (t, J=6.7 Hz, 3H, H-29). $^{13}$C NMR (125 MHz, CDCl$_3$): 171.3, 155.6, 145.3, 130.5, 130.2, 125.2, 122.4, 34.3, 32.6, 32.6, 31.9, 29.7, 29.7, 29.6, 29.5, 29.4, 29.3, 29.2, 29.1, 29.0, 24.7, 22.7, 14.1.

Compound 4a: To a stirring solution of compound 2a and 1-eicosene in dry CH$_2$Cl$_2$ is added Grubbs 2$^{nd}$ generation catalyst and the mixture is refluxed for 1 day. The reaction is then concentrated in vacuo and is then subjected to column chromatography using silica gel to give the title compound 4a.

Compound 6: To a solution of ω-undecylenyl alcohol (2 ml, 98%, 9.74 mmol) in anhydrous THF (15 ml) and DMF (5 ml) was added sodium hydride (60% in mineral oil, 584 mg, 1.5 equiv.) at 0° C., in 10 minutes followed by adding TBAI (80 mg) and 1-bromopentane (1.82 ml, 1.5 equiv.). After stirring overnight under reflux, t.l.c (PE-EA 6:1) indicated the consumption of the alcohol. The mixture was diluted with DCM and quenched with water. The aqueous phase was extracted with DCM (3×), washed with saturated sodium bicarbonate and then brine. The organic phase was dried (sodium sulfate), concentrated and the residue purified by flash column chromatography (Petroether-DCM, 3:1) to provide ether 6 (2.21 g, 99%, R$_f$: 0.12 with PE-DCM 3:1). Compound 7 was produced in the same way as 6 in the yield of 94%.

6: $^1$H NMR (500 MHz, CDCl$_3$) 5.81 (m, 1H, H-10), 4.95 (m, 2H, H-11), 3.38 (t, J=7.0 Hz, 4H, H-1, H-1'), 2.03 (m, 2H, H-9), 1.56 (m, 4H, H-2, H-2'), 1.37-1.27 (m, 16H, H-3-8; H-3'-4'), 0.88 (t, J=6.9 Hz, 3H, H-5'). $^{13}$C NMR (125 MHz, CDCl$_3$): 138.9, 114.1, 71.0, 70.6, 33.8, 31.9, 29.8, 29.5, 29.4, 29.1, 28.9, 26.2, 19.4, 14.1.

Compound 8: To a stirring solution of ester 2 (190 mg, 0.623 mmol) and ether 6 (200 mg, 0,833 mmol, 1.3 equiv.) in dry chloroform (20 ml) was added Grubbs 2$^{nd}$ generation catalyst (36 mg, 7 mol %) and the mixture was refluxed for 1 day, whereupon the reaction was concentrated in vacuo and then subjected to column chromatography using silica gel (PE-DCM 3:2) to give the title compound 8 (174 mg, 84%, trans/cis: 4:1, R$_f$: 0.16 with PE-DCM 1:1). Compound 9 was produced in the same way as 8 in the yield of 81%.

8: $^1$H NMR (500 MHz, CDCl$_3$) 8.26 (d, J=9.0 Hz, 2H), 7.27 (d, J=9.1 Hz, 2H), 5.37 (m, 2H, H-10, H-11), 3.38 (t, J=6.7 Hz, 4H, H-20, H-22), 2.58 (t, J=7.5 Hz, 2H, H-2), 1.96 (m, 4H, H-9, H-12), 1.75 (pent., J=7.4 Hz, 2H, H-3), 1.56 (m, 4H, H-19, H-23), 1.39 (m, 2H, H-4), 1.32-1.25 (m, 24H, H-5-8, H-13-18, H-24-25), 0.88 (t, J=6.7 Hz, 3H, H-26). $^{13}$C NMR (125 MHz, CDCl$_3$): 171.1, 155.6, 145.3, 130.5, 130.2, 125.2, 122.4, 71.0, 34.3, 32.6, 32.7, 29.8, 29.7, 29.6, 29.5, 29.3, 29.2, 29.0, 26.2, 25.8, 24.7, 22.6, 14.1.

Compound 13: Compound 4a is dissolved in DCM/MeOH (1:1) and to the solution is added 5% Pd on carbon (30 mol %). The reaction mixture is then stirred under hydrogen until the reaction is determined to be complete by TLC analysis. The reaction is then concentrated in vacuo and is then subjected to column chromatography using silica gel to give the title compound 13.

Compound 14: Methyl ester 13 (147 mg, 0.32 mmol) was dissolved in 10 ml iPrOH/THF (1:1) and to it was added 100 mg NaOH in water (2 ml). The mixture was stirred at 60° C. for 5 h, whereupon tlc (PE/EA 12:1) indicated the hydrolysis was complete. After neutralization with 2 N HCl, the solution was directly concentrated in vacuo. To a solution of the above fatty acid residue in DCM (10 ml) was added paranitrophenol (160 mg, 0.5 mmol). In the presence of DCC (160 mg) and 4-DMAP (35 mg), the reaction mixture was stirred at rt overnight, whereupon t.l.c (PE-EA 10:1) indicated the reaction was finished. The suspension was diluted with DCM and to it was added small amount of silica gel. After evaporation, the residue was purified by flash column chromatography (PE/EA 20:1) to provide ester 14 (154 mg, 86%).

$^1$H NMR (500 MHz, CDCl$_3$) 8.27 (d, J=9.1 Hz, 2H), 7.28 (d, J=9.1 Hz, 2H), 2.59 (t, J=7.5 Hz, 2H, H-2), 1.76 (pent., J=7.5 Hz, 2H, H-3), 1.41 (pent., J=7.0 Hz, 2H, H-4), 1.37-1.22 (m, 48H, H-5 to H-28), 0.88 (t, J=7.0 Hz, 3H, H-29). $^{13}$C NMR (125 MHz, CDCl$_3$): 171.3, 155.6, 145.3, 125.2, 122.4, 34.4, 33.7, 31.9, 30.2, 29.7, 29.7, 29.6, 29.6, 29.5, 29.4, 29.4, 29.2, 29.2, 29.1, 26.7, 24.8, 22.7, 14.1.

An alternative approach to the synthesis of specific intermediates using Julia-Lythgoe-Kocienski coupling chemistry is described in Scheme 2E. Using this approach, commercially available alkylbromide 18 is reacted with commercially available benzthiazole thiol 19 to form carboxylic acid 20 after displacement of bromide. The thioether on carboxylic acid 20 is then oxidized with mCPBA to form sulfone 21. Sulfone 21 is then reacted with aldehyde 23 (which is synthesized from commercially available alcohol 22 using, for example, Swern conditions) in the presence of lithium hexamethyldisilazide under Julia-Lythgoe-Kocienski conditions. This will provide alkene carboxylic acid 24. Carboxylic acid 24 can then either be converted directly to the unsaturated p-nitrophenyl ester 4 upon treatment with p-nitrophenol in the presence of DCC and DMAP, or to the saturated p-nitrophenyl ester 15 through (1) hydrogenation with, for example 5% palladium on carbon in the presence of hydrogen, and (2) treatment of the resultant saturated acid 25 with p-nitrophenol in the presence of DCC and DMAP.

Scheme 2E

Alternative Synthesis of 4 and 14 using Julia-Lythgoe-Kocienski chemistry as the C—C bond-forming step

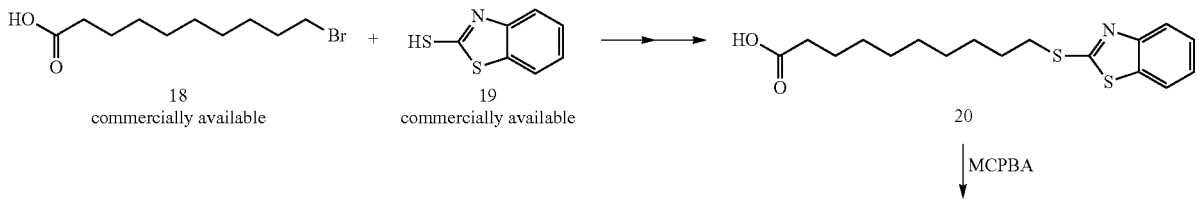

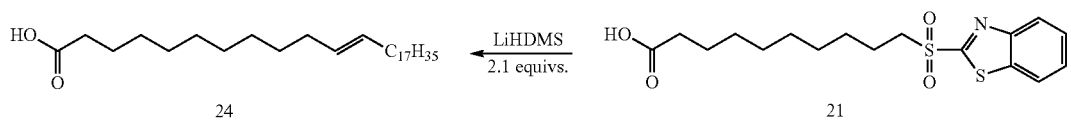

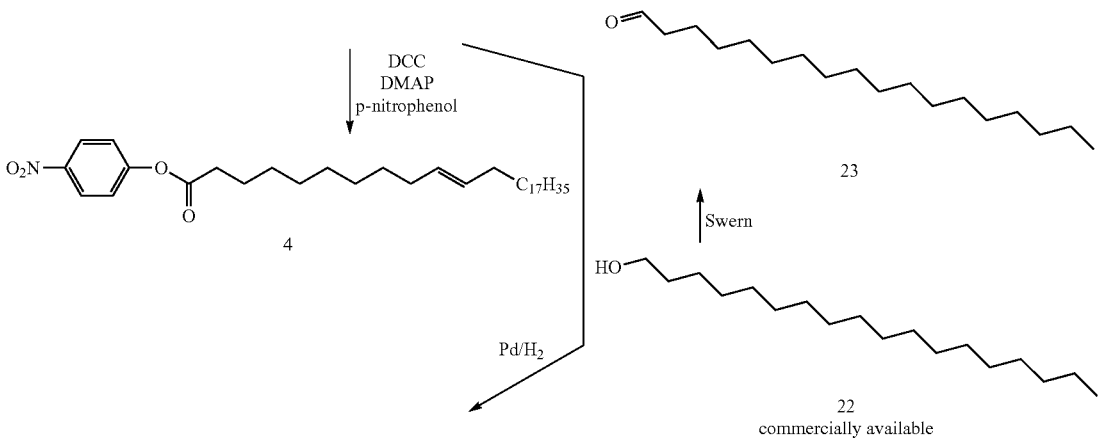

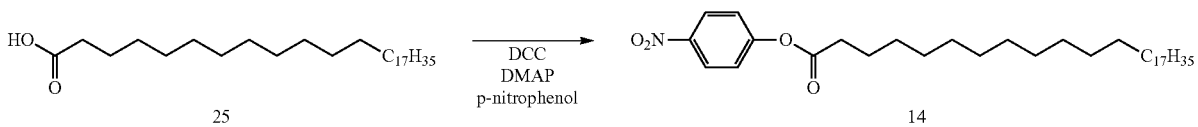

B. Preparation of Glycolipids

The glycolipids of the present invention can be prepared by the method shown in Scheme 3 below.

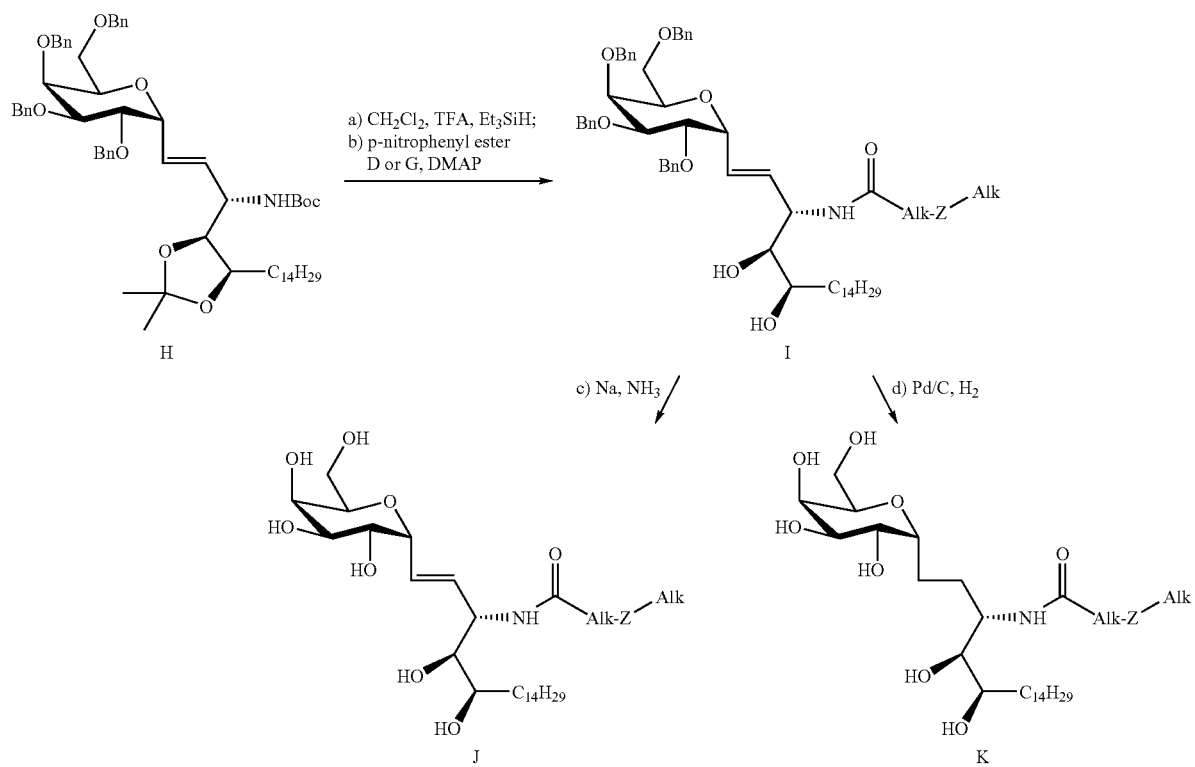

In Scheme 3, Z is —CH=CH—, O, —O-Alk-CH=CH—, or —CH=CH—O—; and each occurrence of Alk independently represents an alkyl chain such that the total number of carbon atoms in the fatty acid chain is from 23 to 32 carbon atoms. Compound (H) is deprotected (i.e., the BOC and isopropylidene protecting groups are removed), preferably by being treated with trifluoroacetic acid and triethylsilane in dicholormethane, and reacted with fatty acid ester (D) or (G) to produce compound (I). Compound (I) is then deprotected, for example, with sodium and ammonia, to produce alkene-linker compound (J) or reduced, for example, with hydrogen gas over palladium on carbon, to produce alkane-linked compound (K). The compounds can be purified by methods known in the art, such as by flash column chromatography.

Compound (H) can be prepared by using a one-pot Julia-Lythgoe-Kocienski reaction between a base labile sugar aldehyde (L) and a sulfone (M) as outlined in scheme 3a below.

Scheme 3a

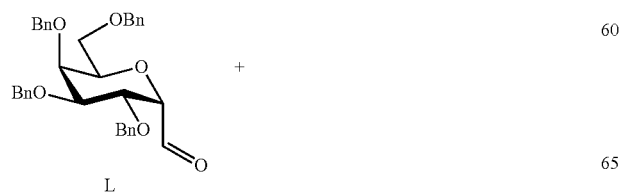

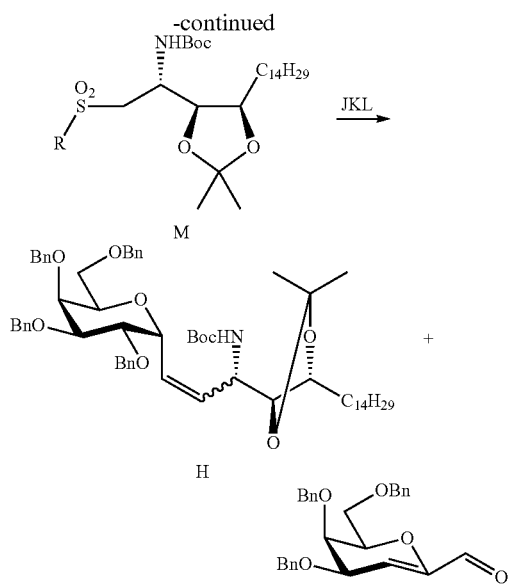

An alternate synthesis of the —CH$_2$—CH$_2$— linked analog to compound (H), compound (U) is depicted in Scheme 3b below.

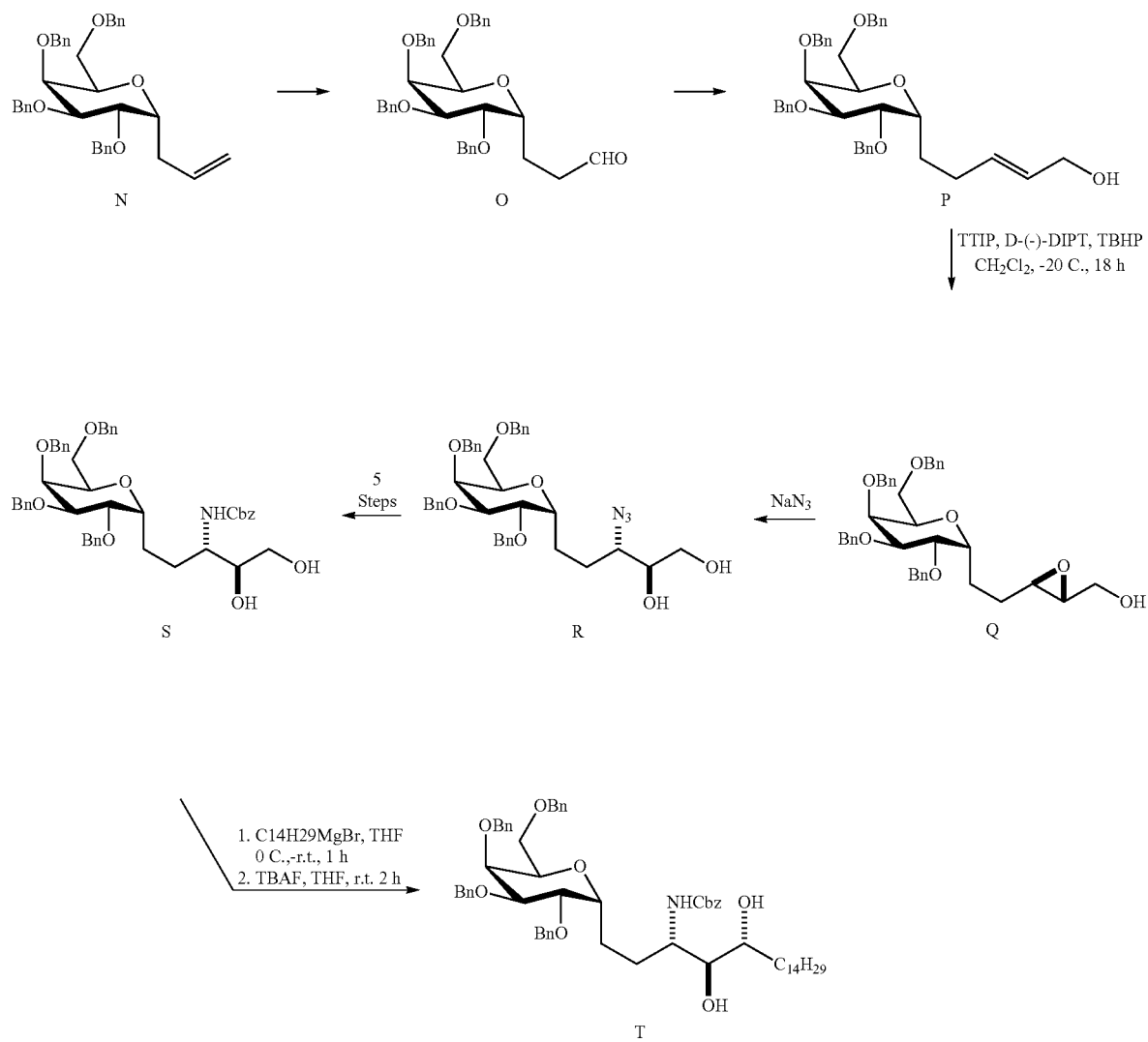

In Scheme 3b, aldehyde (O) is derived from alkene (N). Homologation via Wittig chemistry followed by reduction to the alcohol affords an allylic alcohol for treatment with well-established Sharpless epoxidation to form the epoxy (Q). Sodium azide opening with inversion leads to the protected amino hydroxy aldehyde (S). Then Grignard chemistry affords the alcohol (T).

The synthesis of specific glycolipids is shown in Scheme 4 below.

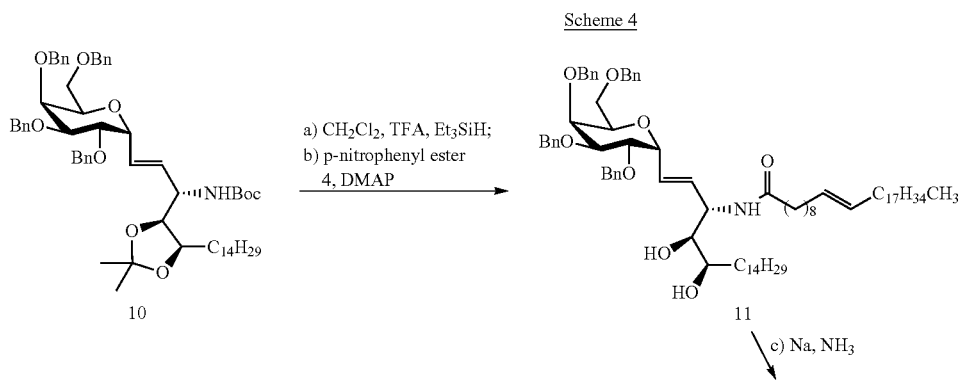

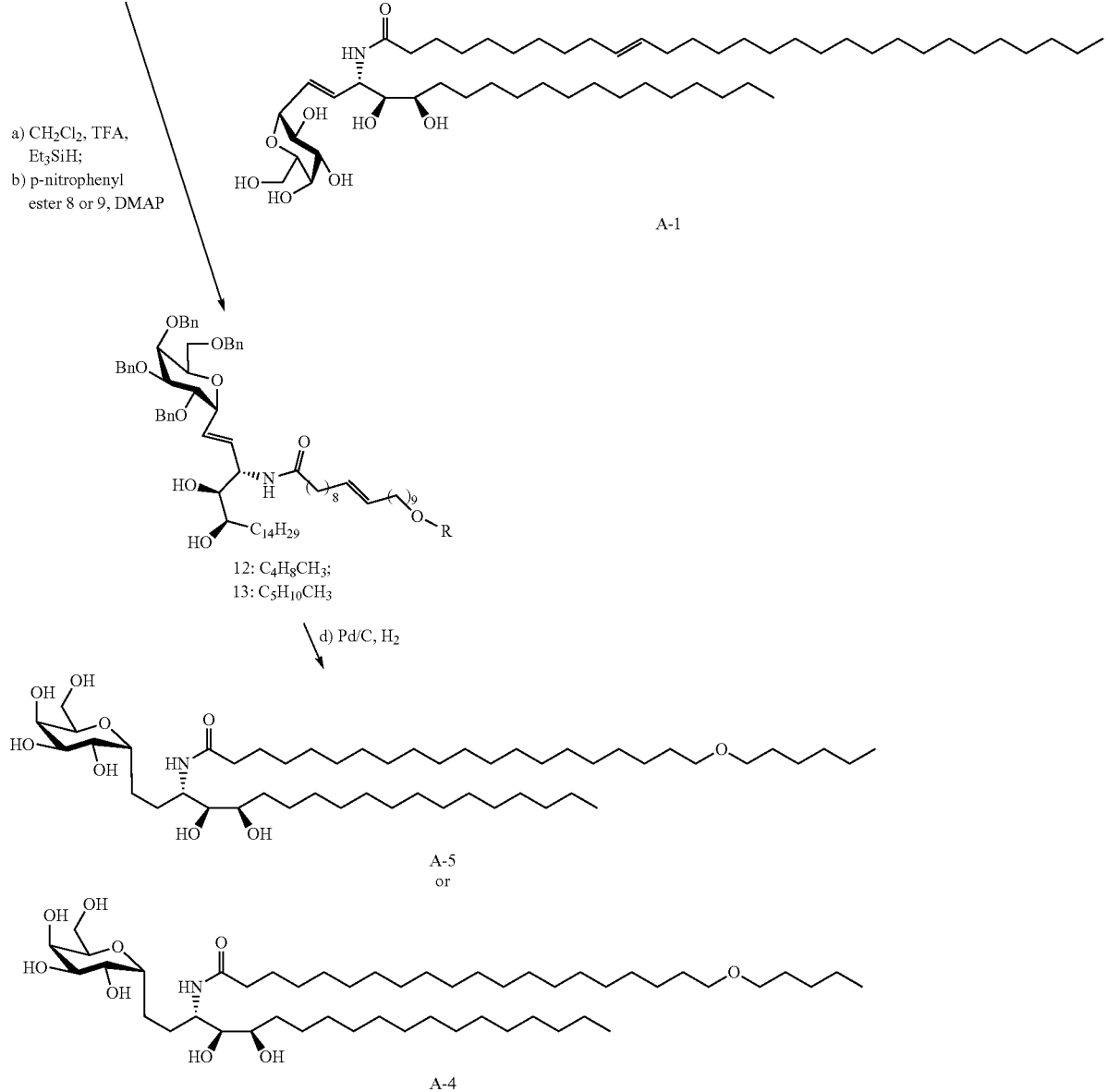

Typical procedure for amide formation: Compounds 10 (53 mg, 0.054 mmol) was dissolved in DCM (4 ml) and to it was added suitable amounts of trifluoroacetic acid (0.2 ml) and triethylsilane (0.1 ml) at 0° C. After stirred at RT for 2 h, the mixture was directly concentrated in vacuo. To the solution of the above residue in THF were added the p-nitrophenyl ester of fatty acid 4 (31 mg, 1.03 equiv.) and catalytic amount of DMAP. The mixture was then stirred at room temperature for 2 h, whereupon t.l.c (Petroether-EtOAc, 2:1) indicated the amidation was finished. The mixture was evaporated and purified by flash column chromatography (Petroether-EtOAc-CHCl$_3$, 2.5:1:0.5) afforded compounds 11 (39 mg, 58% for 2 steps).

Compound 11(E-amide chain): $^1$H NMR (500 MHz, CDCl$_3$): 7.37-7.23 (m, 20H, 4 Ph), 5.97 (dd, 1H, $J_{2,1}$=15.3 Hz, $J_{2,3}$=6.7 Hz, H-2), 5.89 (m, 2H, NH, H-1), 5.37 (s, 2H, H-10″, H-11″), 4.75 and 4.53 (2 d, 2H, J=11.9 Hz, PhCH$_2$), 4.73 (t, 1H, $J_{3,NH \text{ and } 3,2}$=7.0 Hz, H-3), 4.66 (s, 2H, PhCH$_2$), 4.65 and 4.60 (2 d, 2H, J=12.2 Hz, PhCH$_2$), 4.57 (br s, 1H, H-1′), 4.50 and 4.44 (2 d, 2H, J=11.9 Hz, PhCH$_2$), 3.99 (br s, 2H, H-2′, H-5′), 3.89 (s, 1H, H-4′), 3.69 (dd, 1-H, $J_{6'a,6'b}$=9.2 Hz, $J_{6'a,5}$=7.3 Hz, H-6′ a), 3.59 (dd, 1H, $J_{3',2'}$=8.2 Hz, $J_{3',4'}$=2.1 Hz, H-3′), 3.48 (dd, 1H, $J_{6'b}$,6′a=10.3 Hz, $J_{6'b,5}$=4.7 Hz, H-6′ b), 3.45 (br, 2H, H-4, H-5), 2.99 (d, 1H, J=7.0 Hz, OH-4), 2.16 (t, 2H, $J_{2'',3''}$=7.3 Hz, H-2″), 1.95 (br s, 4H, H-9″, H-12″), 1.79 (d, J=6.1 Hz, OH-5), 1.62 (m, 2H, 2×H-3″), 1.42-1.18 (m, 68H, 2×H-4″ to 2×H-8″, 2×H-13″ to 2×H-28″, 2×H-6 to 2×H-18), 0.88 (t, 6H, J=6.9 Hz, 3×H-19, 3×H-26″); $^{13}$C NMR (125 MHz, CDCl$_3$) 173.1, 138.4, 138.3, 138.2, 138.0, 130.4, 130.2, 129.8, 128.4, 128.3, 128.1, 127.8, 127.8, 127.7, 127.6, 127.4, 126.2, 115.6, 78.2, 76.9, 76.7, 74.5, 73.6, 73.2, 73.3, 73.1, 72.9, 68.7, 53.7, 36.8, 33.8, 32.6, 31.9, 29.7, 29.7, 29.5, 29.4, 29.2, 25.7, 25.7, 22.7, 14.1.

Compound 13 (E/Z amide chain 4:1): $^1$H NMR (500 MHz, CDCl$_3$): 7.34-7.22 (m, 20H, 4 Ph), 5.97 (dd, 1H, $J_{2,1}$=15.6 Hz, $J_{2,3}$=6.5 Hz, H-2), 5.91-5.86 (m, 2H, NH, H-1), 5.37 (s, 2H, H-10″, H-11″), 4.76 and 4.54 (2 d, 2H, J=11.6 Hz, PhCH$_2$), 4.72 (t, 1H, $J_{3,NH \text{ and } 3,2}$=7.0 Hz, H-3), 4.67 (s, 2H, PhCH$_2$), 4.65 and 4.60 (2 d, 2H, J=12.2 Hz, PhCH$_2$), 4.57 (br s, 1H, H-1'), 4.50 and 4.44 (2 d, 2H, J=11.9 Hz, PhCH$_2$), 4.00 (br s, 2H, H-2', H-5'), 3.90 (t, 1H, J=2.6 Hz, H-4'), 3.69 (dd, 1-H, J$_{6'a,6'b\ 6}$=9.9 Hz, J$_{6'a,5}$=7.4 Hz, H-6' a), 3.59 (dd, 1H, J$_{3',2'}$=8.4 Hz, J$_{3',4'}$=5.9 Hz, H-3'), 3.50 (dd, 1H, J$_{6'b,6'a}$=10.2 Hz, J$_{6'b,5}$=4.5 Hz, H-6' b), 3.46 (br, 2H, H-4, H-5), 3.39 (t, 4H, J=6.7 Hz, H-20'', H-22''), 2.98 (br s, 1H, OH-4), 2.16 (t, 2H, J$_{2'',3''}$=7.5 Hz, H-2''), 1.95 (br s, 4H, H-9'', H-12''), 1.80 (br s, OH-5), 1.62 (m, 2H, 2×H-3''), 1.56 (m, 4H, H-19'', H-23''), 1.42-1.20 (m, H, 2×H-4'' to 2×H-8'', 2×H-13'' to 2×H-18'', 2×H-24'' to 2×H-26'', 2×H-6 to 2×H-18), 0.88 (t, 6H, J=6.9 Hz, 3×H-19, 3×H-27''); $^{13}$C NMR (125 MHz, CDCl$_3$) 173.1, 138.5, 138.3, 138.2, 138.1, 130.4, 130.3, 129.8, 128.4, 128.4, 128.3, 128.3, 128.1, 127.8, 127.8, 127.7, 127.6, 127.6, 127.5, 78.2, 76.9, 76.7, 74.7, 73.76, 73.3, 73.2, 73.0, 71.0, 53.8, 36.9, 33.8, 32.6, 31.9, 31.7, 29.8, 29.8, 29.7, 29.7, 29.7, 29.6, 29.6, 29.5, 29.5, 29.4, 29.3, 29.2, 29.2, 29.2, 26.2, 25.9, 25.7, 22.7, 22.6, 14.1, 14.0.

Compound trans-(A-1): $^1$H NMR (500 MHz, pyridine-d5): δ 8.67 (d, 1H, J=8.7 Hz, NH), 6.92 (m, 2H, H-1, H-2), 6.86 (br s, 1H, 2'-OH), 6.57 (br s, 1H, 4-OH), 6.52 (br s, 1H, 3'-OH), 6.43 (br s, 1H, 6'-OH), 6.35 (br s, 1H, 4'-OH), 6.28 (br s, 1H, 5-OH), 5.93 (m, 1H, H-3), 5.53 (m, 2H, H-10'', H-11''), 5.15 (m, 1H, H-1'), 4.84 (dd, 1H, J$_{3',2'}$=9.1 Hz, J$_{1',2'}$=6.1 Hz, H-2'), 4.61 (br s, 1H, H-4'), 4.58 (t, 1H, J=6.0 Hz, H-5'), 4.37 (m, 2H, H-6a', H-6b'), 4.28 (m, 3H, H-3', H-4, H-5,), 2.45 (t, 2H, J=7.5 Hz, H-2''), 2.31 (m, 1H, H-6a), 2.06 (m, 4H, H-9'', H-12''), 1.93 (m, 2H, H-7a, H-6b), 1.83 (m, 2H, H-3''), 1.70 (m, 1H, H-7b), 1.44-1.17 (m, 62H, H-8 to H-18, H-4'' to H-8'', H-13'' to H-28''), 0.88 (t, 6H, J=6.8 Hz, 3×H-19, 3×H-29'').

A-2: $^1$H NMR (500 MHz, pyridine-d5): 8.55 (d, 1H, J=9.5 Hz, NH), 6.90 (m, 2H, H-1, H-2), 6.71 (br s, 1H, 2'-OH), 6.44 (br s, 1H, 4-OH), 6.37 (br s, 1H, 3'-OH), 6.29 (br s, 1H, 6'-OH), 6.22 (d, 1H, J=4.0 Hz, 4'-OH), 6.13 (br s, 1H, 5-OH), 5.89 (m, 1H, H-3), 5.15 (m, 1H, H-1'), 4.84 (m, 1H, H-2'), 4.60 (br s, 1H, H-4'), 4.56 (dt, 1H, J=5.9 Hz, 1.7 Hz, H-5'), 4.41 (m, 2H, H-6a', H-6b'), 4.29 (m, 3H, H-3'), 4.26 (m, 2H, H-4, H-5,), 2.45 (t, 2H, J=7.5 Hz, H-2''), 2.28 (m, 1H, H-6a), 1.93 (m, 2H, H-7a, H-6b), 1.84 (m, 2H, H-3''), 1.71 (m, 1H, H-7b), 1.46-1.17 (m, 72H, H-8 to H-18, H-4'' to H-28''), 0.89 (t, 6H, J=6.9 Hz, 3×H-19, 3×H-29''). $^{13}$C NMR (125 MHz, pyridine-d5) 175.1, 132.4, 127.8, 78.7, 76.8, 74.9, 73.1, 73.0, 71.3, 70.6, 63.0, 54.3, 37.4, 34.9, 34.5, 32.5, 30.9, 30.7, 30.5, 30.5, 30.4, 30.3, 30.3, 30.2, 30.2, 30.2, 30.0, 27.5, 26.9, 26.8, 23.3, 14.6.

A-3: MS (ES, m/z): 896.7 (M+H)$^+$; $^1$H NMR (500 MHz, pyridine-d5): 8.39 (d, 1H, J=8.8 Hz, NH), 6.61 (d, 1H, J=4.0 Hz, 2'-OH), 6.45 (d, 1H, J=4.8 Hz, 4-OH), 6.33 (m, 2H, 3'-OH, 6'-OH), 6.12 (d, 1H, J=4.1 Hz, 4'-OH), 5.94 (d, 1H, J=4.2 Hz, 5-OH), 5.53 (m, 2H, H-11'', H-12''), 5.13 (m, 1H, H-3), 4.72 (m, 1H, J$_{3',2'}$=9.3 Hz, H-2'), 4.52 (m, 3H, H-1', H-4', H-6a'), 4.36 (m, 1H, H-6b'), 4.23 (m, 4H, H-3', H-4, H-5, H-5'), 2.72 (m, 1H, H-2a), 2.58 (m, 1H, H-1a), 2.46 (m, 2H, H-2''), 2.33 (m, 2H, H-6a, H-1b), 2.31 (m, 1H, H-1b), 2.22 (m, 1H, H-2b), 2.06 (m, 4H, H-10'', H-13''), 1.94 (m, 2H, H-7a, H-6b), 1.85 (m, 2H, H-3''), 1.71 (m, 1H, H-7b), 1.48-1.17 (m, 64H, H-8 to H-18, H-4'' to H-9'', H-14'' to H-28''), 0.89 (t, 6H, J=6.8 Hz, 3×H-19, 3×H-29''); $^{13}$C NMR (125 MHz, pyridine-d5) 173.8, 131.2, 131.1, 78.9, 77.4, 74.2, 73.1, 72.6, 71.0, 70.8, 63.1, 53.1, 37.4, 34.9, 33.3, 32.5, 30.8, 30.6, 30.5, 30.4, 30.4, 30.3, 30.3, 30.2, 30.2, 30.2, 30.1, 30.0, 30.3, 29.9, 27.0, 26.9, 26.9, 23.3, 23.0, 14.6.

A-5 (and A-4): $^1$H NMR (500 MHz, pyridine-d5): δ 8.49 (d, 1H, J=9.0 Hz, NH), 6.73 (d, 1H, J=4.7 Hz, 2'-OH), 6.56 (d, 1H, J=4.7 Hz, 4-OH), 6.46 (m, 2H, 3'-OH, 6'-OH), 6.24 (d, 1H, J=4.4 Hz, 4'-OH), 6.07 (d, 1H, J=4.7 Hz, 5-OH), 5.13 (m, 1H, H-3), 4.72 (dd, 1H, J$_{3',2'}$=8.7 Hz, J$_{1',2'}$=5.5 Hz, H-2'), 4.50 (m, 3H, H-1', H-4', H-6a'), 4.36 (dd, 1H, J$_{6a',6b}$=11.3 Hz, J$_{5',6b}$=4.5 Hz, H-6b'), 4.23-4.19 (m, 4H, H-3', H-4, H-5, H-5'), 3.39 (m, 4H, H-20'', H-22''), 2.71 (m, 1H, H-2a), 2.58 (m, 1H, H-1a), 2.45 (m, 2H, H-2''), 2.30 (m, 2H, H-6a, H-1b), 2.19 (m, 1H, H-2b), 1.91 (m, 2H, H-7a, H-6b), 1.83 (m, 2H, H-3''), 1.68 (m, 1H, H-7b), 1.60 (m, 4H, H-19'', H-23''), 1.51-1.18 (m, 56H (or 58H for A-4), H-8 to H-18, H-4'' to H-18'', H-24''-H-25'' (or —H-26'' for A-4)), 0.85 (t, 6H, J=6.9 Hz, 3×H-19, 3×H-26''); $^{13}$C NMR (125 MHz, pyridine-d5) 173.8, 78.8, 77.5, 74.1, 73.0, 72.5, 71.3, 71.0, 70.7, 63.1, 53.0, 37.3, 34.8, 32.5, 32.3, 30.7, 30.6, 30.5, 30.4, 30.3, 30.2, 30.2, 30.0, 27.0, 26.9, 26.6, 23.3, 14.6.

A-6: Compound A-6 is prepared using the same procedure as described above for compound A-1, except compound 10 is reacted with compound 16 to form benzyl protected A-6. The benzyl groups are then removed with sodium in ammonia to afford the title compound A-6.

A-7: Compound A-7 is prepared using the same procedure as described above for compound A-1, except compound 10 is reacted with p-nitrophenyl-ω-phenylheptanoate to form benzyl protected A-7. The benzyl groups are then removed with sodium in ammonia to afford the title compound A-7.

p-Nitrophenyl-ω-phenylheptanoate is prepared by reacting an equimolar amount of p-nitrophenol and phenylheptanoic acid in dichloromethane in the presence of one equivalent of DCC and 5 mol % DMAP. The precipitate of dicyclohexyl urea is filtered off after the reaction is completed, and the dichloromethane removed in vacuo. The material is then quickly chromatographed on silica gel for purification.

II. Biological Examples

Example 1

Determination of Kinetic Profiles of Th1- and Th2-Type Cytokines that are Released Upon In Vivo Administration of the Compounds of the Invention Materials and Methods Tested Compounds α-GalCer (KRN7000) was synthesized by Kirin Brewery (Gumma, Japan). α-C-GalCer (CRONY 101) was synthesized as described in Schmieg J, Yang G, Franck R W, Tsuji M. 2003. Superior protection against malaria and melanoma metastases by a C-glycoside analogue of the natural killer T cell ligand α-galactosylceramide. *J Exp Med* 198: 1631-1641.

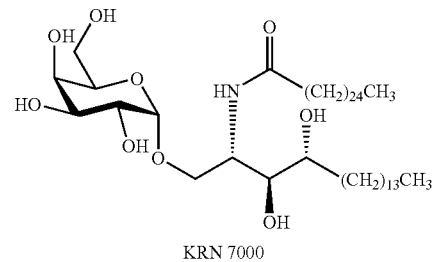

KRN 7000

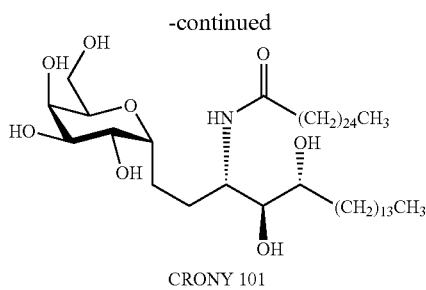

CRONY 101

The other tested synthetic C-glycolipids were synthesized as described above.

In Vivo Compound Administration

Five- to six-week-old female C57BL/6 mice and BALB/c mice were purchased from Taconic. Each glycolipid was stored at 1 mg/ml in 100% DMSO. Mice were injected intravenously with 1 μg of each glycolipid diluted in 200 μL sterile phosphate buffered saline (PBS). At indicated time points, sera were collected from each animal, and concentrations of IFN-γ, IL-4, and IL-12 in the sera were evaluated by enzyme-linked immunosorbent assay (ELISA).

Cytokine Evaluation by Enzyme-Linked Immunosorbent Assay (ELISA)

Serum concentrations of IFN-γ, IL-4, and IL-12 were evaluated using an ELISA kit (eBioscience, San Diego, Calif.). Briefly, 96 well flat-bottom ELISA plates (NUNC) were coated with capture antibody according to the manufacture's recommendation and incubated overnight at 4° C. The plates were washed with PBS+0.05% Tween 20 (PBS-T), then incubated with manufacturer provided blocking solution for 1 hr at room temperature to block non-specific binding sites. After washing with PBS-T, sera diluted 1:10 was added to the wells and incubated for 2 hrs at room temperature. Plates were then incubated at room temperature for 1 hr with biotinylated detection antibody, washed, incubated with avidin conjugated to horse radish peroxidase (HRP) for 30 min at room temperature, washed, and finally incubated with tetramethylbenzidine substrate solution in the dark for 10 minutes at room temperature. The antibodies, avidin-HRP, and substrate solution were all diluted according to the manufacture's recommendation. Reactions were stopped with 2.0N sulfuric acid and the cytokine concentration in each well was determined by comparing the absorbance at 450 nm in each well to known standards.

Results

Figure 4A:
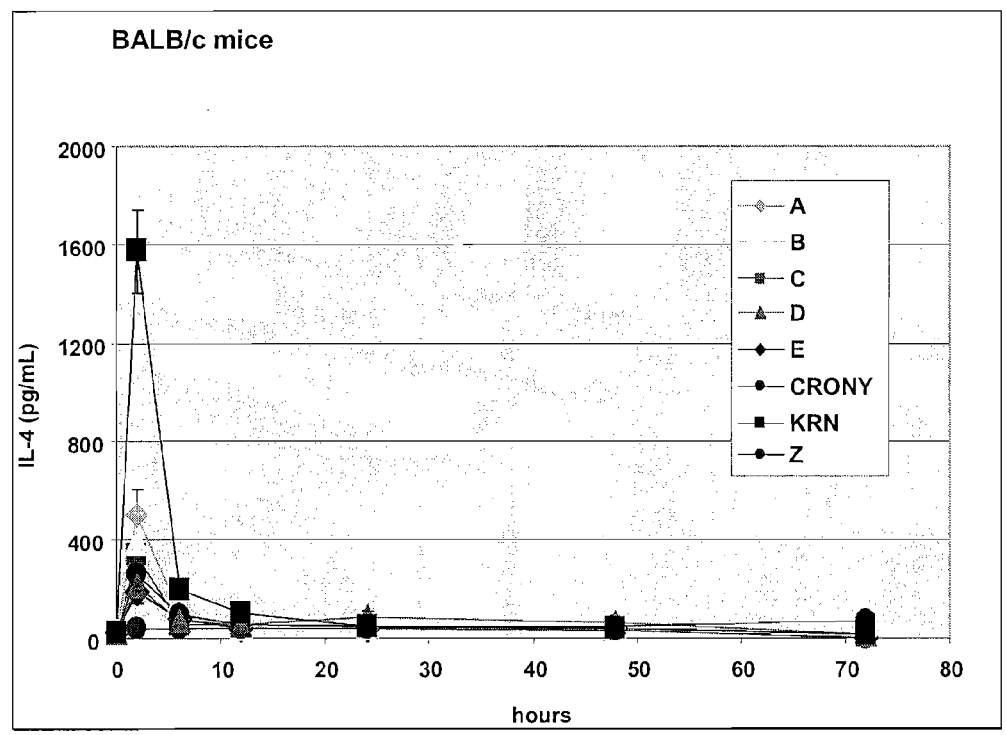
FIGS. 4A-C depict kinetic profiles of Th2-type cytokine IL-4 that is released upon administration of the compounds of the invention or control compounds to BALB/c (FIG. 4A) and C57BL/6 (FIGS. 4B-C) mice. The compounds represented in the figures are A=compound (trans-A-1), B=compound (A-2), C=compound (A-3), D=compound (A-4), E=compound (A-5), Z=control (PBS alone), CRONY=α-C-GalCer, KRN=α-GalCer, GCK109 (trans-A-1), GCK151 (cis-A-1), and GCK152 [A-7]. The levels of IL-4 in the sera were measured at 0, 2, 6, 12, 24, 48, and 72 hours after the compound administration by enzyme-linked immunosorbent assay (ELISA). The data are expressed as the average+/−SD of two different dilutions of pooled sera.
Figure 4B:
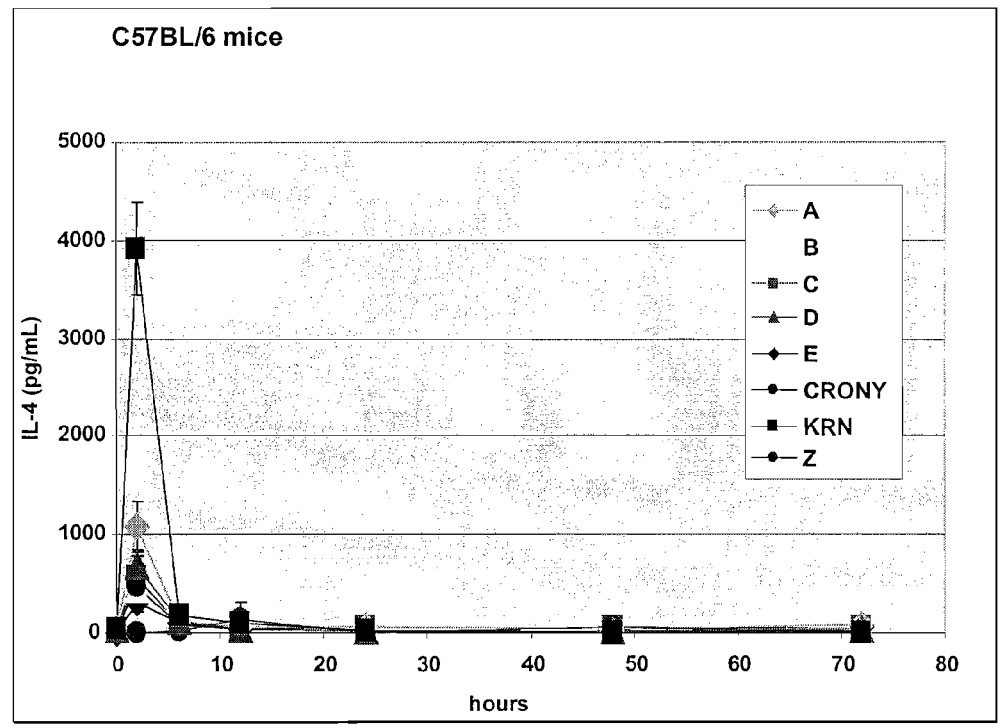
Figure 4C:
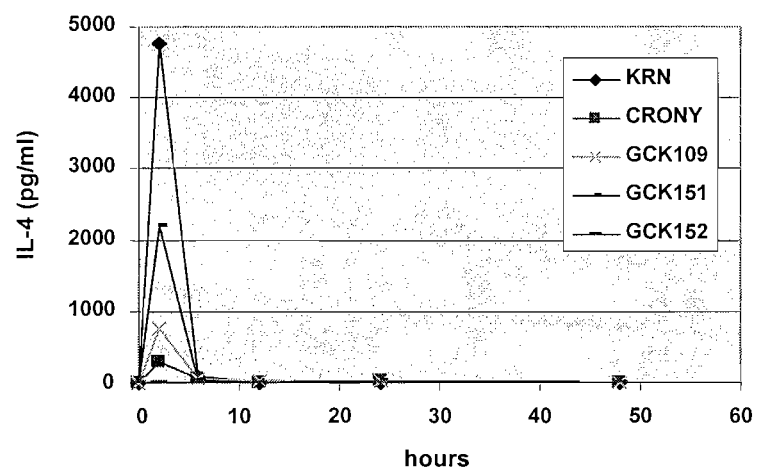

The levels of Th1- and Th2-type cytokines were determined in two different genetic backgrounds, i.e., in C57BL/6 mice and BALB/c mice. The following compounds were administered: A=compound (A-1 trans-conformer), B=compound (A-2), C=compound (A-3), D=compound (A-4), E=compound (A-5), Z=control (PBS alone), CRONY=α-C-GalCer, KRN=α-GalCer, GCK109 (A-1 trans-conformer), GCK151 (A-1 cis-conformer), GCK152 (A-7). The levels of cytokines were measured at 0, 2, 6, 12, 24, 48, and 72 hours after the compound administration. The levels of Th1-type cytokines IFN-γ and IL-12 are summarized in FIGS. 2A-C and 3A-C, respectively. The levels of Th2-type cytokine IL-4 are summarized in FIGS. 4A-C. The corresponding numerical values are also provided in Tables 1-6 below. Table 7 provides IFN-γ/IL-4 and IL-12/IL-4 ratios for various compounds, which can be used as indicators of their ability to selectively stimulate Th1-type immune responses.

As follows from the Figures and Tables, when compared to α-GalCer (KRN), several tested synthetic C-glycolipids of the invention produced (i) comparable or higher levels and extended secretion of both Th1-type cytokines IFN-γ and IL-12 and (ii) much lower levels of Th2-type cytokine IL-4. The effect was particularly pronounced in the case of compounds A-1 (trans-conformer), A-2, and A-5.

The ability of the compounds of the present invention to selectively induce high levels of IL-12 Th1-type cytokine in the absence of Th2-type cytokine induction indicates that these compounds are potent selective stimulators of Th1-type immune responses which are local and are associated with secondary activation of dendritic cells. The compounds of the present invention are therefore useful in treatment of various diseases which require a Th-1-type response for control both when used directly and when used as adjuvants.

TABLE 1

IFN-γ levels upon glycolipid administration to BALB/c mice

| compound | mouse strain | hour | test 1 | test 2 | average | SD | Total |
|---|---|---|---|---|---|---|---|
| A-5 | BALB/c | 0 | 27 | 27 | 2.5 | 0 | |
| | | 2 | 118 | 84 | 101 | 24.04163 | |
| | | 6 | 1650 | 1680 | 1665 | 21.2132 | |
| | | 12 | 4018 | 3114 | 3566 | 639.2245 | |
| | | 24 | 8738 | 9471 | 9104.5 | 518.3093 | |
| | | 48 | 453 | 398 | 425.5 | 38.89087 | |
| | | 72 | 54 | 58 | 56 | 2.828427 | 14922 |
| A-3 | BALB/c | 0 | 27 | 27 | 27 | 0 | |
| | | 2 | 137 | 189 | 163 | 36.76955 | |
| | | 6 | 1072 | 1272 | 1172 | 141.4214 | |
| | | 12 | 3891 | 3986 | 3938.5 | 67.17514 | |
| | | 24 | 14100 | 17300 | 15700 | 2262.742 | |
| | | 48 | 231 | 218 | 224.5 | 9.192388 | |
| | | 72 | 62 | 60 | 61 | 1.414214 | 21287 |
| A-2 | BALB/c | 0 | 27 | 27 | 27 | 0 | |
| | | 2 | 197 | 271 | 234 | 52.3259 | |
| | | 6 | 3723 | 4648 | 4185.5 | 654.0738 | |
| | | 12 | 7529 | 5308 | 6418.5 | 1570.484 | |
| | | 24 | 16500 | 14500 | 15500 | 1414.214 | |
| | | 48 | 319 | 332 | 325.5 | 9.192388 | |
| | | 72 | 59 | 66 | 62.5 | 4.949747 | 26755 |
| A-1 | BALB/c | 0 | 27 | 27 | 27 | 0 | |
| | | 2 | 373 | 233 | 303 | 98.99495 | |
| | | 6 | 2814 | 5167 | 3990.5 | 1663.822 | |
| | | 12 | 4881 | 6147 | 5514 | 895.1972 | |

TABLE 1-continued

IFN-γ levels upon glycolipid administration to BALB/c mice

| compound | mouse strain | hour | test 1 | test 2 | average | SD | Total |
|---|---|---|---|---|---|---|---|
| | | 24 | 16100 | 14400 | 15250 | 1202.082 | |
| | | 48 | 441 | 528 | 484.5 | 61.51829 | |
| | | 72 | 62 | 63 | 62.5 | 0.707107 | 25633 |
| Z | BALB/c | 0 | 27 | 27 | 27 | 0 | |
| | | 2 | 32 | 32 | 32 | 0 | |
| | | 6 | 43 | 40 | 41.5 | 2.12132 | |
| | | 12 | 104 | 101 | 102.5 | 2.12132 | |
| | | 24 | 72 | 95 | 83.5 | 16.26346 | |
| | | 48 | 40 | 45 | 42.5 | 3.535534 | |
| | | 72 | 41 | 56 | 48.5 | 10.6066 | 380 |
| CRONY | BALB/c | 0 | 27 | 27 | 27 | 0 | |
| | | 2 | 122 | 178 | 150 | 39.59798 | |
| | | 6 | 3114 | 3037 | 3075.5 | 54.44722 | |
| | | 12 | 6314 | 4908 | 5611 | 994.1921 | |
| | | 24 | 11900 | 9460 | 10680 | 1725.341 | |
| | | 48 | 320 | 348 | 334 | 19.79899 | |
| | | 72 | 50 | 69 | 59.5 | 13.43503 | 19938 |
| A-4 | BALB/c | 0 | 27 | 27 | 27 | 0 | |
| | | 2 | 140 | 145 | 142.5 | 3.535534 | |
| | | 6 | 1778 | 1706 | 1742 | 50.91169 | |
| | | 12 | 4988 | 8039 | 6513.5 | 2157.383 | |
| | | 24 | 14000 | 14200 | 14100 | 141.4214 | |
| | | 48 | 752 | 1107 | 929.5 | 251.0229 | |
| | | 72 | 47 | 66 | 56.5 | 13.43503 | 22676 |
| KRN | BALB/c | 0 | 27 | 27 | 27 | 0 | |
| | | 2 | 841 | 1049 | 945 | 147.0782 | |
| | | 6 | 4170 | 5335 | 4752.5 | 823.7794 | |
| | | 12 | 7996 | 8791 | 8393.5 | 562.1499 | |
| | | 24 | 6497 | 6983 | 6740 | 343.6539 | |
| | | 48 | 86 | 139 | 112.5 | 37.47666 | |
| | | 72 | 36 | 36 | 36 | 0 | 21008 |

TABLE 2

IFN-γ levels upon glycolipid administration to C57BL/6 mice

| compound | mouse strain | hour | test 1 | test 2 | average | SD | Total |
|---|---|---|---|---|---|---|---|
| A-5 | C57BL/6 | 0 | 31 | 31 | 31 | 0 | |
| | | 2 | 130 | 95 | 112.5 | 24.74874 | |
| | | 6 | 930 | 928 | 929 | 1.414214 | |
| | | 12 | 2215 | 2001 | 2108 | 151.3209 | |
| | | 24 | 7680 | 8713 | 8196.5 | 730.4413 | |
| | | 48 | 249 | 341 | 295 | 65.05382 | |
| | | 72 | 101 | 103 | 102 | 1.414214 | 11775 |
| A-3 | C57BL/6 | 0 | 31 | 31 | 31 | 0 | |
| | | 2 | 185 | 241 | 213 | 39.59798 | |
| | | 6 | 542 | 670 | 606 | 90.50967 | |
| | | 12 | 2665 | 2216 | 2440.5 | 317.4909 | |
| | | 24 | 9837 | 8235 | 9036 | 1132.785 | |
| | | 48 | 382 | 306 | 344 | 53.74012 | |
| | | 72 | 75 | 84 | 79.5 | 6.363961 | 12751 |
| A-2 | C57BL/6 | 0 | 31 | 31 | 31 | 0 | |
| | | 2 | 138 | 139 | 138.5 | 0.707107 | |
| | | 6 | 955 | 934 | 944.5 | 14.84924 | |
| | | 12 | 2427 | 3437 | 2932 | 714.1778 | |
| | | 24 | 7023 | 9807 | 8415 | 1968.585 | |
| | | 48 | 424 | 504 | 464 | 56.56854 | |
| | | 72 | 87 | 114 | 100.5 | 19.09188 | 13027 |
| A-1 | C57BL/6 | 0 | 31 | 31 | 31 | 0 | |
| | | 2 | 226 | 336 | 281 | 77.78175 | |
| | | 6 | 1172 | 1123 | 1147.5 | 34.64823 | |
| | | 12 | 4093 | 4553 | 4323 | 325.2691 | |
| | | 24 | 10000 | 12300 | 11150 | 1626.346 | |
| | | 48 | 366 | 435 | 400.5 | 48.79037 | |
| | | 72 | 124 | 178 | 151 | 38.18377 | 17485 |
| Z | C57BL/6 | 0 | 31 | 31 | 31 | 0 | |
| | | 2 | 122 | 0 | 61 | 86.26703 | |
| | | 6 | 0 | 252 | 126 | 178.1909 | |
| | | 12 | 137 | 41 | 89 | 67.88225 | |
| | | 24 | 0 | 0 | 0 | 0 | |
| | | 48 | 372 | 117 | 244.5 | 180.3122 | |
| | | 72 | 436 | 0 | 218 | 308.2986 | 770 |

TABLE 2-continued

IFN-γ levels upon glycolipid administration to C57BL/6 mice

| compound | mouse strain | hour | test 1 | test 2 | average | SD | Total |
|---|---|---|---|---|---|---|---|
| CRONY | C57BL/6 | 0 | 31 | 31 | 31 | 0 | |
| | | 2 | 359 | 352 | 355.5 | 4.949747 | |
| | | 6 | 1083 | 1106 | 1094.5 | 16.26346 | |
| | | 12 | 2667 | 2358 | 2512.5 | 218.496 | |
| | | 24 | 6511 | 6668 | 6589.5 | 111.0158 | |
| | | 48 | 798 | 757 | 777.5 | 28.99138 | |
| | | 72 | 279 | 301 | 290 | 15.55635 | 11653 |
| A-4 | C57BL/6 | 0 | 31 | 31 | 31 | 0 | |
| | | 2 | 255 | 362 | 308.5 | 75.66043 | |
| | | 6 | 1381 | 1277 | 1329 | 73.53911 | |
| | | 12 | 2466 | 2205 | 2335.5 | 184.5549 | |
| | | 24 | 5291 | 5836 | 5563.5 | 385.3732 | |
| | | 48 | 581 | 903 | 742 | 227.6884 | |
| | | 72 | 245 | 196 | 220.5 | 34.64823 | 10532 |
| KRN | C57BL/6 | 0 | 31 | 31 | 31 | 0 | |
| | | 2 | 938 | 811 | 874.5 | 89.80256 | |
| | | 6 | 1811 | 2027 | 1919 | 152.7351 | |
| | | 12 | 5179 | 5526 | 5352.5 | 245.3661 | |
| | | 24 | 2214 | 2218 | 2216 | 2.828427 | |
| | | 48 | 252 | 0 | 126 | 178.1909 | |
| | | 72 | 332 | 0 | 166 | 234.7595 | 10686 |

TABLE 3

IL-12 levels upon glycolipid administration to BALB/c mice

| compound | Mouse strain | hour | test 1 | test 2 | average | SD | Total |
|---|---|---|---|---|---|---|---|
| A-5 | BALB/c | 0 | 5 | 5 | 5 | 0 | |
| | | 2 | 74 | 233 | 153.5 | 112.43 | |
| | | 6 | 1587 | 1749 | 1668 | 114.5513 | |
| | | 12 | 2246 | 3367 | 2806.5 | 792.6667 | |
| | | 24 | 110 | 172 | 141 | 43.84062 | |
| | | 48 | 0 | 194 | 97 | 137.1787 | |
| | | 72 | 153 | 0 | 76.5 | 108.1873 | 4949 |
| A-3 | BALB/c | 0 | 5 | 5 | 5 | 0 | |
| | | 2 | 362 | 118 | 240 | 172.5341 | |
| | | 6 | 1356 | 1413 | 1384.5 | 40.30509 | |
| | | 12 | 3256 | 2765 | 3010.5 | 347.1894 | |
| | | 24 | 134 | 188 | 161 | 38.18377 | |
| | | 48 | 0 | 0 | 0 | 0 | |
| | | 72 | 0 | 151 | 75.5 | 106.7731 | 4878 |
| A-2 | BALB/c | 0 | 5 | 5 | 5 | 0 | |
| | | 2 | 141 | 7 | 74 | 94.75231 | |
| | | 6 | 7080 | 7423 | 7251.5 | 242.5376 | |
| | | 12 | 11600 | 10000 | 10800 | 1131.371 | |
| | | 24 | 454 | 431 | 442.5 | 16.26346 | |
| | | 48 | 0 | 133 | 66.5 | 94.0452 | |
| | | 72 | 3 | 442 | 222.5 | 310.4199 | 18864 |
| A-1 | BALB/c | 0 | 5 | 5 | 5 | 0 | |
| | | 2 | 0 | 239 | 119.5 | 168.9985 | |
| | | 6 | 7064 | 6898 | 6981 | 117.3797 | |
| | | 12 | 7513 | 6489 | 7001 | 724.0773 | |
| | | 24 | 299 | 313 | 306 | 9.899495 | |
| | | 48 | 0 | 0 | 0 | 0 | |
| | | 72 | 0 | 97 | 48.5 | 68.58936 | 14462 |
| Z | BALB/c | 0 | 5 | 5 | 5 | 0 | |
| | | 2 | 0 | 15 | 7.5 | 10.6066 | |
| | | 6 | 129 | 0 | 64.5 | 91.21677 | |
| | | 12 | 125 | 280 | 202.5 | 109.6016 | |
| | | 24 | 19 | 0 | 9.5 | 13.43503 | |
| | | 48 | 50 | 48 | 49 | 1.414214 | |
| | | 72 | 389 | 696 | 542.5 | 217.0818 | 883 |
| CRONY | BALB/c | 0 | 5 | 5 | 5 | 0 | |
| | | 2 | 7 | 125 | 66 | 83.4386 | |
| | | 6 | 1556 | 1494 | 1525 | 43.84062 | |
| | | 12 | 1717 | 2060 | 1888.5 | 242.5376 | |
| | | 24 | 338 | 82 | 210 | 181.0193 | |
| | | 48 | 328 | 148 | 238 | 127.2792 | |
| | | 72 | 9 | 174 | 91.5 | 116.6726 | 4025 |
| A-4 | BALB/c | 0 | 5 | 5 | 5 | 0 | |
| | | 2 | 57 | 52 | 54.5 | 3.535534 | |
| | | 6 | 730 | 1099 | 914.5 | 260.9224 | |

TABLE 3-continued

IL-12 levels upon glycolipid administration to BALB/c mice

| compound | Mouse strain | hour | test 1 | test 2 | average | SD | Total |
|---|---|---|---|---|---|---|---|
| | | 12 | 3799 | 5127 | 4463 | 939.0378 | |
| | | 24 | 396 | 271 | 333.5 | 88.38835 | |
| | | 48 | 58 | 120 | 89 | 43.84062 | |
| | | 72 | 78 | 51 | 64.5 | 19.09188 | 5926 |
| KRN | BALB/c | 0 | 5 | 5 | 5 | 0 | |
| | | 2 | 69 | 179 | 124 | 77.78175 | |
| | | 6 | 2567 | 3568 | 3067.5 | 707.8139 | |
| | | 12 | 282 | 593 | 437.5 | 219.9102 | |
| | | 24 | 119 | 412 | 265.5 | 207.1823 | |
| | | 48 | 57 | 79 | 68 | 15.55635 | |
| | | 72 | 57 | 65 | 61 | 5.656854 | 4030 |

TABLE 4

IL-12 levels upon glycolipid administration to C57BL/6 mice

| compound | Mouse strain | hour | test 1 | test 2 | average | SD | Total |
|---|---|---|---|---|---|---|---|
| A-5 | C57BL/6 | 0 | 5 | 5 | 5 | 0 | |
| | | 2 | 117 | 114 | 115.5 | 2.12132 | |
| | | 6 | 1351 | 1342 | 1346.5 | 6.363961 | |
| | | 12 | 535 | 502 | 518.5 | 23.33452 | |
| | | 24 | 96 | 78 | 87 | 12.72792 | |
| | | 48 | 52 | 64 | 58 | 8.485281 | |
| | | 72 | 46 | 53 | 49.5 | 4.949747 | 2182 |
| A-3 | C57BL/6 | 0 | 5 | 5 | 5 | 0 | |
| | | 2 | 79 | 71 | 75 | 5.656854 | |
| | | 6 | 451 | 433 | 442 | 12.72792 | |
| | | 12 | 449 | 767 | 608 | 224.86 | |
| | | 24 | 77 | 102 | 89.5 | 17.67767 | |
| | | 48 | 67 | 131 | 99 | 45.25483 | |
| | | 72 | 53 | 108 | 80.5 | 38.89087 | 1400 |
| A-2 | C57BL/6 | 0 | 5 | 5 | 5 | 0 | |
| | | 2 | 178 | 145 | 161.5 | 23.33452 | |
| | | 6 | 1488 | 1239 | 1363.5 | 176.0696 | |
| | | 12 | 1692 | 1945 | 1818.5 | 178.898 | |
| | | 24 | 44 | 602 | 323 | 394.5656 | |
| | | 48 | 500 | 0 | 250 | 353.5534 | |
| | | 72 | 91 | 0 | 45.5 | 64.34672 | 3969 |
| A-1 | C57BL/6 | 0 | 5 | 5 | 5 | 0 | |
| | | 2 | 40 | 0 | 20 | 28.28427 | |
| | | 6 | 1993 | 2370 | 2181.5 | 266.5793 | |
| | | 12 | 1790 | 2352 | 2071 | 397.394 | |
| | | 24 | 30 | 78 | 54 | 33.94113 | |
| | | 48 | 0 | 0 | 0 | 0 | |
| | | 72 | 0 | 0 | 0 | 0 | 4332 |
| Z | C57BL/6 | 0 | 5 | 5 | 5 | 0 | |
| | | 2 | 0 | 0 | 0 | 0 | |
| | | 6 | 0 | 12 | 6 | 8.485281 | |
| | | 12 | 62 | 126 | 94 | 45.25483 | |
| | | 24 | 0 | 4 | 2 | 2.828427 | |
| | | 48 | 0 | 0 | 0 | 0 | |
| | | 72 | 0 | 0 | 0 | 0 | 107 |
| CRONY | C57BL/6 | 0 | 5 | 5 | 5 | 0 | |
| | | 2 | 0 | 214 | 107 | 151.3209 | |
| | | 6 | 560 | 385 | 472.5 | 123.7437 | |
| | | 12 | 630 | 721 | 675.5 | 64.34672 | |
| | | 24 | 235 | 0 | 117.5 | 166.1701 | |
| | | 48 | 0 | 0 | 0 | 0 | |
| | | 72 | 0 | 0 | 0 | 0 | 1379 |
| A-4 | C57BL/6 | 0 | 5 | 5 | 5 | 0 | |
| | | 2 | 490 | 427 | 458.5 | 44.54773 | |
| | | 6 | 740 | 631 | 685.5 | 77.07464 | |
| | | 12 | 18 | 230 | 124 | 149.9066 | |
| | | 24 | 0 | 0 | 0 | 0 | |
| | | 48 | 0 | 0 | 0 | 0 | |
| | | 72 | 0 | 0 | 0 | 0 | 1274 |
| KRN | C57BL/6 | 0 | 5 | 5 | 5 | 0 | |
| | | 2 | 0 | 0 | 0 | 0 | |
| | | 6 | 1116 | 973 | 1044.5 | 101.1163 | |
| | | 12 | 174 | 216 | 195 | 29.69848 | |
| | | 24 | 0 | 0 | 0 | 0 | |

TABLE 4-continued

IL-12 levels upon glycolipid administration to C57BL/6 mice

| compound | Mouse strain | hour | test 1 | test 2 | average | SD | Total |
|---|---|---|---|---|---|---|---|
| | | 48 | 0 | 123 | 61.5 | 86.97413 | |
| | | 72 | 101 | 164 | 132.5 | 44.54773 | 1440 |

TABLE 5

IL-4 levels upon glycolipid administration to BALB/c mice

| compound | mouse strain | hour | test 1 | test 2 | average | SD | Total |
|---|---|---|---|---|---|---|---|
| A-5 | BALB/c | 0 | 27 | 27 | 27 | 0 | |
| | | 2 | 122 | 190 | 156 | 48.08326 | |
| | | 6 | 60 | 75 | 67.5 | 10.6066 | |
| | | 12 | 48 | 43 | 45.5 | 3.535534 | |
| | | 24 | 39 | 43 | 41 | 2.828427 | |
| | | 48 | 41 | 39 | 40 | 1.414214 | |
| | | 72 | 3.4 | 3.4 | 3.4 | 0 | 382 |
| A-3 | BALB/c | 0 | 27 | 27 | 27 | 0 | |
| | | 2 | 273 | 342 | 307.5 | 48.79037 | |
| | | 6 | 56 | 53 | 54.5 | 2.12132 | |
| | | 12 | 44 | 52 | 48 | 5.656854 | |
| | | 24 | 44 | 44 | 44 | 0 | |
| | | 48 | 48 | 38 | 43 | 7.071068 | |
| | | 72 | 12.23 | 12.23 | 12.23 | 0 | 538 |
| A-2 | BALB/c | 0 | 27 | 27 | 27 | 0 | |
| | | 2 | 263 | 397 | 330 | 94.75231 | |
| | | 6 | 90 | 164 | 127 | 52.3259 | |
| | | 12 | 48 | 51 | 49.5 | 2.12132 | |
| | | 24 | 43 | 48 | 45.5 | 3.535534 | |
| | | 48 | 42 | 39 | 40.5 | 2.12132 | |
| | | 72 | 2 | 2 | 2 | 0 | 623 |
| A-1 | BALB/c | 0 | 27 | 27 | 27 | 0 | |
| | | 2 | 358 | 505 | 431.5 | 103.9447 | |
| | | 6 | 85 | 106 | 95.5 | 14.84924 | |
| | | 12 | 52 | 50 | 51 | 1.414214 | |
| | | 24 | 40 | 43 | 41.5 | 2.12132 | |
| | | 48 | 46 | 42 | 44 | 2.828427 | |
| | | 72 | 4 | 4 | 4 | 0 | 696 |
| Z | BALB/c | 0 | 27 | 27 | 27 | 0 | |
| | | 2 | 36 | 39 | 37.5 | 2.12132 | |
| | | 6 | 41 | 40 | 40.5 | 0.707107 | |
| | | 12 | 56 | 36 | 46 | 14.14214 | |
| | | 24 | 50 | 37 | 43.5 | 9.192388 | |
| | | 48 | 37 | 34 | 35.5 | 2.12132 | |
| | | 72 | 0 | 0 | 0 | 0 | 232 |
| CRONY | BALB/c | 0 | 27 | 27 | 27 | 0 | |
| | | 2 | 264 | 261 | 262.5 | 2.12132 | |
| | | 6 | 80 | 94 | 87 | 9.899495 | |
| | | 12 | 45 | 53 | 49 | 5.656854 | |
| | | 24 | 49 | 46 | 47.5 | 2.12132 | |
| | | 48 | 45 | 48 | 46.5 | 2.12132 | |
| | | 72 | 67 | 67 | 67 | 0 | 588 |
| A-4 | BALB/c | 0 | 27 | 27 | 27 | 0 | |
| | | 2 | 200 | 214 | 207 | 9.899495 | |
| | | 6 | 85 | 74 | 79.5 | 7.778175 | |
| | | 12 | 64 | 52 | 58 | 8.485281 | |
| | | 24 | 50 | 85 | 67.5 | 24.74874 | |
| | | 48 | 52 | 66 | 59 | 9.899495 | |
| | | 72 | 12 | 12 | 12 | 0 | 511 |
| KRN | BALB/c | 0 | 27 | 27 | 27 | 0 | |
| | | 2 | 1809 | 1571 | 1690 | 168.2914 | |
| | | 6 | 214 | 194 | 204 | 14.14214 | |
| | | 12 | 78 | 100 | 89 | 15.55635 | |
| | | 24 | 51 | 50 | 50.5 | 0.707107 | |
| | | 48 | 46 | 42 | 44 | 2.828427 | |
| | | 72 | 12 | 12 | 12 | 0 | 2117 |

TABLE 6

IL-4 levels upon glycolipid administration to C57BL/6 mice

| compound | mouse strain | hour | test 1 | test 2 | average | SD | Total |
|---|---|---|---|---|---|---|---|
| A-5 | C57BL/6 | 0 | 46 | 46 | 46 | 0 | |
| | | 2 | 283 | 333 | 308 | 35.35534 | |
| | | 6 | 75 | 103 | 89 | 19.79899 | |
| | | 12 | 42 | 48 | 45 | 4.242641 | |
| | | 24 | 46 | 54 | 50 | 5.656854 | |
| | | 48 | 44 | 48 | 46 | 2.828427 | |
| | | 72 | 69 | 60 | 64.5 | 6.363961 | 649 |
| A-3 | C57BL/6 | 0 | 46 | 46 | 46 | 0 | |
| | | 2 | 398 | 754 | 576 | 251.73 | |
| | | 6 | 59 | 86 | 72.5 | 19.09188 | |
| | | 12 | 43 | 55 | 49 | 8.485281 | |
| | | 24 | 49 | 66 | 57.5 | 12.02082 | |
| | | 48 | 54 | 55 | 54.5 | 0.707107 | |
| | | 72 | 54 | 62 | 58 | 5.656854 | 915 |
| A-2 | C57BL/6 | 0 | 46 | 46 | 46 | 0 | |
| | | 2 | 286 | 600 | 443 | 222.0315 | |
| | | 6 | 95 | 125 | 110 | 21.2132 | |
| | | 12 | 45 | 68 | 56.5 | 16.26346 | |
| | | 24 | 46 | 58 | 52 | 8.485281 | |
| | | 48 | 60 | 52 | 56 | 5.656854 | |
| | | 72 | 59 | 64 | 61.5 | 3.535534 | 826 |
| A-1 | C57BL/6 | 0 | 46 | 46 | 46 | 0 | |
| | | 2 | 914 | 1262 | 1088 | 246.0732 | |
| | | 6 | 90 | 128 | 109 | 26.87006 | |
| | | 12 | 44 | 66 | 55 | 15.55635 | |
| | | 24 | 57 | 56 | 56.5 | 0.707107 | |
| | | 48 | 47 | 41 | 44 | 4.242641 | |
| | | 72 | 61 | 115 | 88 | 38.18377 | 1487 |
| Z | C57BL/6 | 0 | 46 | 46 | 46 | 0 | |
| | | 2 | 0 | 0 | 0 | 0 | |
| | | 6 | 0 | 51 | 25.5 | 36.06245 | |
| | | 12 | 0 | 257 | 128.5 | 181.7264 | |
| | | 24 | 0 | 3 | 1.5 | 2.12132 | |
| | | 48 | 5 | 129 | 67 | 87.68124 | |
| | | 72 | 4 | 1 | 2.5 | 2.12132 | 273 |
| CRONY | C57BL/6 | 0 | 46 | 46 | 46 | 0 | |
| | | 2 | 286 | 642 | 464 | 251.73 | |
| | | 6 | 48 | 98 | 73 | 35.35534 | |
| | | 12 | 12 | 56 | 34 | 31.1127 | |
| | | 24 | 16 | 30 | 23 | 9.899495 | |
| | | 48 | 17 | 6 | 11.5 | 7.778175 | |
| | | 72 | 15 | 28 | 21.5 | 9.192388 | 674 |
| A-4 | C57BL/6 | 0 | 46 | 46 | 46 | 0 | |
| | | 2 | 627 | 766 | 696.5 | 98.28784 | |
| | | 6 | 83 | 169 | 126 | 60.81118 | |
| | | 12 | 40 | 47 | 43.5 | 4.949747 | |
| | | 24 | 29 | 30 | 29.5 | 0.707107 | |
| | | 48 | 39 | 18 | 28.5 | 14.84924 | |
| | | 72 | 54 | 29 | 41.5 | 17.67767 | 1014 |
| KRN | C57BL/6 | 0 | 46 | 46 | 46 | 0 | |
| | | 2 | 3584 | 4246 | 3915 | 468.1047 | |
| | | 6 | 122 | 244 | 183 | 86.26703 | |
| | | 12 | 103 | 102 | 102.5 | 0.707107 | |
| | | 24 | 20 | 16 | 18 | 2.828427 | |
| | | 48 | 2 | 0 | 1 | 1.414214 | |
| | | 72 | 0 | 1 | 0.5 | 0.707107 | 4267 |

TABLE 7

IL-12/IL4 and IFN-γ/IL-4 ratios for tested glycolipids (calculated based on the values in Tables 1-6)

| Compound | IL-12 (B6) | IFN-γ (B6) | IL-4 (B6) | IL-12/IL-4 (B6) | IFN-γ/IL-4 (B6) |
|---|---|---|---|---|---|
| A-1 | 4332 | 17485 | 1487 | 2.9 | 12 |
| A-2 | 3969 | 13027 | 826 | 4.8 | 16 |
| A-3 | 1400 | 12751 | 915 | 1.5 | 14 |
| A-4 | 1274 | 10532 | 1014 | 1.3 | 10 |
| A-5 | 2182 | 11775 | 649 | 3.4 | 18 |
| CRONY | 1379 | 11652 | 674 | 2 | 17 |
| KRN | 1440 | 10686 | 4267 | 0.3 | 3 |
| Z | 107 | 770 | 273 | 0.4 | 3 |

| Compound | IL-12 (BALB/c) | IFN-γ (BALB/c) | IL-4 (BALB/c) | IL-12/IL-4 (BALB/c) | IFN-γ/IL-4 (BALB/c) |
|---|---|---|---|---|---|
| A-1 | 14462 | 25633 | 696 | 21 | 37 |
| A-2 | 18864 | 26755 | 623 | 30 | 43 |
| A-3 | 4878 | 21287 | 538 | 9 | 40 |
| A-4 | 5926 | 22676 | 511 | 12 | 44 |
| A-5 | 4949 | 14922 | 382 | 13 | 39 |
| CRONY | 4025 | 19938 | 588 | 7 | 34 |

TABLE 7-continued

IL-12/IL4 and IFN-γ/IL-4 ratios for tested glycolipids
(calculated based on the values in Tables 1-6)

| KRN | 4030 | 21008 | 2117 | 2 | 10 |
|-----|------|-------|------|---|----|
| Z   | 883  | 380   | 232  | 4 | 2  |

Example 2

Determination of the Ability of the Novel Synthetic C-Glycolipids of the Invention to Inhibit Malarial Infection and Tumor Metastasis Mice are administered i.m., s.c., i.v or i.p. with a single dose of synthetic C-glycolipids of the invention GCK109 (A-1 trans-conformer), GCK151 (A-1 cis-conformer) and GCK127 (A-2) or control compounds CRONY=α-C-GalCer and KRN=α-GalCer. The protective effect of the compounds is determined 2-8 weeks after the immunization.

For testing protection against malarial infection, *P. yoelii* sporozoites obtained from dissected salivary glands of infected mosquitoes are used for challenge. Challenge of mice immunized with synthetic C-glycolipids or control compounds to determine the development of blood stage malaria infection is performed by an intravenous (i.v.) injection of 75 viable sporozoites into the tail vein. Starting 4 days after the challenge, daily peripheral blood smears are obtained from each mouse and examined microscopically for the presence of blood stage parasites until day 17 post-challenge. Mice are considered positive for parasitemia if at least one blood stage parasite is observed during the time of examination.

Challenge of mice immunized with synthetic C-glycolipids or control compounds to determine the development of liver-stage malaria infection is performed by i.v. injection of 10,000 viable sporozoites into the tail vein. The outcome of the challenge is determined 40-42 hours later by measuring the *P. yoelii*-specific 18S rRNA molecules in the livers of the mice using a quantitative real-time RT-PCR method, as taught in Bruna-Romero et al., *Int. J. Parasitol.* 31, 1449-1502, 2001. Briefly, after reverse transcription of the extracted RNA, cDNA is generated and its amount analyzed by real-time PCR using in a GeneAmp® 5700 Sequence Detection System (PE Applied Biosystems, Foster City, Calif.). Primers and fluorogenic probe are custom designed using the ABI Prism primer Express software (PE Biosystems), using *P. yoelii* (17XNL) 18S rRNA sequence. For example, primers 5'-GGGGATTGGTTTTGACGTTTTTGCG-3' (54 nM) [SEQ ID NO: 7] and 5'-AAGCATTAAATAAAGCGAATA-CATCCTTAT-3' (60 nm) [SEQ ID NO: 8] can be used, together with the dsDNA-specific dye SYBR Green I incorporated into the PCR reaction buffer (PE Biosystems, Foster City, Calif.) in order to detect the PCR product generated. The temperature profile of the reaction is 95° C. for 10 minutes followed by 35 cycles of denaturation of 95° C. for 15 seconds and annealing/extension at 60° C. for 1 minute. The precise amount of parasite-derived 18S cDNA molecules detected in this assay is determined by linear regression analysis using CT values obtained from both liver samples and those obtained from a standard curve generated with known amounts of plasmid 18S cDNA.

The level of protection of mice immunized with synthetic C-glycolipids or control compounds against development of melanoma lung metastases is determined by first challenging the mice intravenously with $5 \times 10^4$ syngeneic B16 melanoma cells suspended in DMEM supplemented with 10% FCS. Two weeks after challenge, the mice are sacrificed, the lungs removed, and the number of metastatic nodules counted, as described in Fujii et al., *Natl. Immunol.* 3, 867-874 (2002).

All synthetic C-glycolipids of the invention show potent activity in protecting mince against live malarial challenge and melanoma metastasis.

Example 3

Determination of the Adjuvant Effect of the Novel Synthetic C-Glycolipids of the Invention Mice are administered i.m., s.c., i.v or i.p. with a single dose of synthetic C-glycolipids of the invention GCK109 (A-1 trans-conformer), GCK151 (A-1 cis-conformer) and GCK127 (A-2) or control compounds CRONY=☐-C-GalCer and KRN=☐-GalCer, and a sub-optimal dose ($1 \times 10^7$ p.f.u.) of a recombinant adenovirus expressing *P. yoelii* CS protein, AdPyCS (Rodrigues et al., *J. Immunol.*, 158: 1268-1274, 1997). From 2 to 8 weeks after the immunization, some mice are sacrificed and their spleens removed to obtain lymphocytes in order to measure the levels of malaria-specific CD8+ T cell responses by an ELISPOT assay. Mice immunized with AdPyCS alone are used as a control.

Splenocytes from mice immunized with AdPyCS and synthetic C-glycolipids or control compounds, or control mice (immunized only with AdPyCS) are assayed to determine the number of (i) CS-specific $CD8^+$ T-cells producing IFN-γ (Th1 cells) and (ii) CS-specific $CD8^+$ T cells producing IL-4 (Th2 cells). The number of CS-specific $CD8^+$T cells is determined using ELISPOT assay (Miyahira et al, *J. Immunol. Methods* 1995; 181: 45-54). Briefly, 96-well nitrocellulose plates (Millipone, Bedford, Mass.) are coated overnight at room temperature with biotinylated anti-mouse IFN-γ or anti-mouse IL-4 monoclonal antibodies (mAb). After several washes with PBS, serial dilution of splenocytes in culture medium in the presence or absence of peptides corresponding to CD8+ epitope are incubated for 20-24 hours at 37° C. in a 5% $CO_2$ incubator in plates coated with anti-mouse IFN-γ or anti-mouse IL-4 mAb. Following incubation, the plates are washed with PBS-T. Plates are then incubated for 3 hours at room temperature with biotinylated anti-mouse IFN-γ or anti-mouse IL-4 mAb in the plates, respectively. The plates are washed with PBS-T before the addition of Streptavidin-AP conjugate and the incubation for 1 hour at room temperature. Following an additional washes with PBS-T and one wash with distilled water, spots are developed with one step BCIP/NPT reagent. Spots are counted using Immune Spot Reader (Cellular Technology Ltd., Cleveland, Ohio).

The achieved level of antimalarial protection is determined 2-8 weeks later by challenging immunized mice with i.v. injection of live *P. yoelii* sporozoites. Non-immunized mice are used as a control.

As specified in Example 2, supra, the protection is measured by measuring parasite blood and liver stages. Blood stages, are monitored by microscopic examination of Giemsa-stained blood smears, obtained daily from day 3 to day 14 post-challenge with 75 live *P. yoelii* sporozoites. Liver stages are measured by removing livers from the mice at 42 hours after challenge with 10,000 *P. yoelii* sporozoites, and the parasite burden in the livers is determined, by measuring the plasmodial rRNA by a real-time RT-PCR as disclosed in Example 2, supra.

All synthetic C-glycolipids of the invention demonstrate potent adjuvant effect.

Example 4

Determination of Cytokine Profiles of the Compounds of the Invention in an Experimental Human In Vitro NKT Cell System Materials and Methods Generation of Immature Dendritic Cells (DCs) and CD14− PBMCs.

CD14+ cells were isolated from leukopaks, using magnetic beads (Miltenyi biotec, Auburn, Calif.) coupled to an anti-CD14 monoclonal antibody. Immature dendritic cells (DCs) were then generated from the CD14+ cells after a three-day incubation in the presence of 300 U/ml GM-CSF (R&D systems, Minneapolis, Minn.) and 100 U/ml IL-4 (R&D systems, Minneapolis, Minn.). CD14-cells were used as Peripheral Blood Mononuclear Cells (PBMCs) for the following experiments.

In Vitro IFN-γ and IL-4 ELISA Using PBMCs and Immature DCs.

Following irradiation with 3000 rads, $5 \times 10^4$ immature dendritic cells were co-cultured with $5 \times 10^5$ of syngeneic CD14− PBMCs in the presence of 10 ng/ml of various glycolipids (i.e., GCK109 [A-1 trans-conformer], GCK151 [A-1 cis-conformer], GCK127 [A-2], GCK152 [A-7], and control compounds CRONY=α-C-GalCer and KRN=α-GalCer) in a 96-well plate. After culture for 18 hours, the concentration of IFN-γ or IL-4 in the culture supernatants was determined by ELISA (BD Pharmingen, San Diego, Calif.) following manufacturer's instructions.

In Vitro IFN-γ and IL-4 ELISPOT Assay Using PBMCs and Immature DCs.

96 well nitrocellulose plates (Milititer HA, Millipore) were coated with 10 µg/ml of anti-human interferon γ mAb (Mabtech, Ohio), contained in 75 µl of PBS. After overnight incubation at room temperature, the wells were washed repeatedly and blocked with culture medium for 1 hour at 37° C. Following irradiation with 3000 rads, $5 \times 10^4$ immature dendritic cells were co-cultured with $5 \times 10^5$ of syngeneic CD14− PBMCs in the presence of 100 ng/ml of various glycolipids (i.e., GCK109 [A-1 trans-conformer], GCK151 [A-1 cis-conformer], GCK127 [A-2], GCK152 [A-7], and control compounds CRONY=α-C-GalCer and KRN=α-GalCer) in the ELISPOT plate for 22-26 hours at 37° C. and 5% $CO_2$. After extensive washing of the plates with PBS 0.05% Tween 20 (PBS T), 1 µg/ml of biotinylated anti-human interferon γ mAb (Mabtech, Ohio), in PBS-T was added, and incubated overnight at 4° C. After washing with PBST, the plates were incubated with 100 µl of peroxidase-labeled streptavidin (Kirkegaard & Perry Laboratories), diluted according to the manufacturer's instruction. The spots were developed after 1 hour of incubation, by adding 50 mM Tris HCl pH7.5, containing 1 mg/ml of 3 3' diaminobenzidine tetrahydrochloride dihydrate (DAB) plus 5 µg/10 ml of 30% $H_2O_2$. After 10 to 15 minutes, the number of spots corresponding to IFN-γ secreting cells was determined using a stereomicroscope. In order to determine the number of epitope specific IL-4 producing NKT cells, a similar procedure was followed, except that a pair of anti-human IL-4 mAbs (Mabtech, Ohio) was used.

Results

Figure 5A:
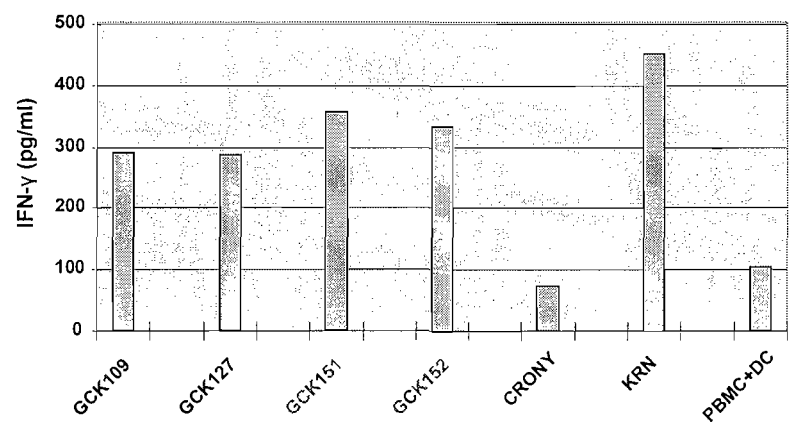
FIGS. 5A and 5B depict cytokine levels of the compounds of the invention measured by ELISA in an experimental human in vitro NKT cell system. Concentration of IFN-γ or IL-4 was determined by ELISA in the culture supernatants of immature dendritic cells (DCs) which were co-cultured for 18 hours with syngeneic CD14− Peripheral Blood Mononuclear Cells (PBMCs) in the presence of various glycolipids (i.e., GCK109 [trans-A-1], GCK151 [cis-A-1], GCK127 [A-2], GCK152 [A-7], and control compounds CRONY=α-C-GalCer and KRN=α-GalCer).
Figure 5B:
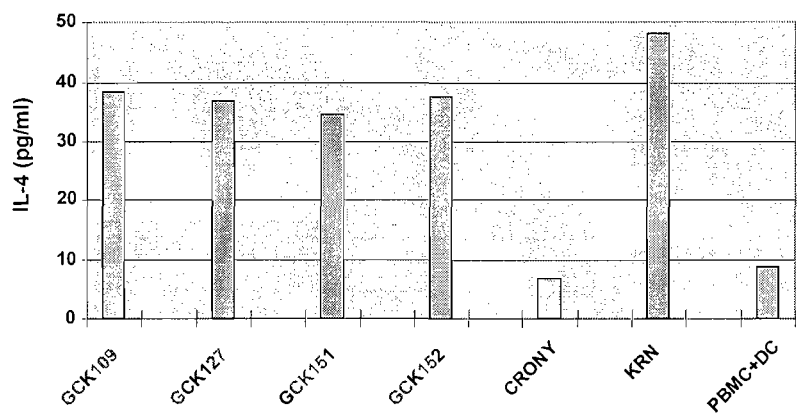

In ELISA assays, as shown in FIGS. 5A-B, GCK109 (A-1 trans-conformer), GCK151 (A-1 cis-conformer), GCK127 (A-2), and GCK152 [A-7] activated PBMCs to produce similar level of IFN-γ, as well as IL-4 as compared to KRN (α-GalCer) after 18 hours of co-culture with immature DCs in vitro.

Figure 6A:
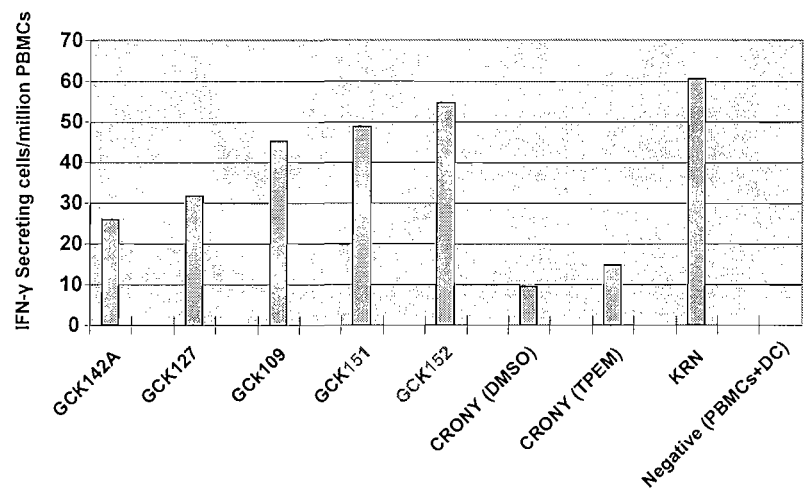
FIGS. 6A and 6B depict the numbers of cytokine-secreting PBMCs upon incubation with the compounds of the invention measured by ELISPOT in an experimental human in vitro NKT cell system. The numbers of PBMCs secreting IFN-γ or IL-4 was determined by ELISPOT upon co-culturing of immature DCs with syngeneic CD14− PBMCs in the ELISPOT plate for 22-26 hours in the presence of various glycolipids (i.e., GCK142A [A-6] GCK109 [trans-A-1], GCK151 [cis-A-1], GCK127 [A-2], GCK152 [A-7], and control compounds CRONY=α-C-GalCer and KRN=α-GalCer).
Figure 6B:
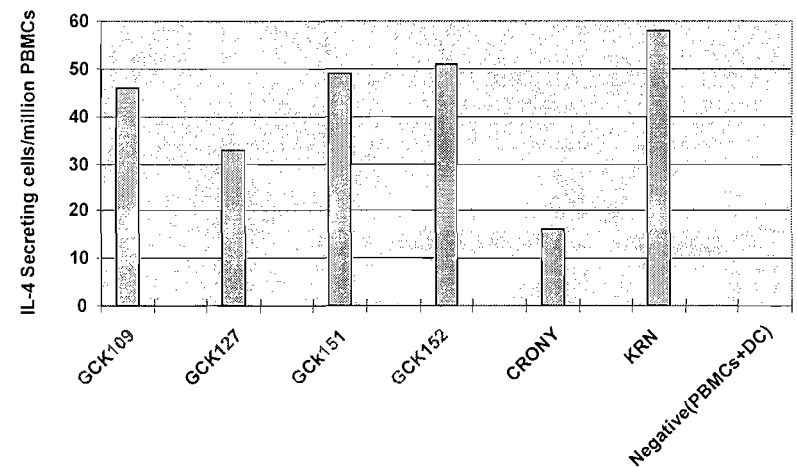

In ELISPOT assays, as shown in FIGS. 6A-B, GCK151 (A-1 cis-conformer) and GCK152 [A-7] consistently stimulated high frequency of PBMCs to secrete both IFN-γ and IL-4, and the frequency of activated PBMCs is similar to that stimulated by KRN. GCK109 (A-1 trans-conformer) and GCK127 (A-2) were also able to stimulate similar frequency of PBMCs at 24 hours after co-culture with immature DCs.

The above data also demonstrate the interaction of the tested C-glycolipids of the invention with CD1d on one side and the invariant NKT receptor on the other side. This is an important indication that the compounds will be active in humans in vivo.

It is possible, however, that the described human in vitro cell system may not allow to compare the activity of the various compounds in a way that will provide projections for their in vivo performance. For example, this in vitro cell system does not take into account several important factors that influence the true biological response in vivo, including differing rates of compound degradation in vivo and differing kinetics of their effects. Also, the interaction tested in this experimental system is limited to NKT cells and CD1d antigen presenting cells. In vivo, other DCs and NK cells will interfere to further release IL-12 and IFN-γ. Finally, the control compound KRN is more soluble in an aqueous solution than the more lipohilic tested compounds of the invention, which makes the control compound more bioavailable for in vitro testing in cell culture and which may not reflect the in vivo situation, where the test compounds may have a more prolonged effect.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

Patents, patent applications, publications, product descriptions, and protocols are cited throughout this application, the disclosures of which are incorporated herein by reference in their entireties for all purposes.

What is claimed is:

1. A compound of formula (I)

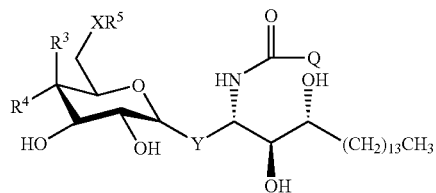

(I)

wherein
X is O;
Y is —CH=CH—;
Q is $C_6$-$C_8$ alkyl substituted with phenyl;
$R^3$ is —OH and $R^4$ is H, or $R^3$ is H and $R^4$ is —OH; and
$R^5$ is hydrogen;
or a pharmaceutically acceptable salt or ester thereof.

2. The compound of claim 1, wherein $R^3$ is OH and $R^4$ is H.

3. The compound of claim 1 or claim 2, wherein —CH=CH— of Y in the compound of formula (I) has a trans conformation.

4. A compound having the formula

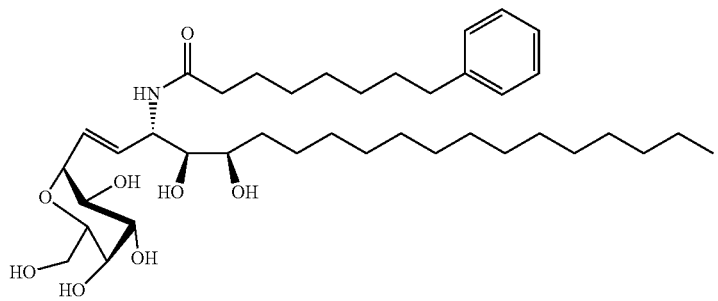

or a pharmaceutically acceptable salt or ester thereof.

5. A pharmaceutical composition, comprising the compound as defined in claim 1 or claim 4, and a pharmaceutically acceptable carrier.

6. The composition of claim 5, which further comprises an antigen.

7. The composition of claim 6, wherein the antigen is a viral, parasite-derived, or tumor antigen.

8. The composition of claim 7, wherein the antigen is a malaria-specific antigen.

9. The composition of claim 8, wherein the antigen is derived from plasmodium species.

10. A method of selectively inducing a Th1-type immune response in a mammal, the method comprising administering to the mammal an effective amount of the compound as defined in claim 1 or claim 4.

11. The method of claim 10, wherein the compound induces enhanced secretion of IL-12.

12. A method for relieving or alleviating at least one symptom of a disease which requires a Th-1-type response for control in a mammal in need thereof, the method comprising administering to the mammal an effective amount of the compound as defined in claim 1 or claim 4,
wherein the disease is human immunodeficiency virus (HIV), hepatitis C virus (HCV), hepatitis B virus (HBV), malaria, carcinoma of the prostate, or melanoma.

13. The method of claim 12, wherein the disease is HIV.

14. The method of claim 12, wherein the disease is HCV.

15. The method of claim 12, wherein the disease is HBV.

16. The method of claim 12, wherein the disease is malaria.

17. The method of claim 12, wherein the disease is carcinoma of the prostate or melanoma.

18. A method for augmenting the immunogenicity of an antigen in a mammal, the method comprising immunizing the mammal conjointly with the antigen and with an adjuvant comprising the compound as defined in claim 1 or claim 4,
wherein the antigen is HIV-specific or malaria-specific.

19. The method of claim 18, wherein the antigen and the adjuvant are administered simultaneously.

20. The method of claim 19, wherein the antigen is HIV-specific.

21. The method of claim 19, wherein the antigen is malaria-specific.

22. A method of preparing a compound of formula (I)

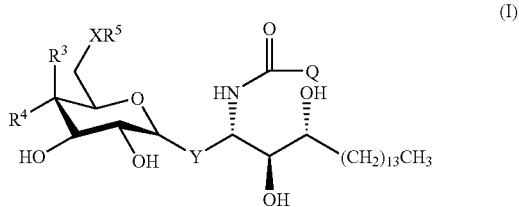

(I)

wherein
X is O;
Y is —CH=CH—;
Q is $C_6$-$C_8$ alkyl substituted with phenyl;
$R^3$ is —OH and $R^4$ is H, or $R^3$ is H and $R^4$ is —OH; and
$R^5$ is hydrogen,
or a pharmaceutically acceptable salt or ester thereof,
the method comprising the steps of:
(a) reacting a compound of the following formula

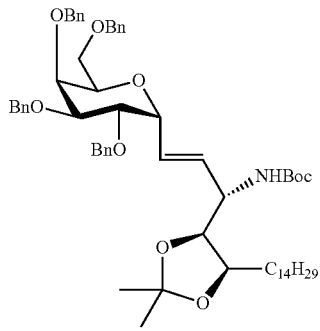

to first remove the Boc group, followed by treatment with a p-nitrophenyl ester having the formula III:

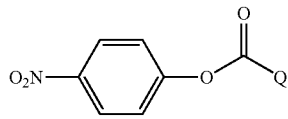

(III)

wherein Q is as defined above; and
(b) deprotecting the Bn and —$C(CH_3)_2$ groups, and
(c) optionally converting the compound from step (b) into a pharmaceutically acceptable salt or ester thereof.

* * * * *